United States Patent
Whalen et al.

(10) Patent No.: US 9,353,158 B2
(45) Date of Patent: May 31, 2016

(54) HEPATITIS B VIRUS VACCINES

(71) Applicant: AltraVax, Inc., Sunnyvale, CA (US)

(72) Inventors: Robert Gerald Whalen, Foster City, CA (US); Clayton W. Beard, Chapel Hill, NC (US); Li Xu, Cupertino, CA (US); Hakima Sbai, Providence, RI (US)

(73) Assignee: Altravax, Inc., Sunnyvale, CA (US)

( * ) Notice: Subject to any disclaimer, the term of this patent is extended or adjusted under 35 U.S.C. 154(b) by 0 days.

(21) Appl. No.: 14/207,135

(22) Filed: Mar. 12, 2014

(65) Prior Publication Data

US 2014/0316122 A1    Oct. 23, 2014

Related U.S. Application Data

(60) Provisional application No. 61/785,838, filed on Mar. 14, 2013.

(51) Int. Cl.
*A61K 39/29*    (2006.01)
*C07K 14/005*    (2006.01)
*A61K 39/00*    (2006.01)

(52) U.S. Cl.
CPC ........... *C07K 14/005* (2013.01); *A61K 2039/53* (2013.01); *C12N 2730/10122* (2013.01); *C12N 2730/10134* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,803,164 | A | 2/1989 | Hitzeman et al. |
| 6,551,820 | B1 | 4/2003 | Mason et al. |
| 6,740,323 | B1 | 5/2004 | Selby et al. |
| 2002/0198162 | A1 | 12/2002 | Punnonen et al. |
| 2004/0001849 | A1 | 1/2004 | Punnonen et al. |
| 2004/0110295 | A1 | 6/2004 | Punnonen et al. |
| 2006/0035853 | A1 | 2/2006 | Yang et al. |
| 2006/0045888 | A1 | 3/2006 | Punnonen et al. |
| 2008/0267996 | A1 | 10/2008 | Schneider et al. |

FOREIGN PATENT DOCUMENTS

| | | |
|---|---|---|
| EP | 0241021 A2 | 10/1987 |
| WO | WO9941383 A1 | 8/1999 |

OTHER PUBLICATIONS

De Maddalena et al., "High level of genetic heterogeneity in S and P genes of genotype D hepatitis B virus," Virology 365: 113-124 (2007).*

(Continued)

*Primary Examiner* — Benjamin P Blumel
*Assistant Examiner* — M. Franco Salvoza
(74) *Attorney, Agent, or Firm* — Fish & Richardson P.C.

(57) ABSTRACT

This document provides methods and materials for producing immune responses against hepatitis B viruses. For example, polypeptides, nucleic acid molecules encoding such polypeptides, virus-like particles containing such polypeptides, vaccine preparations containing one or more polypeptides provided herein, vaccine preparations containing one or more nucleic acid molecules provided herein, vaccine preparations containing one or more virus-like particles provided herein, and methods for inducing immune responses against hepatitis B viruses within mammals (e.g., humans) are provided.

20 Claims, 52 Drawing Sheets

(56) References Cited

OTHER PUBLICATIONS

Lai et al., "The oncogenic potential of hepatitis B virus rtA181T/surface truncation mutant," Antiviral Therapy 13: 875-879 (2008).*
GenBank Accession No. EF514349 (2007).*
Apt et al., "Tetravalent neutralizing antibody response against four dengue serotypes by a single chimeric dengue envelope antigen," Vaccine, 24(3):335-44. Jan. 16, 2006.
Norder et al., "Genetic relatedness of hepatitis B viral strains of diverse geographical origin and natural variations in the primary structure of the surface antigen," J Gen Virol., 74 ( Pt 7):1341-1348, Jul. 1993.
Raviprakash et al., "A chimeric tetravalent dengue DNA vaccine elicits neutralizing antibody to all four virus serotypes in rhesus macaques," Virology, 353(1):166-73, Sep. 15, 2006.
Sbai and Whalen, "Creation of superagonist epitope sequences in the hepatitis B envelope protein using mutagenesis and DNA vaccination," DNA Cell Biol., 21(2):129-135, Feb. 2002.
Stemmer et al., "Single-step assembly of a gene and entire plasmid from large numbers of oligodeoxyribonucleotides," Gene, 164(1):49-53, Oct. 16, 1995.
GenBank® Accession No. AF046996; GI No. 3150070, "Woolly monkey hepatitis B Virus, complete genome," May 22, 1998, 3 pages.
GenBank® Accession No. D00220; GI No. 163838595, "Hepatitis B virus DNA, complete genome, strain: LSH," Dec. 21, 2007, 3 pages.
GenBank® Accession No. J02203; [Replaced by V01460] GI No. 329640, "Human hepatitis B virus (subtype ayw), complete genome," Aug. 2, 1993, 2 pages.
GenBank® Accession No. J04514; GI No. 336146, "Woodchuck hepatitis B virus (WHV8), complete genome," Aug. 3, 1993, 2 pages.
GenBank® Accession No. U46935; GI No. 1814218, "Hepatitis B virus complete genome," Feb. 5, 1997, 3 pages.
GenBank® Accession No. V01460; GI No. 62276, "Hepatitis B virus (strain ayw) genome," Jan. 28, 2003, 3 pages.
GenBank® Accession No. X02763; GI No. 59418, "Hepatitis b virus genome (serotype adw2)," Apr. 18, 2005, 3 pages.
International Search Report for PCT/US2014/024882 mailed Jun. 23, 2014, 14 pages.
International Preliminary Report on Patentability for PCT/US2014/024882, mailed Sep. 24, 2015, 8 pages.

* cited by examiner

Figure 2

```
HBV ayw 'a'-loop (+)                    tATGACTACcGCTCAAGGAACCTCTATGTA (SEQ ID NO:60)
------------------------------------------------------------------------------------
Chibbon(+)       ACCATGCAAAACCTGtATGACTACcGCTCAAGGAACCTCTATGTATCCCTCATGTTGTTG
                                                                      (SEQ ID NO:61)
WM(+)            ACCCTGCAGGACCTGtATGACTACcGCTCAAGGAACCTCTATGTATCCCTCATGTTGCTG
                                                                      (SEQ ID NO:62)
WD(+)            CAATTGCAGACAATGtATGACTACcGCTCAAGGAACCTCTATGTATCCTTACTGTTGTTG
                                                                      (SEQ ID NO:63)
```

Figure 4

Human Hepatitis B Virus Envelope (subtype ayw) (SEQ ID NO:1)

ATGCAGTGGAATTCCACAACCTTCCACCAAACTCTGCAAGATCCCAGAGTGAGAGGCCTGTATT
TCCCTGCTGGTGGCTCCAGTTCAGGAACAGTAAACCCTGTTCTGACTACTGCCTCTCCCTTATC
GTCAATCTTCTCGAGGATTGGGGACCCTGCGCTGAACATGGAGAACATCACATCAGGATTCCTA
GGACCCCTTCTCGTGTTACAGGCGGGGTTTTTCTTGTTGACAAGAATCCTCACAATACCGCAGA
GTCTAGACTCGTGGTGGACTTCTCTCAATTTTCTAGGGGGAACTACCGTGTGTCTTGGCCAAAA
TTCGCAGTCCCCAACCTCCAATCACTCACCAACCTCTTGTCCTCCAACTTGTCCTGGTTATCGC
TGGATGTGTCTGCGGCGTTTTATCATCTTCCTCTTCATCCTGCTGCTATGCCTCATCTTCTTGT
TGGTTCTTCTGGACTATCAAGGTATGTTGCCCGTTTGTCCTCTAATTCCAGGATCCTCAACAAC
CAGCACGGGACCATGCCGGACCTGCATGACTACTGCTCAAGGAACCTCTATGTATCCCTCCTGT
TGCTGTACCAAACCTTCGGACGGAAATTGCACCTGTATTCCCATCCCATCATCCTGGGCTTTCG
GAAAATTCCTATGGGAGTGGGCCTCAGCCCGTTTCTCCTGGCTCAGTTTACTAGTGCCATTTGT
TCAGTGGTTCGTAGGGCTTTCCCCCACTGTTTGGCTTTCAGTTATATGGATGATGTGGTATTGG
GGGCCAAGTCTGTACAGCATCTTGAGTCCCTTTTTACCGCTGTTACCAATTTTCTTTTGTCTTT
GGGTATACATTTAA

Human Hepatitis B Virus Envelope (subtype ayw) (SEQ ID NO:2)

MQWNSTTFHQTLQDPRVRGLYFPAGGSSSGTVNPVLTTASPLSSIFSRIGDPALNMENITSGFL
GPLLVLQAGFFLLTRILTIPQSLDSWWTSLNFLGGTTVCLGQNSQSPTSNHSPTSCPPTCPGYR
WMCLRRFIIFLFILLLCLIFLLVLLDYQGMLPV

Figure 5

Woolly Monkey Hepatitis Virus Envelope (SEQ ID NO:3)

ATGCAGTGGAATTCCACTTCCTTCCAGAGTTATCTTCAGAATCCAAAGGTCAGAGGC
CTCTACTTTCCTGCTGGTGGCTCAACTTCAAGCATTGTCAACCCTGTTCCGACCACTG
CCTCCACCACATCGTCAAGCTTCTCGACGACTGGGGTCCCTGTCAGCACCATGGACA
TCACTTCATCAGGATTCCTAGGACCCCTTCTCGCATTACAGGCGGTGTTTTTCTTGTT
GACAAAAATCCTCACAATGCCACAGAGTCTAGACTCGTTGTGGACTTCTCTCAATTT
TCTAGGGGGAACACCAGCGTGTCCTGGCCTAAATTCGCAGTCCCCAACCTCCAGTCA
CTCACCAACCTGCTGTCCACCGACTTGTCCTGGGTATCGCTGGATGTGTTTGCGGCGT
TCTATCATCTTCCTCTTCATCCTGCTTCTATGCCTCATCTTCTTGTTGGTTCTTCTGGA
CTACCAAGGTATGTTGCCCGTGTGTCCTCTTCTACCAACAGTTACAGGAACAACAAC
AACAACGGGACCCTGCAGGACCTGCACGCCAATTGTTCCAGGCATCTCTTCGTATCC
CTCATGTTGCTGTACCAAACCTACGGACGGAAACTGCACTTGTATTCCCATCCCCTC
ATCATGGGCTTTCGCAAAGTTCCTATGGGACTGGGCCTTAGCCCGTTTCTCCTGGCTC
AATTCACTTCTGCCATTTGTTCAGTGGTTCGCAGGGCTTTCCCCCACTGTATGGCTTT
TAGTTATATGGATGATGTGGTTCTGGGGGCCAAGTCTGTTCAGCATCTTGAGTCCCTT
CTTGCCTCTGTTACCACTTTTCTTTGGCTTTGGGTATACATTTAA

Woolly Monkey Hepatitis Virus Envelope (SEQ ID NO:4)

MQWNSTSFQSYLQNPKVRGLYFPAGGSTSSIVNPVPTTASTTSSSFSTTGVPVSTMDITSS
GFLGPLLALQAVFFLLTKILTMPQSLDSLWTSLNFLGGTPACPGLNSQSPTSSHSPTCCPP
TCPGYRWMCLRRSIIFLFILLLCLIFLLVLLDYQGMLPVCPLLPTVTGTTTTTGPCRTCTPI
VPGISSYPSCCCTKPTDGNCTCIPIPSSWAFAKFLWDWALARFSWLNSLLPFVQWFAGLS
PTVWLLVIWMMWFWGPSLFSILSPFLPLLPLFFWLWVYI

Figure 6

HBV (adw2) PreS2 plus Woodchuck Hepatitis Virus S Envelope (SEQ ID NO:5)

ATGCAGTGGAATTCCACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGTGACGAACATGTCA
CCATCAAGTCTCCTAGGACTCCTCGCAGGATTACAGGTGGTGTATTTCTTGTGGACA
AAAATCCTAACAATAGCTCAGAATCTAGATTGGTGGTGGACTTCTCTCAGTTTTCCA
GGGGGCATACCAGAGTGCACTGGCCAAAATTCGCAGTTCCAAACTTGCAAACACTT
GCCAACCTCCTGTCCACCAACTTGCAATGGCTTTCGTTGGATGTATCTGCGGCGTTTT
ATCATATACCTATTAGTCCTGCTGCTGTGCCTCATCTTCTTGTTGGTTCTCCTGGACT
GGAAAGGTTTAATACCTGTCTGTCCTCTTCAACCCACAACAGAAACAACAGTCAATT
GCAGACAATGCACAATCTCTGCACAAGACATGTATACTCCTCCTTACTGTTGTTGTTT
AAAACCTACGGCAGGAAATTGCACTTGTTGGCCCATCCCTTCATCATGGGCTTTAGG
AAATTACCTATGGGAGTGGGCCTTAGCCCGTTTCTCTTGGCTCAATTTACTAGTGCCC
TTGCTTCAATGGTTAGGAGGAATTTCCCTCATTGCGTGGTTTTGCTTATATGGATGA
TTTGGTTTTGGGGGCCCGCACTTCTGAGCATCTTACCGCCATTTATTCCCATATTTGT
TCTGTTTTTCTTGATTTGGGTATACATTTAA

HBV (adw2) PreS2 plus Woodchuck Hepatitis Virus S Envelope (SEQ ID NO:6)

MQWNSTAFHQ

Figure 7

Composite Chimpanzee-Gibbon Hepatitis Virus Envelope (SEQ ID NO:7)

```
ATGCAGTGGAATTCTACAGTATTCCACCAAGCTCTGCAAGATCCCAGAGTACGGGGCCTATACT
TTCCTGTTGGTGGCTCCAGTTCAGGAACATTGAACCCTGTTCCGAATACTGCCTCTCACATCTC
GTCAGTCTTCTCGACGACTGGGGACCCTGCACCGAACATGGAGAACATCACATCAGGATTCCTA
GGACCCCTGCTCGTGTTACAGGCGGGGTTTTTCTTGTTGACAAAAATCCTCACAATACCACAGA
GTCTAGACTCGTGGTGGACTTCTCTCAATTTTCTAGGGGGAGCACCCGTGTGTCCTGGCCAAAA
TTCGCAGTCCCCAACCTCCAATCACTCACCAACCTCTTGTCCTCCAATTTGTCCTGGCTATCGC
TGGATGTGTCTGCGGCGTTTTATCATCTTCCTCTTCATCCTGCTGCTATGCCTCATCTTCTTGT
TGGTTCTTCTGGACTATCAAGGTATGTTGCCCGTTTGTCCTCTACTTCCAGGATCATCGACCAC
CAGCACGGGACCATGCAAAACCTGCACGATCCCTGCTCAAGGAACCTCTTTGATTCCCTCATGT
TGTTGTACAAAACCTTCGGACGGAAATTGCACTTGTATTCCCATCCCATCGTCTTGGCTTTCG
CAAAATTCCTATGGGAGTGGGCCTCAGTCCGTTTCTCCTGGCTCAGTTTACTAGCTCCATTTGT
TCAGTGGTTCGCAGGGCTTTCCCCCACTGCTTGGCTTTTAGCTATATGGATCATCTGGTATTGG
GGGCCAAATCTGTACAACATCTTGAATCCATTTATACCGCTGTTACCAATTTTCTTTTGTCTTT
GGGTATACATTTAA
```

Composite Chimpanzee-Gibbon Hepatitis Virus Envelope (SEQ ID NO:8)

```
MQWNSTVFHQALQDPRVRGLYFPVGGSSSGTLNPVPNTASHISSVFSTTGDPAPNMENI
TSGFLGPLLVLQAGFFLLTKILTIPQSLDSWWTSLNFLGGAPVCPGQNSQSPTSNHSPTSC
PPICPGYRWMCLRRFIIFLFILLLCLIFLLVLLDYQGMLPVCPLLPGSSTTSTGPCKTCTIPA
QGTSLIPSCCCTKPSDGNCTCIPIPSSWAFAKFLWEWASVRFSWLSLLAPFVQWFAGLSP
TAWLLAIWIIWYWGPNLYNILNPFIPLLPIFFCLWVYI
```

Figure 8

6101 nucleic acid sequence (SEQ ID NO:9)

ATGCAGTGGAATTCTACAGTATTCCACCAAACTCTGCAAGATCCCAGAGTGGGGGGT
CTGTATCTTCCTGCTGGTGGCTCCAGTTCAGGAACAGTAAACCCTGTTCTGACTACTG
CCTCTCCCTTATCGTCAATCTTCTCGAGGATTGGGGACCCTGCGCTGAACATGGAGA
ACATCACATCAGGATTCCTAGGACCCCTTCTCGTGTTACAGGCGGGGTTTTTCTTGAT
GACAAAAATCCTCACAATGCCGCAGAGTCTAGACTCGTGGTGGACTTCTCTCAATTT
TCTAGGGAGAGCACCCGTGTGTCCTGGCCAAAATTCGCAGTCCCCAACCTCCAATCA
CTCACCAACCTCTTGTCCTCCAATTTGTCCTGGCTATCGCTGGATGTGTCTGCGGCGT
TTTATCATCTTCCTCTTCATCCTGCTGCTATGCCTCATCTTCTTGTTGGTTCTTCTGGA
CTATCGAGGTATGTTGCCCGTTTGTCCTCTACTTCCAGGATCATCGACCACCAGCAC
GGGACCATGCAAAACCTGCACGATCCCTGCTCAAGGAACCTCTTTGATTCCCTCATG
TTGTTGTACAAAACCTTCGGACGGAAATTGCACTTGTATTCCCATCCCATCGTCTTGG
GCTTTCGCAAAATTCCTATGGGAGTGGGCCTCAGTCCGTTTCTCCTGGCTCAGTTTAC
TAGCTCCATTTGTTCAGCGGTTCGCAGGGCTTTCCCCCACTGCTTGGCTTTTAGCTAT
ATGGATCATCTGGTATTGGGGGCCAAATCTGTACAACATCTTGAGTCCCTTCTTGCC
GCTGTTACCAATTTTCTTTTGTCTTTGGGTATACATTTAAATGCTAGAGGTACCCTGA 6101 amino acid sequence (SEQ ID NO:10)

MQWNSTVFHQTLQDPRVGGLYLPAGGSSSGTVNPVLTTASPLSSIFSRIGDPALNMENIT
SGFLGPLLVLQAGFFLMTKILTMPQSLDSWWTSLNFLGRAPVCPGQNSQSPTSNHSPTSC
PPICPGYRWMCLRRFIIFLFILLLCLIFLLVLLDYRGMLPVCPLLPGSSTTSTGPCKTCTIPA
QGTSLIPSCCCTKPSDGNCTCIPIPSSWAFAKFLWEWASVRFSWLSLLAPFVQRFAGLSPT
AWLLAIWIIWYWGPNLYNILSPFLPLLPIFFCLWVYI

Figure 9

6102 nucleic acid sequence (SEQ ID NO:11)

ATGCAGTGGAATTCCACAACCTTCCACCAAACTCTGCAGGATCCCAGAGTCAGGGG
TCTGTATCTTCCTGCTGGTGGCTCCAGTTCAGGAACAGTAAACCCTGCTCCGAATAC
TGCCTCTCACATCTCGTCAGTCTTCTCGACGACTGGGGACCCTGCACCGAACATGGA
GAACATCACATCAGGATTCCTAGGACCCCTGCTCGTGTTACAGGCGGGGTTTTTCTT
GTTGACAAAAATCCTCACAATGCCACAGAGTCTAGACTCGTTGTGGACTTCTCTCAA
TTTTCTAGGGGAACACCAGCGTGTCTTGGCCAAAATTCGCAGTCCCCAACCTCCAA
TCACTCACCAACCTCTTGTCCTCCAACTTGTCCTGGTTATCGCTGGATGTGTCTGCGG
CGTTTTATCATCTTCCTCTTCATCCTGCTGCTATGCCTCATCTTCTTGTTGGTTCTTCT
GGACTATCGAGGTATGTTGCCCGTTTGTCCTCTAATTCCAGGATCCTCAACAACCAG
CACGGGACCTTGCAGGACCTGTATGACTACCGCTCAAGGAACCTCTATGTATCCCTC
ATGTTGTTGTACAAAACCTTCGGACGGAAATTGCACCTGTATTCCCATCCCATCATC
CTGGGCTTTCGGAAAATTCCTATGGGACTGGGCCTCAGCCCGTTTCTCCTGGCTCAG
TTTACTAGTGCCATTTGTTCAGCGGTCGCAGGGCTTTCTCCCACTGCTTGGCTTTCA
GTTATATGGATGATGTGGTATTGGGGACCAAGTCTGTACAGCATCTTGAGTCCCTTT
TTACCGCTGTTACCAATTTTCTTTGTCTTTGGGTATACATTTAA 6102 amino acid sequence (SEQ ID NO:12)

MQWNSTTFHQTLQDPRVRGLYLPAGGSSSGTVNPAPNTASHISSVFSTTGDPAPNMENI
TSGFLGPLLVLQAGFFLLTKILTMPQSLDSLWTSLNFLGGTPACLGQNSQSPTSNHSPTSC
PPTCPGYRWMCLRRFIIFLFILLLCLIFLLVLLDYRGMLPVCPLIPGSSTTSTGPCRTCMTT
AQGTSMYPSCCCTKPSDGNCTCIPIPSSWAFGKFLWDWASARFSWLSLLVPFVQRFAGL
SPTAWLSVIWMMWYWGPSLYSILSPFLPLLPIFFCLWVYI

Figure 10

6103 nucleic acid sequence (SEQ ID NO:13)

ATGCAGTGGAATTCCACTGCCTTCCACCAAACTCTGCAGGATCCCAGAGTCAGGGGT
CTGTATCTCCCTGCTGGTGGCTCCAGTTCAGGAACAGTAAACCCTGCTCCGAATATT
GCCTCTCACATCTCGTCAATCTCCGCGAGGACTGGGGACCCTGCACCGAACATGGAG
AACATCACATCAGGATTCCTAGGACCCCTGCTCGTGTTACAGGCGGTGTTTTTCTTGT
TGACAAGAATCCTCACAATACCGCAGAGTCTAGACTCGTGGTGGACTTCTCTCAATT
TTCTAGGGGGAACTACCGTGTGTCCTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATATACCTATTAGTCCTGCTGCTGTGCCTCATCTTCTTGTTGGTTCTTCTGG
ACTATCAAGGTATGTTGCCCGTTTGTCCTCTAATTCCAGGATCCTCAACAACCAGCA
CGGGACCATGCAAAACCTGTATGACTACCGCTCAAGGAACCTCTATGTATCCCTCAT
GTTGTTGTACAAAACCTTCGGACGGAAATTGCACTTGTATTCCCATCCCATCATCCTG
GGCTTTCGGAAAATTCCTATGGGAGTGGGCCTCAGCCCGTTTCTCCTGGCTCAGTTT
ACTAGTGCCATTTGTTCAGCGGTTCGCAGGGCTTTCCCCCACTGTTTGGCTTTCAGTT
ATATGGATGATTTGGTTTTGGGGGCCAAGTCTGTACAGCATCTTGAGTCCCTTTTTAC
CGCTGTTACCAATTTTCTTTTGTCTTTGGGTATACATTTAA 6103 amino acid sequence (SEQ ID NO:14)

MQWNSTAFHQTLQDPRVRGLYLPAGGSSSGTVNPAPNIASHISSISARTGDPAPNMENIT
SGFLGPLLVLQAVFFLLTRILTIPQSLDSWWTSLNFLGGTTVCPGQNSQSPTSNHSPTSCP
PTCPGYRWMCLRRFIIYLLVLLLCLIFLLVLLDYQGMLPVCPLIPGSSTTSTGPCKTCMTT
AQGTSMYPSCCCTKPSDGNCTCIPIPSSWAFGKFLWEWASARFSWLSLLVPFVQRFAGL
SPTVWLSVIWMIWFWGPSLYSILSPFLPLLPIFFCLWVYI

Figure 11

6104 nucleic acid sequence (SEQ ID NO:15)

ATGCAGTGGAATTCTACAACCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCACAGAGTCTAGACTCGTGGTGGACTTCTCTCAATT
TTCTAGGGGGAACTACCGTGTGTCTTGGCCTAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTTCTATGCCTCATCTTCTTGTTGGTTCTTCTGG
ACTATCAAGGTATGTTGCCCGTTTGTCCCCTAATTCCAGGATCCTCAACAACCAGCA
CGGGACCATGCAAAACCTGTATGACTACCCCTCAAGGAACCTCTATGTATCCCTCAT
GTTGCTGTACCAAACCTTCGGACGGAAATTGCACCTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGTGGTTCGTAGGGCTTTCCCCCACTGCTTGGCTTTTGGC
TATATGGATCATCTGGTATTGGGGGCCAAATCTGTACAACATCTTGAATCCCTTTTTA
CCGCTGTTACCAATTTTCTTTTGTCTTTGGGTATACATTTAA 6104 amino acid sequence (SEQ ID NO:16)

MQWNSTTFHQTLQDPRVRGLYLPAGGSSSGTVNPAPNIASHISSISARTGDPALNMENIT
SGFLGPLLVLQAGFFLLTRILTIPQSLDSWWTSLNFLGGTTVCLGLNSQSPTSNHSPTSCP
PTCPGYRWMCLRRFIIFLFILLLCLIFLLVLLDYQGMLPVCPLIPGSSTTSTGPCKTCMTTP
QGTSMYPSCCCTKPSDGNCTCIPIPSSWAFGKFLWEWASARFSWLSLLVPFVQWFVGLS
PTAWLLAIWIIWYWGPNLYNILNPFLPLLPIFFCLWVYI

Figure 12

6105 nucleic acid sequence (SEQ ID NO:17)

ATGCAGTGGAATTCCACTGCCTTCCACCAAACTCTGCAGGATCCCAGAGTCAGGGGT
CTGTATCTTCCTGCTGGTGGCTCCAGCTCAGGAACAGTAAACCCTGCTCCGAATATT
GCCTCTCACATCTCGTCAATCTCCGCGAGGATTGGGGACCCTGCGCTGAACATGGAG
AACATCACATCAGGATTCCTAGGACCCCTTCTCGCATTACAGGCGGTGTTTTTCTTGT
TGACAAAAATCCTCACAATGCCACAGAGTCTAGACTCGTGGTGGACTTCTCTCAATT
TTCTAGGGGGAACTACCGTGTGTCTTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTAATTCCAGGATCCTCAACAACCAGCA
CGGGACCATGCAAAACCTGTATGACTACCGCTCAAGGAACCTCTATGTATCCCTCAT
GTTGTTGTACAAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATGATGTGGTATTGGGGGCCAAGTCTGTTCAGCATCTTGAGTCCCTTCTTG
CCTCTGTTACCAATTTTCTTTTGTCTTTGGGTATACATTTAA 6105 amino acid sequence (SEQ ID NO:18)

MQWNSTAFHQTLQDPRVRGLYLPAGGSSSGTVNPAPNIASHISSISARIGDPALNMENIT
SGFLGPLLALQAVFFLLTKILTMPQSLDSWWTSLNFLGGTTVCLGQNSQSPTSNHSPTSC
PPTCPGYRWMCLRRFIIFLFILLLCLIFLLVLLDYRGMLPVCPLIPGSSTTSTGPCKTCMTT
AQGTSMYPSCCCTKPSDGNCTCIPIPSSWAFAKFLWEWASARFSWLSLLVPFVQWFVGL
SPTVWLSVIWMMWYWGPSLFSILSPFLPLLPIFFCLWVYI

Figure 13

6106 nucleic acid sequence (SEQ ID NO:19)

ATGCAGTGGAATTCCACAACCTTCCACCAAACTCTGCAAGATCCCAGAGTGAGAGG
CCTGTATTTCCCTGCTGGTGGCTCCAGTTCAGGAACAGTAAACCCTGTTCTGACTACT
GCCTCTCCCTTATCGTCAATCTTCTCGAGGATTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCGCAGAGTCTAGACTCGTTGTGGACTTCTCTCAGTT
TTCCAGGGGGCATACCAGAGTGCACTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTACTTCCAGGATCCTCAACAACCAGCA
CGGGACCCTGCAGGACCTGTATGACTACCGCTCAAGGAACCTCTATGTATCCCTCAT
GTTGCTGTACCAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATCATCTGGTATTGGGGGCCAAATCTGTACAACATCTTGAATCCATTTATA
CCGCTGTTACCAATTTTCTTTTGTCTTTGGGTATACATTTAA 6106 amino acid sequence (SEQ ID NO:20)

MQWNSTTFHQTLQDPRVRGLYFPAGGSSSGTVNPVLTTASPLSSIFSRIGDPALNMENIT
SGFLGPLLVLQAGFFLLTRILTIPQSLDSLWTSLSFPGGIPECTGQNSQSPTSNHSPTSCPPT
CPGYRWMCLRRFIIFLFILLLCLIFLLVLLDYRGMLPVCPLLPGSSTTSTGPCRTCMTTAQ
GTSMYPSCCCTKPSDGNCTCIPIPSSWAFAKFLWEWASARFSWLSLLVPFVQWFVGLSP
TVWLSVIWIIWYWGPNLYNILNPFIPLLPIFFCLWVYI

Figure 14

6107 nucleic acid sequence (SEQ ID NO:21)

ATGCAGTGGAATTCCACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCCCTTATCGTCAATCTTCTCGACGACTGGGGACCCTGCACCGAACATGGAG
AACATCACATCAGGATTCCTAGGACCCCTTCTCGTGTTACAGGCGGGGTTTTTCTTGT
TGACAAGAATCCTCACAATACCGCAGAGTCTAGACTCGTGGTGGACTTCTCTCAATT
TTCTAGGGGGAGCACCCGTGTGTCTTGGCCAAAATTCGCAGTCCCCAACCTCCAATC
ACTCACCAACCTCTTGTCCTCCAACTTGTCCTGGGTATCGCTGGATGCGTCTGCGGC
GTTTTATCATCTTCCTCTTCATCCTGCTGCTATGCCTCATCTTCTTGTTGGTTCTTCTG
GACTATCGAGGTATGTTGCCCGTTTGTCCTCTAATTCCAGGATCCTCAACAACCGGC
ACGGGACCCTGCAGGACCTGTATGACTACTGCTCAAGGAACCTCTATGTATCCCTCA
TGTTGTTGTACAAAACCTTCGGACGGAAATTGCACTTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGTGGTTCGTAGGGCTTTCCCCCGCTGTATGGCTTTCAGT
TATATGGATGATGTGGTATTGGGGGCCAAGTCTGTACAGCATCTTGAGTCCCTTTTT
ACCGCTGTTACCAATTTTCTTTTGGCTTTGGGTATACATTTAA 6107 amino acid sequence (SEQ ID NO:22)

MQWNSTAFHQTLQDPRVRGLYLPAGGSSSGTVNPAPNIASPLSSIFSTTGDPAPNMENIT
SGFLGPLLVLQAGFFLLTRILTIPQSLDSWWTSLNFLGGAPVCLGQNSQSPTSNHSPTSCP
PTCPGYRWMRLRRFIIFLFILLLCLIFLLVLLDYRGMLPVCPLIPGSSTTGTGPCRTCMTTA
QGTSMYPSCCCTKPSDGNCTCIPIPSSWAFGKFLWEWASARFSWLSLLVPFVQWFVGLS
PAVWLSVIWMMWYWGPSLYSILSPFLPLLPIFFWLWVYI

Figure 15

6108 nucleic acid sequence (SEQ ID NO:23)

ATGCAGTGGAATTCTACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGTGACGAACATGTCA
CCATCAAGTCTCCTAGGACTCCTCGCAGGATTACAGGTGGTGTATTTCTTGTGGACA
AAAATCCTAACAATACCGCAGAGTCTAGACTCGTGGTGGACTTCTCTCAATTTTCTA
GGGGGAGCACCCGTGTGTCCTGGCCAAAATTCGCAGTCCCCAACCTCCAATCACTCA
CCAACCTCTTGTCCTCCAATTTGTCCTGGTTATCGCTGGATGTGTCTGCGGCGTTTTA
TCATCTTCCTCTTCATCCTGCTTCTATGCCTCATCTTCTTGTTGGTTCTTCTGGACTAT
CAAGGTATGTTGCCCGTTTGTCCTCTAATTCCAGGATCATCGACCACCAGCACGGGA
CCATGCAAAACCTGTATGACTACCCCTCAAGGAACCTCTATGTATCCCTCATGTTGTT
GTACCAAACCTTCGGACGGAAATTGCACCTGTATTCCCATCCCATCATCCTGGGCTT
TCGGAAAATTCCTATGGGAGTGGGCCTCAGTCCGTTTCTCCTGGCTCAGTTTACTAG
CTCCATTTGTTCAGCGGTTCGTAGGGCTTTCCCCCACTGTTTGGCTTTCAGTTATATG
GATGATGTGGTTCTGGGGGCCAAGTCTGTTCAGCATCTTGAGTCCCTTCTTGCCTCTG
TTACCACTTTTCTTTTGGCTTTGGGTATACATTTAA 6108 amino acid sequence (SEQ ID NO:24)

MQWNSTAFHQTLQDPRVRGLYLPAGGSSSGTVNPAPNIASHISSISARTGDPVTNMSPSS
LLGLLAGLQVVYFLWTKILTIPQSLDSWWTSLNFLGGAPVCPGQNSQSPTSNHSPTSCPPI
CPGYRWMCLRRFIIFLFILLLCLIFLLVLLDYQGMLPVCPLIPGSSTTSTGPCKTCMTTPQG
TSMYPSCCCTKPSDGNCTCIPIPSSWAFGKFLWEWASVRFSWLSLLAPFVQRFVGLSPTV
WLSVIWMMWFWGPSLFSILSPFLPLLPLFFWLWVYI

Figure 16

6109 nucleic acid sequence (SEQ ID NO:25)

ATGCAGTGGAATTCTACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGTGACGAACATGTCA
CCATCAAGTCTCCTAGGACTCCTCGCAGGATTACAGGTGGTGTATTTCTTGTGGACA
AAAATCCTAACAATACCGCAGAGTCTAGACTCGTGGTGGACTTCTCTCAATTTTCTA
GGGGGAGCACCCGTGTGTCCTGGCCAAAATTCGCAGTCCCCAACCTCCAATCACTCA
CCAACCTCTTGTCCTCCAATTTGTCCTGGTTATCGCTGGATGTGTCTGCGGCGTTTTA
TCATCTTCCTCTTCATCCTGCTTCTATGCCTCATCTTCTTGTTGGTTCTTCTGGACTAT
CAAGGTATGTTGCCCGTTTGTCCTCTAATTCCAGGATCATCGACCACCAGCACGGGA
CCATGCAAAACCTGTATGACTACCCCTCAAGGAACCTCTATGTATCCCTCATGTTGTT
GTACCAAACCTTCGGACGGAAATTGCACCTGTATTCCCATCCCATCATCCTGGGCTT
TCGGAAAATTCCTATGGGAGTGGGCCTCAGTCCGTTTCTCCTGGCTCAGTTTACTAG
CTCCATTTGTTCAGCGGTTCGTAGGGCTTTCCCCCACTGTTTGGCTTTCAGTTATATG
GATGATGTGGTTCTGGGGGCCAAGTCTGTTCAGCATCTTGAGTCCCTTCTTGCCTCTG
TTACCACTTTTCTTTTGGCTTTGGGTATACATTTAA 6109 amino acid sequence (SEQ ID NO:26)

MQWNSTAFHQTLQDPRVRGLYLPAGGSSSGTVNPAPNIASHISSISARTGDPVTNMSPSS
LLGLLAGLQVVYFLWTKILTIPQSLDSWWTSLNFLGGAPVCPGQNSQSPTSNHSPTSCPPI
CPGYRWMCLRRFIIFLFILLLCLIFLLVLLDYQGMLPVCPLIPGSSTTSTGPCKTCMTTPQG
TSMYPSCCCTKPSDGNCTCIPIPSSWAFGKFLWEWASVRFSWLSLLAPFVQRFVGLSPTV
WLSVIWMMWFWGPSLFSILSPFLPLLPLFFWLWVYI

Figure 17

6111 nucleic acid sequence (SEQ ID NO:27)

ATGCAGTGGAATTCCACTGCCTTCCACCAAACTCTGCAAGATCCCAGAGTACGGGGC
CTATACTTTCCTGTTGGTGGCTCCAGTTCAGGAACAGTAAACCCTGCTCCGAATATT
GCCTCTCCCTTATCGTCAATCTTCTCGAGGATTGGGGACCCTGCGCTGAACATGGAG
AACATCACATCAGGATTCCTAGGACCCCTGCTCGTGTTACAGGCGGGGTTTTTCTTG
TTGACAAAAGTCCTCACAATACCGCAGAGCCTAGACTCGTGGTGGACTTCTCTCAAT
TTTCTAGGGGGAACTACCGTGTGTCTTGGCCAAAATTCGCAGTCCCCAACCTCCAAT
CACTCACCAACCTCTTGTCCTCCAACTTGTCCTGGTTATCGCTGGATGTGTCTGCGGC
GTTTTATCATCTTCCTCTTCATCCTGCTGCTATGCCTCATCTTCTTGTTGGTTCTTCTG
GACTATCGAGGTATGTTGCCCGTTTGTCCTCTAATTCCAGGATCCTCAACAACCAGC
ACGGGACCCTGCAGGACCTGTATGACTACCGCTCAAGGAACCTCTATGTATCCCTCA
TGTTGTTGTACAAAACCTTCGGACGGAAATTGCACTTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGTGGTTCGTAGGGCTTTCCCCCACTGCTTGGCTTTTAGC
TATATGGATCATCTGGTATTGGGGGCCAAATCTGTACAACATCTTGAATCCATTTAT
ACCGCTGTTACCAATTTTCTTTTGTCTTTGGGTATACATTTAA 6111 amino acid sequence (SEQ ID NO:28)

MQWNSTAFHQTLQDPRVRGLYFPVGGSSSGTVNPAPNIASPLSSIFSRIGDPALNMENITS
GFLGPLLVLQAGFFLLTKVLTIPQSLDSWWTSLNFLGGTTVCLGQNSQSPTSNHSPTSCP
PTCPGYRWMCLRRFIIFLFILLLCLIFLLVLLDYRGMLPVCPLIPGSSTTSTGPCRTCMTTA
QGTSMYPSCCCTKPSDGNCTCIPIPSSWAFGKFLWEWASARFSWLSLLVPFVQWFVGLS
PTAWLLAIWIIWYWGPNLYNILNPFIPLLPIFFCLWVYI

Figure 18

6201 nucleic acid sequence (SEQ ID NO:29)

ATGCAGTGGAATTCCACTGCCTTCCACCAAACTCTGCAGGATCCCAGAGTCAGGGGT
CTGTATCTTCCTGCTGGTGGCTCCAGCTCAGGAACAGTAAACCCTGCTCCGAATATT
GCCTCTCACATCTCGTCAATCTCCGCGAGGATTGGGGACCCTGCGCTGAACATGGGG
AACATCACATCAGGATTCCTAGGACCCCTTCTCGTGTTACAGGCGGGGTTTTTCTTG
ATGACAAAAATCCTCACAATGCCGCAGAGTCTAGACTCGTGGTGGACTTCTCTCAAT
TTTCTAGGGGGAACTACCGTGCGTCCTGGCCAAAATTCGCAGTCCCCAACCTCCAAT
CACTCACCAACCTCTTGTCCTCCAACTTGTCCTGGTTATCGCTGGATGTGTCTGCGGC
GTTTTATCATCTTCCTCTTCATCCTGCTGCTATGCCTCATCTTCTTGTTGGTTCTTCTG
GACTATCGAGGTATGTTGCCCGTTTGTCCTCTACTTCCAGGGTCCTCAACAACCAGC
ACGGGACCCTGCAGGACCTGTATGACTACCGCTCAAGGAACCTCTATGTATCCCTCA
TGTTGCTGTACCAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATCATCTGGTATTGGGGGCCAAATCTGTACAACATCTTGAATCCATTTATA
CCGCTGTTACCAATTTTCTTTTGTCTTTGGGTATACATTTAA 6201 amino acid sequence (SEQ ID NO:30)

MQWNSTAFHQTLQDPRVRGLYLPAGGSSSGTVNPAPNIASHISSISARIGDPALNMGNIT
SGFLGPLLVLQAGFFLMTKILTMPQSLDSWWTSLNFLGGTTVRPGQNSQSPTSNHSPTSC
PPTCPGYRWMCLRRFIIFLFILLLCLIFLLVLLDYRGMLPVCPLLPGSSTTSTGPCRTCMTT
AQGTSMYPSCCCTKPSDGNCTCIPIPSSWAFAKFLWEWASARFSWLSLLVPFVQWFVGL
SPTVWLSVIWIIWYWGPNLYNILNPFIPLLPIFFCLWVYI

Figure 19

6202 nucleic acid sequence (SEQ ID NO:31)

ATGCAGTGGAATTCCACTGCCTTCCACCAAACTCTGCAGGATCCCAGAGTCAGGGGT
CTGTATCTTCCTGCTGGTGGCTCCAGCTCAGGAACAGTAAACCCTGCTCCGAATATT
GCCTCTCACATCTCGTCAATCTCCGCGAGGATTAGGGACCCTGCGCTGAACATGGAG
AACATCGCATCAGGATTCCTAGGACCCCTTCTCGCATTACAGGCGGTGTTTTTCTTGT
TGACAAAAATCCTCACAATGCCACAGAGTCTAGACTCGTGGTGGACTTCTCTCAATT
TTCTAGGGGGAACTACCGTGTGTCTTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTAATTCCAGGATCCTCAACAACCAGCA
CGGGACCATGCAAAACCTGTATGACTACCGCTCAAGGAACCTCTATGTATCCCTCAT
GTTGTTGTACAAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATGATGTGGTATTGGGGACCAAGTCTGTACAGCATCTTGAGTCCCTTCTTG
CCTCTGTTACCACTTTTCTTTTGGCTTTGGGTATACATTTAA 6202 amino acid sequence (SEQ ID NO:32)

MQWNSTAFHQTLQDPRVRGLYLPAGGSSSGTVNPAPNIASHISSISARIRDPALNMENIA
SGFLGPLLALQAVFFLLTKILTMPQSLDSWWTSLNFLGGTTVCLGQNSQSPTSNHSPTSC
PPTCPGYRWMCLRRFIIFLFILLLCLIFLLVLLDYRGMLPVCPLIPGSSTTSTGPCKTCMTT
AQGTSMYPSCCCTKPSDGNCTCIPIPSSWAFAKFLWEWASARFSWLSLLVPFVQWFVGL
SPTVWLSVIWMMWYWGPSLYSILSPFLPLLPLFFWLWVYI

Figure 20

6203 nucleic acid sequence (SEQ ID NO:33)

ATGCAGTGGAATTCTACAACCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCACAGAGTCTAGACTCGTGGTGGACTTCTCTCAATT
TTCTAGGGGGAGCACCCGTGTGTCCTGGCCAAAATTCGCAGTCCCCAACCTCCAATC
ACTCACCAACCTCTTGTCCTCCGATTTGTCCTGGCTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTACTTCCAGGATCCTCAACAACCAGCA
CGGGACCATGCCGGACCTGCATGACTACCGCTCAAGGAACCTCTATGTATCCCTCAT
GTTGCTGTACCAAACCTTCGGACGGAAGCTGCACTTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCGCTGTATGGCTTTCAGTT
ATATGGATGATTTGGTTTTGGGGGCCAAGTCTGTACAGCATCTTGAGTCCCTTTTTAC
CGCTGTTACCAATTTTCTTTGTCTTTGGGTATACATTTAA 6203 amino acid sequence (SEQ ID NO:34)

MQWNSTTFHQTLQDPRVRGLYLPAGGSSSGTVNPAPNIASHISSISARTGDPALNMENIT
SGFLGPLLVLQAGFFLLTRILTIPQSLDSWWTSLNFLGGTTVCLGLNSQSPTSNHSPTSCP
PTCPGYRWMCLRRFIIFLFILLLCLIFLLVLLDYQGMLPVCPLIPGSSTTSTGPCKTCMTTP
QGTSMYPSCCCTKPSDGNCTCIPIPSSWAFGKFLWEWASARFSWLSLLVPFVQWFVGLS
PTAWLLAIWIIWYWGPNLYNILNPFLPLLPIFFCLWVYI

Figure 21

6204 nucleic acid sequence (SEQ ID NO:35)

ATGCAGTGGAATTCTACAACCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCACAGAGTCTAGACTCGTGGTGGACTTCTCTCAATT
TTCTAGGGGGAACTACCGTGTGTCTTGGCCTAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTTCTATGCCTCATCTTCTTGTTGGTTCTTCTGG
ACTATCAAGGTATGTTGCCCGTTTGTCCCCTAATTCCAGGATCCTCAACAACCAGCA
CGGGACCATGCAAAACCTGTATGACTACCCCTCAAGGAACCTCTATGTATCCCTCAT
GTTGCTGTACCAAACCTTCGGACGGAAATTGCACCTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGTGGTTCGTAGGGCTTTCCCCCACTGCTTGGCTTTTGGC
TATATGGATCATCTGGTATTGGGGGCCAAATCTGTACAACATCTTGAATCCCTTTTTA
CCGCTGTTACCAATTTTCTTTTGTCTTTGGGTATACATTTAA 6204 amino acid sequence (SEQ ID NO:36)

MQWNSTTFHQTLQDPRVRGLYLPAGGSSSGTVNPAPNIASHISSISARTGDPALNMENIT
SGFLGPLLVLQAGFFLLTRILTIPQSLDSWWTSLNFLGGTTVCLGLNSQSPTSNHSPTSCP
PTCPGYRWMCLRRFIIFLFILLLCLIFLLVLLDYQGMLPVCPLIPGSSTTSTGPCKTCMTTP
QGTSMYPSCCCTKPSDGNCTCIPIPSSWAFGKFLWEWASARFSWLSLLVPFVQWFVGLS
PTAWLLAIWIIWYWGPNLYNILNPFLPLLPIFFCLWVYI

Figure 22

6205 nucleic acid sequence (SEQ ID NO:37)

ATGCAGTGGAATTCCACAACCTTCCACCAAACTCTGCAGGATCCCAGAGTCAGGGG
TCTGTATCTTCCTGCTGGTGGCTCCAGTTCAGGAACAGTAAACCCTGCTCCGAATAC
TGCCTCTCACATCTCGTCAGTCTTCTCGACGACTGGGGACCCTGCACCGAACATGGA
GAACATCACATCAGGATTCCTAGGACCCCTGCTCGTGTTACAGGCGGGGTTTTTCTT
GTTGACAAAAATCCTCACAATGCCACAGAGTCTAGACTCGTTGTGGACTTCTCTCAA
TTTTCTAGGGGGAACACCAGCGTGTCTTGGCCAAAATTCGCAGTCCCCAACCCCCAA
TCACTCACCAACCTCTTGCCCTCCAACTTGTCCTGGTTATCGCTGGATGTGTCTGCGG
CGTTTTATCATCTTCCTCTTCATCCTGCTTCTATGCCTCATCTTCTTGTTGGTTCTTCTG
GACTATCGAGGTATGTTGCCCGTTTGTCCTCTAATTCCAGGATCCTCAACAACCAGC
ACGGGACCATGCAAAACCTGTATGACTACCCCTCAAGGAACCTCTATGTATCCCTCA
TGTTGCTGTACCAAACCTTCGGACGGAAATTGCACCTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGTGGTTCGTAGGGCTTTCCCCCACTGCTTGGCTTTTGGC
TATATGGATCATCTGGTATTGGGGGCCAAATCTGTACAACATCTTGAATCCCTTTTTA
CCGCTGTTACCAATTTTCTTTTGTCTTTGGGTATACATTTAA 6205 amino acid sequence (SEQ ID NO:38)

MQWNSTTFHQTLQDPRVRGLYLPAGGSSSGTVNPAPNTASHISSVFSTTGDPAPNMENI
TSGFLGPLLVLQAGFFLLTKILTMPQSLDSLWTSLNFLGGTPACLGQNSQSPTPNHSPTSC
PPTCPGYRWMCLRRFIIFLFILLLCLIFLLVLLDYRGMLPVCPLIPGSSTTSTGPCKTCMTT
PQGTSMYPSCCCTKPSDGNCTCIPIPSSWAFGKFLWEWASARFSWLSLLVPFVQWFVGL
SPTAWLLAIWIIWYWGPNLYNILNPFLPLLPIFFCLWVYI

Figure 23

6206 nucleic acid sequence (SEQ ID NO:39)

ATGCAGTGGAATTCCACTGCCTTCCACCAAACTCTGCAGGATCCCAGAGTCAGGGGT
CTGTATCTCCCTGCTGGTGGCTCCAGTTCAGGAACAGTAAACCCTGCTCCGAATATT
GCCTCTCACATCTCGTCAATCTCCGCGAGGACTGGGGACCCTGCACCGAACATGGAG
AACATCACATCAGGATTCCTAGGACCCCTGCTCGTGTTACAGGCGGTGTTTTTCTTGT
TGACAAGAATCCTCACAATACCGCAGAGTCTAGACTCGTGGTGGACTTCTCTCAATT
TTCTAGGGGAACACCCGTGTGTCCTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTTCTATGCCTCATCTTCTTGTTGGTTCTTCTGG
ACTATCAAGGTATGTTGCCCGTTTGTCCCCTAATTCCAGGATCCTCAACAACCAGCA
CGGGACCATGCAAAACCTGTATGACTACCCCTCAAGGAACCTCTATGTATCCCTCAT
GTTGCTGTACCAAACCTTCGGACGGAAATTGCACCTGTATTCCCATCCCATCATCCT
GGGCTTTCGGAAAATTCCTATGGGAGTGGGCCTCAGCCCGTTTCTCCTGGCTCAGTT
TACTAGTGCCATTTGTTCAGCGGTTCGCAGGGCTTTCCCCCACTGTTTGGCTTTCAGT
TATATGGATGATTTGGTTTTGGGGGCCAAGTCTGTACAGCATCTTGAGTCCCTTTTA
CCGCTGTTACCAATTTTCTTTTGTCTTTGGGTATACATTTAA 6206 amino acid sequence (SEQ ID NO:40)

MQWNSTAFHQTLQDPRVRGLYLPAGGSSSGTVNPAPNIASHISSISARTGDPAPNMENIT
SGFLGPLLVLQAVFFLLTRILTIPQSLDSWWTSLNFLGGTPVCPGQNSQSPTSNHSPTSCP
PTCPGYRWMCLRRFIIFLFILLLCLIFLLVLLDYQGMLPVCPLIPGSSTTSTGPCKTCMTTP
QGTSMYPSCCCTKPSDGNCTCIPIPSSWAFGKFLWEWASARFSWLSLLVPFVQRFAGLSP
TVWLSVIWMIWFWGPSLYSILSPFLPLLPIFFCLWVYI

Figure 24

6207 nucleic acid sequence (SEQ ID NO:41)

ATGCAGTGGAATTCCACAACCTTCCACCAAACTCTGCAAGATCCCAGAGTGAGAGG
CCTGTATTTCCCTGCTGGTGGCTCCAGTTCAGGAACAGTAAACCCTGTTCTGACTACT
GCCTCTCCCGTATCGTCAATCTTCTCGAGGATTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCGCAGAGTCTAGACTCGTTGTGGACTTCTCTCAGTT
TTCCAAGGGGCATACCAGAGTGCACTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTACTTCCAGGATCCTCAACAACCAGCA
CGGGACCCTGCAGGACCTGTATGACTACCGCTCAAGGAACCTCTATGTATCCCTCAT
GTTGCTGTACCAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATCATCTGGTATTGGGGGCCAAATCTGTACAACATCTTGAATCCATTTATA
CCGCTGTTACCAATTTTCTTTTGTCTTTGGGTATACATTTAA 6207 amino acid sequence (SEQ ID NO:42)

MQWNSTTFHQTLQDPRVRGLYFPAGGSSSGTVNPVLTTASPVSSIFSRIGDPALNMENIT
SGFLGPLLVLQAGFFLLTRILTIPQSLDSLWTSLSFPRGIPECTGQNSQSPTSNHSPTSCPPT
CPGYRWMCLRRFIIFLFILLLCLIFLLVLLDYRGMLPVCPLLPGSSTTSTGPCRTCMTTAQ
GTSMYPSCCCTKPSDGNCTCIPIPSSWAFAKFLWEWASARFSWLSLLVPFVQWFVGLSP
TVWLSVIWIIWYWGPNLYNILNPFIPLLPIFFCLWVYI

Figure 25

6208 nucleic acid sequence (SEQ ID NO:43)

ATGCAGTGGAATTCCACAACCTTCCACCAAACTCTGCAAGATCCCAGAGTGAGAGG
CCTGTATTTCCCTGCTGGTGGCTCCAGTTCAGGAACAGTAAACCCTGTTCTGACTACT
GCCTCTCCCTTATCGTCAATCTTCTCGAGGATTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCGCAGAGTCTAGACTCGTTGTGGACCTCTCTCAGTT
TTCCAGGGGGCATACCAGAGTGCACTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTACTTCCAGGATCCTCAACAACCAGCA
CGGGACCCTGCAGGACCTGTATGACTACCGCTCAAGGAACCTCTATGTATCCCTCAT
GTTGCTGTACCAAACCTTCGGACGGAAATTGCACCTGTATTCCCATCCCATCATCCT
GGGCTTTCGGAAAATTCCTATGGGAGTGGGCCTCAGTCCGTTTCTCCTGGCTCAGTTT
ACTAGCTCCATTTGTTCAGCGGTTCGTAGGGCTTTCCCCCACTGTTTGGCTTTCAGTT
ATATGGATGATGTGGTTCTGGGGGCCAAGTCTGTTCAGCATCTTGAGTCCCTTCTTGC
CTCTGTTACCACTTTTCTTTTGGCTTTGGGTATACATTTAA 6208 amino acid sequence (SEQ ID NO:44)

MQWNSTTFHQTLQDPRVRGLYFPAGGSSSGTVNPVLTTASPLSSIFSRIGDPALNMENIT
SGFLGPLLVLQAGFFLLTRILTIPQSLDSLWTSLSFPGGIPECTGQNSQSPTSNHSPTSCPPT
CPGYRWMCLRRFIIFLFILLLCLIFLLVLLDYRGMLPVCPLLPGSSTTSTGPCRTCMTTAQ
GTSMYPSCCCTKPSDGNCTCIPIPSSWAFGKFLWEWASVRFSWLSLLAPFVQRFVGLSPT
VWLSVIWMMWFWGPSLFSILSPFLPLLPLFFWLWVYI

Figure 26

6209 nucleic acid sequence (SEQ ID NO:45)

ATGCAGTGGAATTCCACTGCCTTCCACCAAACTCTGCAGGATCCCAGAGTCAGGGGT
CTGTATCTTCCTGCTGGTGGCTCCAGCTCAGGAACAGTAAACCCTGCTCCGAATATT
GCCTCTCACATCTCGTCAATCTCCGCGAGGATTGGGGACCCTGCGCTGAACATGGAG
AACATCACATCAGGATTCCTAGGACCCCTTCTCGCATTACAGGCGGTGTTTTTCTTGT
TGACAAAAATCCTCACAATGCCACAGAGTCTAGACTCGTGGTGGACTTCTCTCAATT
TTCTAGGGGGAACTACCGTGTGTCTTGGCCTAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTGTGCCTCATCTTCTTGTTGGTTCTTCTGG
ACTATCGAGGTATGTTGCCCGTTTGTCCTCTACTTCCAGGATCCTCAACAACCAGCA
CGGGACCATGCCGGACCTGCATGACTACCGCTCAAGGAACCTCTATGTATCCCTCAT
GTTGCTGTACCAAACCTTCGGACGGAAGCTGCACTTGTATTCCCATCCCCTCATCCT
GGGCTTTCGGAAAATTCCTATGGGAGTGGGCCTCAGTCCGTTTCTCCTGGCTCAGTTT
ACTAGTGCCATTTGTTCAGTGGTTCGCAGGGCTTTCCCCCACTGTATGGCTTTTAGTT
ATATGGATGATGTGGTTCTGGGGGCCAAGTCTGTTCAGCATCTTGAGTCCCTTCTTGC
CTCTGTTACCAATTTTCTTTGTCTTTGGGTATACATTTAA 6209 amino acid sequence (SEQ ID NO:46)

MQWNSTAFHQTLQDPRVRGLYLPAGGSSSGTVNPAPNIASHISSISARIGDPALNMENIT
SGFLGPLLALQAVFFLLTKILTMPQSLDSWWTSLNFLGGTTVCLGLNSQSPTSNHSPTSC
PPTCPGYRWMCLRRFIIFLFILLLCLIFLLVLLDYRGMLPVCPLLGSSTTSTGPCRTCMTT
AQGTSMYPSCCCTKPSDGSCTCIPIPSSWAFGKFLWEWASVRFSWLSLLVPFVQWFAGL
SPTVWLLVIWMMWFWGPSLFSILSPFLPLLPIFFCLWVYI

Figure 27

6210 nucleic acid sequence (SEQ ID NO:47)

ATGCAGTGGAATTCCACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCCCTTATCGTCAATCTTCTCGACGACTGGGGACCCTGCGCTGAACATGGAG
AACATCACATCAGGATTCCTAGGACCCCTTCTCGTGTTACAGGCGGGGTTTTTCTTGT
TGACAAGAATCCTCACAATACCGCAGAGTCTAGACTCGTGGTGGACTTCTCTCAATT
TTCTAGGGGGAGCACCCGTGTGTCTTGGCCAAAATTCGCAGTCCCCAACCTCCAATC
ACTCACCAACCTCTTGTCCTCCAACTTGTCCTGGTTATCGCTGGATGTGTCTGCGGCG
TTTTATCATCTTCCTCTTCATCCTGCTGCTATGCCTCATCTTCTTGTTGGTTCTTCTGG
ACTATCGAGGTATGTTGCCCGTTTGTCCTCTAATTCCAGGATCCTCAACAACCAGCA
CGGGACCCTGCAGGACCTGTATGACTGCCGCTCAAGGAACCTCTATGTATCCCTCAT
GTTGCTGTACCAAACCTTCGGACGGAAATTGCACCTGTATTCCCATCCCATCATCCT
GGGCTTTCGCAAAATTCCTATGGGAGTGGGCCTCAGCCCGTTTCTCCTGGCTCAGTTT
ACTAGTGCCATTTGTTCAGTGGTTCGTAGGGCTTTCCCCCACTGTTTGGCTTTCAGTT
ATATGGATCATCTGGTATTGGGGGCCAAATCTGTACAACATCTTGAATCCATTTATA
CCGCTGTTACCAATTTTCTTTTGTCTTTGGGTATACATTTAA 6210 amino acid sequence (SEQ ID NO:48)

MQWNSTAFHQTLQDPRVRGLYLPAGGSSSGTVNPAPNIASPLSSIFSTTGDPALNMENIT
SGFLGPLLVLQAGFFLLTRILTIPQSLDSWWTSLNFLGGAPVCLGQNSQSPTSNHSPTSCP
PTCPGYRWMCLRRFIIFLFILLLCLIFLLVLLDYRGMLPVCPLIPGSSTTSTGPCRTCMTAA
QGTSMYPSCCCTKPSDGNCTCIPIPSSWAFAKFLWEWASARFSWLSLLVPFVQWFVGLS
PTVWLSVIWIIWYWGPNLYNILNPFIPLLPIFFCLWVYI

Figure 28

6211 nucleic acid sequence (SEQ ID NO:49)

ATGCAGTGGAATTCCACAACCTTCCACCAAACTCTGCAGGATCCCAGAGTCAGGGG
TCTGTATCTTCCTGCTGGTGGCTCCAGTTCAGGAACAGTAAACCCTGCTCCGAATAC
TGCCTCTCACATCTCGTCAGTCTTCTCGACGACTGGGGACCCTGCACCGAACATGGA
GAACATCACATCAGGATTCCTAGGACCCCTGCTCGTGTTACAGGCGGGGTTTTCTT
GTTGACAAAAATCCTCACAATGCCACAGAGTCTAGACTCGTTGTGGACTTCTCTCAA
TTTTCTAGGGGGAACACCAGCGTGTCTTGGCCAAAATTCGCAGTCCCCAACCTCCAA
TCACTCACCAACCTCTTGTCCTCCAACTTGTCCTGGTCATCGCTGGATGTGTCTGCGG
CGTTTTATCATCTTCCTCTTCATCCTGCTGCTATGCCTCATCTTCTTGTTGGTTCTTCT
GGACTATCGAGGTATGTTGCCCGTTTGTCCTCTAATTCCAGGATCCTCAACAACCAG
CACGGGACCATGCAAAACCTGTATGACTACCCCTCAAGGAACCTCTATGTATCCCTC
ATGTTGCTGTACCAAACCTTCGGACGGAAATTGCACCTGTATTCCCATCCCATCATC
CTGGGCTTTCGGAAAATTCCTATGGGAGTGGGCCTCAGCCCGTTTCTCCTGGCTCAG
TTTACTAGTGCCATTTGTTCAGTGGTTCGTAGGGCTTTCCCCCACTGCTTGGCTTTTG
GCTATATGGATCATCTGGTATTGGGGGCCAAATCTGTACAACATCTTGAATCCCTTTT
TACCGCTGTTACCAATTTTCTTTTGTCTTTGGGTATACATTTAA 6211 amino acid sequence (SEQ ID NO:50)

MQWNSTTFHQTLQDPRVRGLYLPAGGSSSGTVNPAPNTASHISSVFSTTGDPAPNMENI
TSGFLGPLLVLQAGFFLLTKILTMPQSLDSLWTSLNFLGGTPACLGQNSQSPTSNHSPTSC
PPTCPGHRWMCLRRFIIFLFILLLCLIFLLVLLDYRGMLPVCPLIPGSSTTSTGPCKTCMTT
PQGTSMYPSCCCTKPSDGNCTCIPIPSSWAFGKFLWEWASARFSWLSLLVPFVQWFVGL
SPTAWLLAIWIIWYWGPNLYNILNPFLPLLPIFFCLWVYI

Figure 29

6212 nucleic acid sequence (SEQ ID NO:51)

ATGCAGTGGAATTCCACAACCTTCCACCAAACTCTGCAGGATCCCAGAGTCAGGGG
TCTGTATCTTCCTGCTGGTGGCTCCAGTTCAGGAACAGTAAACCCTGCTCCGAATAC
TGCCTCTCACATCTCGTCAGTCTTCTCGACGACTGGGGACCCTGCACCGAACATGGA
GAACATCACATCAGGATTCCTAGGACCCCTGCTCGTGTTACAGGCGGGGTTTTTCTT
GTTGACAAAAATCCTCACAATGCCACAGAGTCTAGACTCGTTGTGGACTTCTCTCAA
TTTTCTAGGGGGAACACCAGCGTGTCTTGGCCAAAATTCGCAGTCCCCAACCTCCAA
TCACTCACCAACCTCTTGTCCTCCAACTTGTCCTGGTCATCGCTGGATGTGTCTGCGG
CGTTTTATCATCTTCCTCTTCATCCTGCTGCTATGCCTCATCTTCTTGTTGGTTCTTCT
GGACTATCGAGGTATGTTGCCCGTTTGTCCTCTAATTCCAGGATCCTCAACAACCAG
CACGGGACCATGCAAAACCTGTATGACTACCCCTCAAGGAACCTCTATGTATCCCTC
ATGTTGCTGTACCAAACCTTCGGACGGAAATTGCACCTGTATTCCCATCCCATCATC
CTGGGCTTTCGGAAAATTCCTATGGGAGTGGGCCTCAGCCCGTTTCTCCTGGCTCAG
TTTACTAGTGCCATTTGTTCAGTGGTTCGTAGGGCTTTCCCCCACTGCTTGGCTTTTG
GCTATATGGATCATCTGGTATTGGGGGCCAAATCTGTACAACATCTTGAATCCCTTTT
TACCGCTGTTACCAATTTTCTTTTGTCTTTGGGTATACATTTAA 6212 amino acid sequence (SEQ ID NO:52)

MQWNSTAFHQTLQDPRVRGLYLPAGGSSSGTVNPAPNIASHISSISARIGDPALNMENIT
SGFLGPLLALQAVFFLLTKILTMPQSLDSWWTSLNFLGGTTVCLGQNSQSPTSNHSPTSC
PPTCPGYRWMCLRRFIIFLFILLLCLIFLLVLLDYRGMLPVCPLIPGSSTTSGPCKTCMTT
AQGTSMYPSCCCTKPSDGNCTCIPIPSSWAFGKFLWEWASARFSWLSLLAPFVQRFAGL
SPTAWLLAIWIIWYWGPNLYNIMNPFLPLLPIFFCLWVYI

Figure 30

6213 nucleic acid sequence (SEQ ID NO:53)

ATGCAGTGGAATTCCACTGCCTTCCACCAAACTCTGCAGGATCCCAGAGTCAGGGGT
CTGTATCTTCCTGCTGGTGGCTCCAGTTCAGGAACAGTAAACCCTGCTCCGAATACT
GCCTCTCACATCTCGTCAGTCTTCTCGACGACTGGGGACCCTGCACCGAACATGGAG
AACATCACATCAGGATTCCTAGGACCCCTGCTCGTGTTACAGGCGGGGTTTTCTTG
TTGACAAAAATCCTCACAATGCCACAGAGTCTAGACTCGTTGTGGACTTCTCTCAAT
TTTCTAGGGGGAACACCAGCGTGTCTTGGCCAAAATTCGCAGTCCCCAACCTCCAAT
CACTCACCAACCTCTTGTCCTCCAACTTGTCCTGGTTATCACTGGATGTGTCTGCGGC
GTTTTATCATCTTCCTCTTCATCCTGCTGCTATGCCTCATCTTCTTGTTGGTTCTTCTG
GACTATCGAGGTATGTTGCCCGTTTGTCCTCTACTTCCAGGATCATCGACCACCAGC
ACGGGACCATGCAAAACCTGCACGATCCCTGCTCAAGGAACCTCTTTGATTCCCTCA
TGTTGTTGTACAAAACCTTCGGACGGAAATTGCACTTGTATTCCCATCCCATCGTCTT
GGGCTTTCGCAAAATTCCTATGGGAGTGGGCCTCAGCCCGTTTCTCCTGGCTCAGTTT
ACTAGTGCCATTTGTTCAGCGGTTCGCAGGGCTTTCCCCCACTGTTTGGCTTTCAGTT
ATATGGATGATTTGGTTTTGGGGGCCAAGTCTGTACAGCATCTTGAGTCCCTTTTTAC
CGCTGTTACCAATTTTCTTTTGTCTTTGGGTATACATTTAA 6213 amino acid sequence (SEQ ID NO:54)

MQWNSTAFHQTLQDPRVRGLYLPAGGSSSGTVNPAPNTASHISSVFSTTGDPAPNMENI
TSGFLGPLLVLQAGFFLLTKILTMPQSLDSLWTSLNFLGGTPACLGQNSQSPTSNHSPTSC
PPTCPGYHWMCLRRFIIFLFILLLCLIFLLVLLDYRGMLPVCPLLPGSSTTSTGPCKTCTIP
AQGTSLIPSCCCTKPSDGNCTCIPIPSSWAFAKFLWEWASARFSWLSLLVPFVQRFAGLSP
TVWLSVIWMIWFWGPSLYSILSPFLPLLPIFFCLWVYI

Figure 31

6214 nucleic acid sequence (SEQ ID NO:55)

ATGCAGTGGAATTCTACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGTGACGAACATGTCA
CCATCAAGTCTCCTAGGACTCCTAGCAGGATTACAGGTGGTGTATTTCTTGTGGACA
AAAATCCTAACAATACCGCAGAGTCTAGACTCGTGGTGGACTTCTCTCAATTTTCTA
GGGGGAGCACCCGTGTGTCCTGGCCAAAATTCGCAGCCCCCAACCCCCAATCACTC
ACCAACCTCTTGTCCTTCAACTTGTCCTGGGTATCGCTGGATGCGTCTGTGGCGTTTT
ATCATCTTCCTCTTCATCCTGCTGCTATGCCTCATCTTCTTGTTGGTTCTTCTGGACTA
TCGAGGTGTGTTGCCCGTTTGTCCTCCAATTCCAGGATCCTCAACAACCAGCACGGG
ACCATGCAAAACCTGTATGACTACCGCTCAAGGAACCTCTATGTATCCCTCATGTTG
TTGTACAAAACCTTCGGACGGAAATTGCACCTGTATTCCCATCCCATCATCCTGGGC
TTTCGGAAAATTCCTATGGGAGTGGGCCTCAGCCCGTTTCTCCTGGCTCAGTTTACTA
GTGCCATTTGTTCAGTGGTTCGTAGGGCTTTCCCCCACTGCTTGGCTTTTGGCTACAT
GGATCATCTGGTATTGGGGGCCAAATCTGTACAACATCTTGAATCCCTTTTTACCGCT
GTTACCAATTTTCTTTTGTCTTTGGGTATACATTTAA 6214 amino acid sequence (SEQ ID NO:56)

MQWNSTAFHQTLQDPRVRGLYLPAGGSSSGTVNPAPNIASHISSISARTGDPVTNMSPSS
LLGLLAGLQVVYFLWTKILTIPQSLDSWWTSLNFLGGAPVCPGQNSQPPTPNHSPTSCPS
TCPGYRWMRLWRFIIFLFILLLCLIFLLVLLDYRGVLPVCPPIPGSSTTSTGPCKTCMTTAQ
GTSMYPSCCCTKPSDGNCTCIPIPSSWAFGKFLWEWASARFSWLSLLVPFVQWFVGLSP
TAWLLATWIIWYWGPNLYNILNPFLPLLPIFFCLWVYI

Figure 32

6215 nucleic acid sequence (SEQ ID NO:57)

ATGCAGTGGAATTCTACTGCCTTCCACCAAACTCTGCAGGATCCCAGAGTCAGGGGT
CTGTATCTTCCTGCTGGTGGCTCCAGTTCAGGAACAGTAAACCCTGCTCCGAATATT
GCCTCTCACATCTCGTCAATCTCCGCGAGGACTGGGGACCCTGTGACGAACATGTCA
CCATCAAGTCTCCTAGGACTCCTCGCAGGATTACAGGTGGTGTATTTCTTGTGGACA
AAAATCCTAACAATACCGCAGAGTCTAGACTCGTGGTGGACTTCTCTCAATTTTCTA
GGGGGAGCACCCGTGTGTCCTGGCCAAAATTCGCAGTCCCCAACCTCCAATCACTCA
CCAACCTCTTGTCCTCCAACTTGTCCTGGTTATCGCTGGATGTGTCTGCGGCGTTTTA
TCATCTTCCTCTTCATCCTGCTGCTATGCCTCATCTTCTTGTTGGTTCTTCTGGACTAT
CGAGGTATGTTGCCCGTTTGTCCTCTACTTCCAGGATCCTCAACAACCAGCACGGGA
CCCTGCAGGACCTGTATGACTACCGCTCAAGGAACCTCTATGTATCCCTCATGTTGC
TGTACCAAACCTTCGGACGGAAATTGCACCTGTATTCCCATCCCATCATCCTGGGCT
TTCGCAAAATTCCTATGGGAGTGGGCCTCAGCCCGTTTCTCCTGGCTCAGTTTACTAG
TGCCATTTGTTCAGTGGTTCGTAGGGCTTTCCCCCACTGTTTGGCTTTCAGTTATATG
GATCATCTGGTATTGGGGGCCAAATCTGTACAACATCTTGAGTCCATTTATACCGCT
GTTACCAATTTTCTTTTGTCTTTGGGTATACATTTAA 6215 amino acid sequence (SEQ ID NO:58)

MQWNSTAFHQTLQDPRVRGLYLPAGGSSSGTVNPAPNIASHISSISARTGDPVTNMSPSS
LLGLLAGLQVVYFLWTKILTIPQSLDSWWTSLNFLGGAPVCPGQNSQSPTSNHSPTSCPP
TCPGYRWMCLRRFIIFLFILLLCLIFLLVLLDYRGMLPVCPLLPGSSTTSTGPCRTCMTTA
QGTSMYPSCCCTKPSDGNCTCIPIPSSWAFAKFLWEWASARFSWLSLLVPFVQWFVGLS
PTVWLSVIWIIWYWGPNLYNILSPFIPLLPIFFCLWVYI

```
                              Figure 33
                1         10        20        30        40        50        60
                |         |         |         |         |         |         |
        HBV     ATGCAGTGGAATTCCACAACCTTCCACCAAACTCTGCAAGATCCCAGAGTGAGAGGCCTG
        CGHV    ATGCAGTGGAATTCTACAGTATTCCACCAAGCTCTGCAAGATCCCAGAGTACGGGGCCTA
        HHWHV   ATGCAGTGGAATTCCACTGCCTTCCACCAAACTCTGCAGGATCCCAGAGTCAGGGGTCTG
        WMHV    ATGCAGTGGAATTCCACTTCCTTCCAGAGTTATCTTCAGAATCCAAAGGTCAGAGGCCTC
        6101    ATGCAGTGGAATTCTACAGTATTCCACCAAACTCTGCAAGATCCCAGAGTGCGGGGTCTG
        6102    ATGCAGTGGAATTCCACAACCTTCCACCAAACTCTGCAGGATCCCAGAGTCAGGGGTCTG
        6103    ATGCAGTGGAATTCCACTGCCTTCCACCAAACTCTGCAGGATCCCAGAGTCAGGGGTCTG
        6104    ATGCAGTGGAATTCTACAACCTTCCACCAAACTCTGCAGGATCCCAGAGTCAGGGGTCTG
        6105    ATGCAGTGGAATTCTACAACCTTCCACCAAACTCTGCAGGATCCCAGAGTCAGGGGTCTG
        6106    ATGCAGTGGAATTCCACAACCTTCCACCAAACTCTGCAAGATCCCAGAGTGAGAGGCCTG
        6107    ATGCAGTGGAATTCCACTGCCTTCCACCAAACTCTGCAGGATCCCAGAGTCAGGGGTCTG
        6108    ATGCAGTGGAATTCTACTGCCTTCCACCAAACTCTGCAGGATCCCAGAGTCAGGGGTCTG
        6109    ATGCAGTGGAATTCTACTGCCTTCCACCAAACTCTGCAGGATCCCAGAGTCAGGGGTCTG
        6110    ATGCAGTGGAATTCTACTGCCTTCCACCAAACTCTGCAGGATCCCAGAGTCAGGGGTCTG
        6111    ATGCAGTGGAATTCCACTGCCTTCCACCAAACTCTGCAAGATCCCAGAGTACGGGGCCTA
        6201    ATGCAGTGGAATTCCACTGCCTTCCACCAAACTCTGCAGGATCCCAGAGTCAGGGGTCTG
        6202    ATGCAGTGGAATTCCACTGCCTTCCACCAAACTCTGCAGGATCCCAGAGTCAGGGGTCTG
        6203    ATGCAGTGGAATTCTACAACCTTCCACCAAACTCTGCAGGATCCCAGAGTCAGGGGTCTG
        6204    ATGCAGTGGAATTCTACAACCTTCCACCAAACTCTGCAGGATCCCAGAGTCAGGGGTCTG
        6205    ATGCAGTGGAATTCCACAACCTTCCACCAAACTCTGCAGGATCCCAGAGTCAGGGGTCTG
        6206    ATGCAGTGGAATTCCACTGCCTTCCACCAAACTCTGCAGGATCCCAGAGTCAGGGGTCTG
        6207    ATGCAGTGGAATTCCACAACCTTCCACCAAACTCTGCAAGATCCCAGAGTGAGAGGCCTG
        6208    ATGCAGTGGAATTCCACAACCTTCCACCAAACTCTGCAAGATCCCAGAGTGAGAGGCCTG
        6209    ATGCAGTGGAATTCCACTGCCTTCCACCAAACTCTGCAGGATCCCAGAGTCAGGGGTCTG
        6210    ATGCAGTGGAATTCCACTGCCTTCCACCAAACTCTGCAGGATCCCAGAGTCAGGGGTCTG
        6211    ATGCAGTGGAATTCCACAACCTTCCACCAAACTCTGCAGGATCCCAGAGTCAGGGGTCTG
        6212    ATGCAGTGGAATTCCACTGCCTTCCACCAAACTCTGCAGGATCCCAGAGTCAGGGGTCTG
        6213    ATGCAGTGGAATTCCACTGCCTTCCACCAAACTCTGCAGGATCCCAGAGTCAGGGGTCTG
        6214    ATGCAGTGGAATTCTACTGCCTTCCACCAAACTCTGCAGGATCCCAGAGTCAGGGGTCTG
        6215    ATGCAGTGGAATTCTACTGCCTTCCACCAAACTCTGCAGGATCCCAGAGTCAGGGGTCTG 61        70        80        90        100       110       120
                |         |         |         |         |         |         |
        HBV     TATTCCCTGCTGGTGGCTCCAGTTCAGGAACAGTAAACCCTGTTCTGACTACTGCCTCT
        CGHV    TACTTTCCTGTTGGTGGCTCCAGTTCAGGAACATTGAACCCTGTTCCGAATACTGCCTCT
        HHWHV   TATCTTCCTGCTGGTGGCTCCAGTTCAGGAACAGTAAACCCTGCTCCGAATATTGCCTCT
        WMHV    TACTTTCCTGCTGGTGGCTCAACTTCAAGCATTGTCAACCCTGTTCCGACCACTGCCTCC
        6101    TATCTTCCTGCTGGTGGCTCCAGTTCAGGAACAGTAAACCCTGTTCTGACTACTGCCTCT
        6102    TATCTTCCTGCTGGTGGCTCCAGTTCAGGAACAGTAAACCCTGCTCCGAATACTGCCTCT
        6103    TATCTCCCTGCTGGTGGCTCCAGTTCAGGAACAGTAAACCCTGCTCCGAATATTGCCTCT
        6104    TATCTTCCTGCTGGTGGCTCCAGTTCAGGAACAGTAAACCCTGCTCCGAATATTGCCTCT
        6105    TATCTTCCTGCTGGTGGCTCCAGTTCAGGAACAGTAAACCCTGCTCCGAATATTGCCTCT
        6106    TATTCCCTGCTGGTGGCTCCAGTTCAGGAACAGTAAACCCTGTTCTGACTACTGCCTCT
        6107    TATCTTCCTGCTGGTGGCTCCAGTTCAGGAACAGTAAACCCTGCTCCGAATATTGCCTCT
        6108    TATCTTCCTGCTGGTGGCTCCAGTTCAGGAACAGTAAACCCTGCTCCGAATATTGCCTCT
        6109    TATCTTCCTGCTGGTGGCTCCAGTTCAGGAACAGTAAACCCTGCTCCGAATATTGCCTCT
        6110    TATCTTCCTGCTGGTGGCTCCAGTTCAGGAACAGTAAACCCTGCTCCGAATATTGCCTCT
        6111    TACTTTCCTGTTGGTGGCTCCAGTTCAGGAACAGTAAACCCTGCTCCGAATATTGCCTCT
        6201    TATCTTCCTGCTGGTGGCTCCAGCTCAGGAACAGTAAACCCTGCTCCGAATATTGCCTCT
        6202    TATCTTCCTGCTGGTGGCTCCAGCTCAGGAACAGTAAACCCTGCTCCGAATATTGCCTCT
        6203    TATCTTCCTGCTGGTGGCTCCAGTTCAGGAACAGTAAACCCTGCTCCGAATATTGCCTCT
        6204    TATCTTCCTGCTGGTGGCTCCAGTTCAGGAACAGTAAACCCTGCTCCGAATATTGCCTCT
        6205    TATCTTCCTGCTGGTGGCTCCAGTTCAGGAACAGTAAACCCTGCTCCGAATACTGCCTCT
        6206    TATCTCCCTGCTGGTGGCTCCAGTTCAGGAACAGTAAACCCTGCTCCGAATATTGCCTCT
```

Figure 33 (continued)

```
6207   TATTTCCTGCTGGTGGCTCCAGTTCAGGAACAGTAAACCCTGTTCTGACTACTGCCTCT
6208   TATTTCCTGCTGGTGGCTCCAGTTCAGGAACAGTAAACCCTGTTCTGACTACTGCCTCT
6209   TATCTTCCTGCTGGTGGCTCCAGCTCAGGAACAGTAAACCCTGCTCCGAATATTGCCTCT
6210   TATCTTCCTGCTGGTGGCTCCAGTTCAGGAACAGTAAACCCTGCTCCGAATATTGCCTCT
6211   TATCTTCCTGCTGGTGGCTCCAGTTCAGGAACAGTAAACCCTGCTCCGAATACTGCCTCT
6212   TATCTTCCTGCTGGTGGCTCCAGCTCAGGAACAGTAAACCCTGCTCCGAATATTGCCTCT
6213   TATCTTCCTGCTGGTGGCTCCAGTTCAGGAACAGTAAACCCTGCTCCGAATACTGCCTCT
6214   TATCTTCCTGCTGGTGGCTCCAGTTCAGGAACAGTAAACCCTGCTCCGAATATTGCCTCT
6215   TATCTTCCTGCTGGTGGCTCCAGTTCAGGAACAGTAAACCCTGCTCCGAATATTGCCTCT 121       130       140       150       160       170       180
            |         |         |         |         |         |         |
HBV     CCCTTATCGTCAATCTTCTCGAGGATTGGGGACCCTGCGCTGAACATGGAGAACATCACA
CGHV    CACATCTCGTCAGTCTTCTCGACGACTGGGGACCCTGCACCGAACATGGAGAACATCACA
HHWHV   CACATCTCGTCAATCTCCGCGAGGACTGGGGACCCTGTGACGAACATGT----CACC--A
WMHV    ACCACATCGTCAAGCTTCTCGACGACTGGGGTCCCTGTCAGCACCATGGACATCACTTCA
6101    CCCTTATCGTCAATCTTCTCGAGGATTGGGGACCCTGCGCTGAACATGGAGAACATCACA
6102    CACATCTCGTCAGTCTTCTCGACGACTGGGGACCCTGCACCGAACATGGAGAACATCACA
6103    CACATCTCGTCAATCTCCGCGAGGACTGGGGACCCTGCACCGAACATGGAGAACATCACA
6104    CACATCTCGTCAATCTCCGCGAGGACTGGGGACCCTGCGCTGAACATGGAGAACATCACA
6105    CACATCTCGTCAATCTCCGCGAGGACTGGGGACCCTGCGCTGAACATGGAGAACATCACA
6106    CCCTTATCGTCAATCTTCTCGAGGATTGGGGACCCTGCGCTGAACATGGAGAACATCACA
6107    CCCTTATCGTCAATCTTCTCGACGACTGGGGACCCTGCACCGAACATGGAGAACATCACA
6108    CACATCTCGTCAATCTCCGCGAGGACTGGGGACCCTGTGACGAACATGT----CACC--A
6109    CACATCTCGTCAATCTCCGCGAGGACTGGGGACCCTGTGACGAACATGT----CACC--A
6110    CACATCTCGTCAATCTCCGCGAGGACTGGGGACCCTGTGACGAACATGT----CACC--A
6111    CCCTTATCGTCAATCTTCTCGAGGATTGGGGACCCTGCGCTGAACATGGAGAACATCACA
6201    CACATCTCGTCAATCTCCGCGAGGATTGGGGACCCTGCGCTGAACATGGGGAACATCACA
6202    CACATCTCGTCAATCTCCGCGAGGATTAGGGACCCTGCGCTGAACATGGAGAACATCGCA
6203    CACATCTCGTCAATCTCCGCGAGGACTGGGGACCCTGCGCTGAACATGGAGAACATCACA
6204    CACATCTCGTCAATCTCCGCGAGGACTGGGGACCCTGCGCTGAACATGGAGAACATCACA
6205    CACATCTCGTCAGTCTTCTCGACGACTGGGGACCCTGCACCGAACATGGAGAACATCACA
6206    CACATCTCGTCAATCTCCGCGAGGACTGGGGACCCTGCGCTGAACATGGAGAACATCACA
6207    CCCGTATCGTCAATCTTCTCGAGGATTGGGGACCCTGCGCTGAACATGGAGAACATCACA
6208    CCCTTATCGTCAATCTTCTCGAGGATTGGGGACCCTGCGCTGAACATGGAGAACATCACA
6209    CACATCTCGTCAATCTCCGCGAGGATTGGGGACCCTGCGCTGAACATGGAGAACATCACA
6210    CCCTTATCGTCAATCTTCTCGACGACTGGGGACCCTGCGCTGAACATGGAGAACATCACA
6211    CACATCTCGTCAGTCTTCTCGACGACTGGGGACCCTGCACCGAACATGGAGAACATCACA
6212    CACATCTCGTCAATCTCCGCGAGGATTGGGGACCCTGCGCTGAACATGGAGAACATCACA
6213    CACATCTCGTCAGTCTTCTCGACGACTGGGGACCCTGCACCGAACATGGAGAACATCACA
6214    CACATCTCGTCAATCTCCGCGAGGACTGGGGACCCTGCGCTGAACATGGAGAACATCACA
6215    CACATCTCGTCAATCTCCGCGAGGACTGGGGACCCTGTGACGAACATGT----CACC--A 181       190       200       210       220       230       240
            |         |         |         |         |         |         |
HBV     TCAGGATTCCTAGGACCCCTTCTCGTGTTACAGGCGGGGTTTTCTTGTTGACAAGAATC
CGHV    TCAGGATTCCTAGGACCCCTGCTCGTGTTACAGGCGGGGTTTTCTTGTTGACAAAAATC
HHWHV   TCAAGTCTCCTAGGACTCCTCGCAGGATTACAGGTGGTGTATTTCTTGTGGACAAAAATC
WMHV    TCAGGATTCCTAGGACCCCTTCTCGCATTACAGGGGGTGTTCTTGTTGACAAAAATC
6101    TCAGGATTCCTAGGACCCCTTCTCGTGTTACAGGCGGGGTTTTCTTGATGACAAAAATC
6102    TCAGGATTCCTAGGACCCCTGCTCGTGTTACAGGCGGGGTTTTCTTGTTGACAAAAATC
6103    TCAGGATTCCTAGGACCCCTGCTCGTGTTACAGGCGGTGTTTTCTTGTTGACAAGAATC
6104    TCAGGATTCCTAGGACCCCTTCTCGTGTTACAGGCGGGGTTTTCTTGTTGACAAGAATC
6105    TCAGGATTCCTAGGACCCCTTCTCGTGTTACAGGCGGGGTTTTCTTGTTGACAAGAATC
6106    TCAGGATTCCTAGGACCCCTTCTCGTGTTACAGGCGGGGTTTTCTTGTTGACAAGAATC
6107    TCAGGATTCCTAGGACCCCTTCTCGTGTTACAGGCGGGGTTTTCTTGTTGACAAGAATC
6108    TCAAGTCTCCTAGGACTCCTCGCAGGATTACAGGTGGTGTATTTCTTGTGGACAAAAATC
```

Figure 33 (continued)

```
6109    TCAAGTCTCCTAGGACTCCTCGCAGGATTACAGGTGGTGTATTTCTTGTGGACAAAAATC
6110    TCAAGTCTCCTAGGACTCCTCGCAGGATTACAGGTGGTGTATTTCTTGTGGACAAAAATC
6111    TCAGGATTCCTAGGACCCCTGCTCGTGTTACAGGCGGGGTTTTTCTTGTTGACAAAAGTC
6201    TCAGGATTCCTAGGACCCCTTCTCGTGTTACAGGCGGGGTTTTTCTTGATGACAAAAATC
6202    TCAGGATTCCTAGGACCCCTTCTCGCATTACAGGCGGTGTTTTTCTTGTTGACAAAAATC
6203    TCAGGATTCCTAGGACCCCTTCTCGTGTTACAGGCGGGGTTTTTCTTGTTGACAAGAATC
6204    TCAGGATTCCTAGGACCCCTTCTCGTGTTACAGGCGGGGTTTTTCTTGTTGACAAGAATC
6205    TCAGGATTCCTAGGACCCCTGCTCGTGTTACAGGCGGGGTTTTTCTTGTTGACAAAAATC
6206    TCAGGATTCCTAGGACCCCTGCTCGTGTTACAGGCGGTGTTTTTCTTGTTGACAAGAATC
6207    TCAGGATTCCTAGGACCCCTTCTCGTGTTACAGGCGGGGTTTTTCTTGTTGACAAGAATC
6208    TCAGGATTCCTAGGACCCCTTCTCGTGTTACAGGCGGGGTTTTTCTTGTTGACAAGAATC
6209    TCAGGATTCCTAGGACCCCTTCTCGCATTACAGGCGGTGTTTTTCTTGTTGACAAAAATC
6210    TCAGGATTCCTAGGACCCCTTCTCGTGTTACAGGCGGGGTTTTTCTTGTTGACAAGAATC
6211    TCAGGATTCCTAGGACCCCTGCTCGTGTTACAGGCGGGGTTTTTCTTGTTGACAAAAATC
6212    TCAGGATTCCTAGGACCCCTTCTCGCATTACAGGCGGTGTTTTTCTTGTTGACAAAAATC
6213    TCAGGATTCCTAGGACCCCTGCTCGTGTTACAGGCGGGGTTTTTCTTGTTGACAAAAATC
6214    TCAGGATTCCTAGGACCCCTTCTCGTGTTACAGGCGGGGTTTTTCTTGTTGACAAGAATC
6215    TCAAGTCTCCTAGGACTCCTCGCAGGATTACAGGTGGTGTATTTCTTGTGGACAAAAATC 241       250       260       270       280       290       300
         |         |         |         |         |         |         |
HBV     CTCACAATACCGCAGAGTCTAGACTCGTGGTGGACTTCTCTCAATTTTCTAGGGGGAACT
CGHV    CTCACAATACCACAGAGTCTAGACTCGTGGTGGACTTCTCTCAATTTTCTAGGGGGAGCA
HHWHV   CTAACAATAGCTCAGAATCTAGATTGGTGGTGGACTTCTCTCAGTTTTCCAGGGGGCATA
WMHV    CTCACAATGCCACAGAGTCTAGACTCGTTGTGGACTTCTCTCAATTTTCTAGGGGGAACA
6101    CTCACAATGCCGCAGAGTCTAGACTCGTGGTGGACTTCTCTCAATTTTCTAGGGAGAGCA
6102    CTCACAATGCCACAGAGTCTAGACTCGTTGTGGACTTCTCTCAATTTTCTAGGGGGAACA
6103    CTCACAATACCACAGAGTCTAGACTCGTGGTGGACTTCTCTCAATTTTCTAGGGGGAACT
6104    CTCACAATACCACAGAGTCTAGACTCGTGGTGGACTTCTCTCAATTTTCTAGGGGGAACT
6105    CTCACAATACCACAGAGTCTAGACTCGTGGTGGACTTCTCTCAATTTTCTAGGGGGAACT
6106    CTCACAATACCGCAGAGTCTAGACTCGTTGTGGACTTCTCTCAGTTTTCCAGGGGGCATA
6107    CTCACAATACCGCAGAGTCTAGACTCGTGGTGGACTTCTCTCAATTTTCTAGGGGGAGCA
6108    CTAACAATACCGCAGAGTCTAGACTCGTGGTGGACTTCTCTCAATTTTCTAGGGGGAGCA
6109    CTAACAATACCGCAGAGTCTAGACTCGTGGTGGACTTCTCTCAATTTTCTAGGGGGAGCA
6110    CTAACAATACCGCAGAGTCTAGACTCGTGGTGGACTTCTCTCAATTTTCTAGGGGGAGCA
6111    CTCACAATACCGCAGAGCCTAGACTCGTGGTGGACTTCTCTCAATTTTCTAGGGGAACT
6201    CTCACAATGCCGCAGAGTCTAGACTCGTGGTGGACTTCTCTCAATTTTCTAGGGGGAACT
6202    CTCACAATGCCACAGAGTCTAGACTCGTGGTGGACTTCTCTCAATTTTCTAGGGGGAACT
6203    CTCACAATACCACAGAGTCTAGACTCGTGGTGGACTTCTCTCAATTTTCTAGGGGGAGCA
6204    CTCACAATACCACAGAGTCTAGACTCGTGGTGGACTTCTCTCAATTTTCTAGGGGGAACT
6205    CTCACAATGCCACAGAGTCTAGACTCGTTGTGGACTTCTCTCAATTTTCTAGGGGGAACA
6206    CTCACAATACCACAGAGTCTAGACTCGTGGTGGACTTCTCTCAATTTTCTAGGGGGAACA
6207    CTCACAATACCGCAGAGTCTAGACTCGTTGTGGACTTCTCTCAGTTTCCAAGGGGCATA
6208    CTCACAATACCGCAGAGTCTAGACTCGTTGTGGACCTCTCTCAGTTTTCCAGGGGGCATA
6209    CTCACAATGCCACAGAGTCTAGACTCGTGGTGGACTTCTCTCAATTTTCTAGGGGGAACT
6210    CTCACAATACCGCAGAGTCTAGACTCGTGGTGGACTTCTCTCAATTTTCTAGGGGGAGCA
6211    CTCACAATGCCACAGAGTCTAGACTCGTTGTGGACTTCTCTCAATTTTCTAGGGGGAACA
6212    CTCACAATGCCACAGAGTCTAGACTCGTGGTGGACTTCTCTCAATTTTCTAGGGGGAACT
6213    CTCACAATGCCACAGAGTCTAGACTCGTTGTGGACTTCTCTCAATTTTCTAGGGGGAACA
6214    CTCACAATACCACAGAGTCTAGACTCGTGGTGGACTTCTCTCAATTTTCTAGGGGGAACT
6215    CTAACAATACCGCAGAGTCTAGACTCGTGGTGGACTTCTCTCAATTTTCTAGGGGGAGCA 301       310       320       330       340       350       360
         |         |         |         |         |         |         |
HBV     ACCGTGTGTCTTGGCCAAAATTCGCAGTCCCCAACCTCCAATCACTCACCAACCTCTTGT
CGHV    CCCGTGTGTCCTGGCCAAAATTCGCAGTCCCCAACCTCCAATCACTCACCAACCTCTTGT
HHWHV   CCAGAGTGCACTGGCCAAAATTCGCAGTTCCAAACTTGCAAACACTTGCCAACCTCCTGT
```

Figure 33 (continued)

```
WMHV   CCAGCGTGTCCTGGCCTAAATTCGCAGTCCCCAACCTCCAGTCACTCACCAACCTGCTGT
6101   CCCGTGTGTCCTGGCCAAAATTCGCAGTCCCCAACCTCCAATCACTCACCAACCTCTTGT
6102   CCAGCGTGTCTTGGCCAAAATTCGCAGTCCCCAACCTCCAATCACTCACCAACCTCTTGT
6103   ACCGTGTGTCCTGGCCAAAATTCGCAGTCCCCAACCTCCAATCACTCACCAACCTCTTGT
6104   ACCGTGTGTCTTGGCCTAAATTCGCAGTCCCCAACCTCCAATCACTCACCAACCTCTTGT
6105   ACCGTGTGTCTTGGCCTAAATTCGCAGTCCCCAACCTCCAATCACTCACCAACCTCTTGT
6106   CCAGAGTGCACTGGCCAAAATTCGCAGTCCCCAACCTCCAATCACTCACCAACCTCTTGT
6107   CCCGTGTGTCTTGGCCAAAATTCGCAGTCCCCAACCTCCAATCACTCACCAACCTCTTGT
6108   CCCGTGTGTCCTGGCCAAAATTCGCAGTCCCCAACCTCCAATCACTCACCAACCTCTTGT
6109   CCCGTGTGTCCTGGCCAAAATTCGCAGTCCCCAACCTCCAATCACTCACCAACCTCTTGT
6110   CCCGTGTGTCCTGGCCAAAATTCGCAGTCCCCAACCTCCAATCACTCACCAACCTCTTGT
6111   ACCGTGTGTCTTGGCCAAAATTCGCAGTCCCCAACCTCCAATCACTCACCAACCTCTTGT
6201   ACCGTGCGTCCTGGCCAAAATTCGCAGTCCCCAACCTCCAATCACTCACCAACCTCTTGT
6202   ACCGTGTGTCTTGGCCAAAATTCGCAGTCCCCAACCTCCAATCACTCACCAACCTCTTGT
6203   CCCGTGTGTCCTGGCCAAAATTCGCAGTCCCCAACCTCCAATCACTCACCAACCTCTTGT
6204   ACCGTGTGTCTTGGCCTAAATTCGCAGTCCCCAACCTCCAATCACTCACCAACCTCTTGT
6205   CCAGCGTGTCTTGGCCAAAATTCGCAGTCCCCAACCCCCAATCACTCACCAACCTCTTGC
6206   CCCGTGTGTCCTGGCCAAAATTCGCAGTCCCCAACCTCCAATCACTCACCAACCTCTTGT
6207   CCAGAGTGCACTGGCCAAAATTCGCAGTCCCCAACCTCCAATCACTCACCAACCTCTTGT
6208   CCAGAGTGCACTGGCCAAAATTCGCAGTCCCCAACCTCCAATCACTCACCAACCTCTTGT
6209   ACCGTGTGTCTTGGCCTAAATTCGCAGTCCCCAACCTCCAATCACTCACCAACCTCTTGT
6210   CCCGTGTGTCTTGGCCAAAATTCGCAGTCCCCAACCTCCAATCACTCACCAACCTCTTGT
6211   CCAGCGTGTCTTGGCCAAAATTCGCAGTCCCCAACCTCCAATCACTCACCAACCTCTTGT
6212   ACCGTGTGTCTTGGCCAAAATTCGCAGTCCCCAACCTCCAATCACTCACCAACCTCTTGT
6213   CCAGCGTGTCTTGGCCAAAATTCGCAGTCCCCAACCTCCAATCACTCACCAACCTCTTGT
6214   ACCGTGTGTCTTGGCCTAAATTCGCAGTCCCCAACCTCCAATCACTCACCAACCTCTTGT
6215   CCCGTGTGTCCTGGCCAAAATTCGCAGTCCCCAACCTCCAATCACTCACCAACCTCTTGT 361       370       380       390       400       410       420
        |         |         |         |         |         |         |
HBV    CCTCCAACTTGTCCTGGTTATCGCTGGATGTGTCTGCGGCGTTTTATCATCTTCCTCTTC
CGHV   CCTCCAATTTGTCCTGGCTATCGCTGGATGTGTCTGCGGCGTTTTATCATCTTCCTCTTC
HWHV   CCACCAACTTGCAATGGCTTTCGTTGGATGTATCTGCGGCGTTTTATCATATACCTATTA
WMHV   CCACCGACTTGTCCTGGGTATCGCTGGATGTGTTTGCGGCGTTCTATCATCTTCCTCTTC
6101   CCTCCAATTTGTCCTGGCTATCGCTGGATGTGTCTGCGGCGTTTTATCATCTTCCTCTTC
6102   CCTCCAACTTGTCCTGGTTATCGCTGGATGTGTCTGCGGCGTTTTATCATCTTCCTCTTC
6103   CCTCCAACTTGTCCTGGTTATCGCTGGATGTGTCTGCGGCGTTTTATCATATACCTATTA
6104   CCTCCAACTTGTCCTGGTTATCGCTGGATGTGTCTGCGGCGTTTTATCATCTTCCTCTTC
6105   CCTCCAACTTGTCCTGGTTATCGCTGGATGTGTCTGCGGCGTTTTATCATCTTCCTCTTC
6106   CCTCCAACTTGTCCTGGTTATCGCTGGATGTGTCTGCGGCGTTTTATCATCTTCCTCTTC
6107   CCTCCAACTTGTCCTGGGTATCGCTGGATGCGTCTGCGGCGTTTTATCATCTTCCTCTTC
6108   CCTCCAATTTGTCCTGGTTATCGCTGGATGTGTCTGCGGCGTTTTATCATCTTCCTCTTC
6109   CCTCCAACTTTGTCCTGGTTATCGCTGGATGTGTCTGCGGCGTTTTATCATCTTCCTCTTC
6110   CCTCCAATTTGTCCTGGTTATCGCTGGATGTGTCTGCGGCGTTTTATCATCTTCCTCTTC
6111   CCTCCAACTTGTCCTGGTTATCGCTGGATGTGTCTGCGGCGTTTTATCATCTTCCTCTTC
6201   CCTCCAACTTGTCCTGGTTATCGCTGGATGTGTCTGCGGCGTTTTATCATCTTCCTCTTC
6202   CCTCCAACTTGTCCTGGTTATCGCTGGATGTGTCTGCGGCGTTTTATCATCTTCCTCTTC
6203   CCTCCGATTTGTCCTGGCTATCGCTGGATGTGTCTGCGGCGTTTTATCATCTTCCTCTTC
6204   CCTCCAACTTGTCCTGGTTATCGCTGGATGTGTCTGCGGCGTTTTATCATCTTCCTCTTC
6205   CCTCCAACTTGTCCTGGTTATCGCTGGATGTGTCTGCGGCGTTTTATCATCTTCCTCTTC
6206   CCTCCAACTTGTCCTGGTTATCGCTGGATGTGTCTGCGGCGTTTTATCATCTTCCTCTTC
6207   CCTCCAACTTGTCCTGGTTATCGCTGGATGTGTCTGCGGCGTTTTATCATCTTCCTCTTC
6208   CCTCCAACTTGTCCTGGTTATCGCTGGATGTGTCTGCGGCGTTTTATCATCTTCCTCTTC
6209   CCTCCAACTTGTCCTGGTTATCGCTGGATGTGTCTGCGGCGTTTTATCATCTTCCTCTTC
6210   CCTCCAACTTGTCCTGGTTATCGCTGGATGTGTCTGCGGCGTTTTATCATCTTCCTCTTC
6211   CCTCCAACTTGTCCTGGTCATCGCTGGATGTGTCTGCGGCGTTTTATCATCTTCCTCTTC
6212   CCTCCAACTTGTCCTGGTTATCGCTGGATGTGTCTGCGGCGTTTTATCATCTTCCTCTTC
```

Figure 33 (continued)

```
6213    CCTCCAACTTGTCCTGGTTATCACTGGATGTGTCTGCGGCGTTTTATCATCTTCCTCTTC
6214    CCTCCAACTTGTCCTGGTTATCGCTGGATGTGTCTGCGGCGTTTTATCATCTTCCTCTTC
6215    CCTCCAACTTGTCCTGGTTATCGCTGGATGTGTCTGCGGCGTTTTATCATCTTCCTCTTC 421       430       440       450       460       470       480
               |         |         |         |         |         |         |
HBV     ATCCTGCTGCTATGCCTCATCTTCTTGTTGGTTCTTCTGGACTATCAAGGTATGTTGCCC
CGHV    ATCCTGCTGCTATGCCTCATCTTCTTGTTGGTTCTTCTGGACTATCGAGGTATGTTGCCC
HWHV    GTCCTGCTGCTGTGCCTCATCTTCTTGTTGGTTCTCCTGGACTGGAAAGGTTTAATACCT
WMHV    ATCCTGCTTCTATGCCTCATCTTCTTGTTGGTCTTCTGGACTACCAAGGTATGTTGCCC
6101    ATCCTGCTGCTATGCCTCATCTTCTTGTTGGTTCTTCTGGACTATCGAGGTATGTTGCCC
6102    ATCCTGCTGCTATGCCTCATCTTCTTGTTGGTTCTTCTGGACTATCGAGGTATGTTGCCC
6103    GTCCTGCTGCTGTGCCCTCATCTTCTTGTTGGTTCTTCTGGACTATCAAGGTATGTTGCCC
6104    ATCCTGCTTCTATGCCTCATCTTCTTGTTGGTTCTTCTGGACTATCAAGGTATGTTGCCC
6105    ATCCTGCTTCTATGCCTCATCTTCTTGTTGGTTCTTCTGGACTATCAAGGTATGTTGCCC
6106    ATCCTGCTGCTATGCCTCATCTTCTTGTTGGTTCTTCTGGACTATCGAGGTATGTTGCCC
6107    ATCCTGCTGCTATGCCTCATCTTCTTGTTGGTTCTTCTGGACTATCGAGGTATGTTGCCC
6108    ATCCTGCTTCTATGCCTCATCTTCTTGTTGGTTCTTCTGGACTATCAAGGTATGTTGCCC
6109    ATCCTGCTTCTATGCCTCATCTTCTTGTTGGTTCTTCTGGACTATCAAGGTATGTTGCCC
6110    ATCCTGCTTCTATGCCTCATCTTCTTGTTGGTTCTTCTGGACTATCAAGGTATGTTGCCC
6111    ATCCTGCTGCTATGCCTCATCTTCTTGTTGGTTCTTCTGGACTATCGAGGTATGTTGCCC
6201    ATCCTGCTGCTATGCCTCATCTTCTTGTTGGTTCTTCTGGACTATCGAGGTATGTTGCCC
6202    ATCCTGCTGCTATGCCTCATCTTCTTGTTGGTTCTTCTGGACTATCGAGGTATGTTGCCC
6203    ATCCTGCTGCTATGCCTCATCTTCTTGTTGGTTCTTCTGGACTATCGAGGTATGTTGCCC
6204    ATCCTGCTTCTATGCCTCATCTTCTTGTTGGTTCTTCTGGACTATCAAGGTATGTTGCCC
6205    ATCCTGCTTCTATGCCTCATCTTCTTGTTGGTTCTTCTGGACTATCAAGGTATGTTGCCC
6206    ATCCTGCTTCTATGCCTCATCTTCTTGTTGGTTCTTCTGGACTATCAAGGTATGTTGCCC
6207    ATCCTGCTGCTATGCCTCATCTTCTTGTTGGTTCTTCTGGACTATCGAGGTATGTTGCCC
6208    ATCCTGCTGCTATGCCTCATCTTCTTGTTGGTTCTTCTGGACTATCGAGGTATGTTGCCC
6209    ATCCTGCTGCTGTGCCTCATCTTCTTGTTGGTTCTTCTGGACTATCGAGGTATGTTGCCC
6210    ATCCTGCTGCTATGCCTCATCTTCTTGTTGGTTCTTCTGGACTATCGAGGTATGTTGCCC
6211    ATCCTGCTGCTATGCCTCATCTTCTTGTTGGTTCTTCTGGACTATCGAGGTATGTTGCCC
6212    ATCCTGCTGCTATGCCTCATCTTCTTGTTGGTTCTTCTGGACTATCGAGGTATGTTGCCC
6213    ATCCTGCTGCTATGCCTCATCTTCTTGTTGGTTCTTCTGGACTATCGAGGTATGTTGCCC
6214    ATCCTGCTTCTATGCCTCATCTTCTTGTTGGTTCTTCTGGACTATCAAGGTATGTTGCCC
6215    ATCCTGCTGCTATGCCTCATCTTCTTGTTGGTTCTTCTGGACTATCGAGGTATGTTGCCC 481       490       500       510       520       530       540
               |         |         |         |         |         |         |
HBV     GTTTGTCCTCTAATTCCAGGATCCTCA------ACAACCAGCACGGGACCATGCCGGACC
CGHV    GTTTGTCCTCTACTTCCAGGATCATCG------ACCACCAGCACGGGACCATGCAAAACC
HWHV    GTCTGTCCTCTTC-------AACCCACA------ACAGAAACAACAGTCAATTGCAGACAA
WMHV    GTGTGTCCTCTTCTACCAACAGTTACAGGAACAACAACAACAACGGGACCCTGCAGGACC
6101    GTTTGTCCTCTACTTCCAGGATCATCG------ACCACCAGCACGGGACCATGCAAAACC
6102    GTTTGTCCTCTAATTCCAGGATCCTCA------ACAACCAGCACGGGACCTTGCAGGACC
6103    GTTTGTCCTCTAATTCCAGGATCCTCA------ACAACCAGCACGGGACCATGCAAAACC
6104    GTTTGTCCCCTAATTCCAGGATCCTCA------ACAACCAGCACGGGACCATGCAAAACC
6105    GTTTGTCCCCTAATTCCAGGATCCTCA------ACAACCAGCACGGGACCATGCAAAACC
6106    GTTTGTCCTCTACTTCCAGGATCCTCA------ACAACCAGCACGGGACCCTGCAGGACC
6107    GTTTGTCCTCTAATTCCAGGATCCTCA------ACAACCGGCACGGGACCCTGCAGGACC
6108    GTTTGTCCTCTAATTCCAGGATCATCG------ACCACCAGCACGGGACCATGCAAAACC
6109    GTTTGTCCTCTAATTCCAGGATCATCG------ACCACCAGCACGGGACCATGCAAAACC
6110    GTTTGTCCTCTAATTCCAGGATCATCG------ACCACCAGCACGGGACCATGCAAAACC
6111    GTTTGTCCTCTAATTCCAGGATCCTCA------ACAACCAGCACGGGACCCTGCAGGACC
6201    GTTTGTCCTCTACTTCCAGGGTCCTCA------ACAACCAGCACGGGACCCTGCAGGACC
6202    GTTTGTCCTCTAATTCCAGGATCCTCA------ACAACCAGCACGGGACCATGCAAAACC
6203    GTTTGTCCTCTACTTCCAGGATCCTCA------ACAACCAGCACGGGACCATGCCGGACC
```

Figure 33 (continued)

```
6204    GTTTGTCCCCTAATTCCAGGATCCTCA------ACAACCAGCACGGGACCATGCAAAACC
6205    GTTTGTCCTCTAATTCCAGGATCCTCA------ACAACCAGCACGGGACCATGCAAAACC
6206    GTTTGTCCCCTAATTCCAGGATCCTCA------ACAACCAGCACGGGACCATGCAAAACC
6207    GTTTGTCCTCTACTTCCAGGATCCTCA------ACAACCAGCACGGGACCCTGCAGGACC
6208    GTTTGTCCTCTACTTCCAGGATCCTCA------ACAACCAGCACGGGACCCTGCAGGACC
6209    GTTTGTCCTCTACTTCCAGGATCCTCA------ACAACCAGCACGGGACCATGCCGGACC
6210    GTTTGTCCTCTAATTCCAGGATCCTCA------ACAACCAGCACGGGACCCTGCAGGACC
6211    GTTTGTCCTCTAATTCCAGGATCCTCA------ACAACCAGCACGGGACCATGCAAAACC
6212    GTTTGTCCTCTAATTCCAGGATCCTCA------ACAACCAGCACGGGACCATGCAAAACC
6213    GTTTGTCCTCTACTTCCAGGATCATCG------ACCACCAGCACGGGACCATGCAAAACC
6214    GTTTGTCCCCTAATTCCAGGATCCTCA------ACAACCAGCACGGGACCATGCAAAACC
6215    GTTTGTCCTCTACTTCCAGGATCCTCA------ACAACCAGCACGGGACCCTGCAGGACC 541       550       560       570       580       590       600
           |         |         |         |         |         |         |
HBV     TGCATGACTACTGCTCAAGGAACCTCTATGTATCCCTCCTGTTGCTGTACCAAACCTTCG
CGHV    TGCACGATCCCTGCTCAAGGAACCTCTTTGATTCCCTCATGTTGTTGTACAAAACCTTCG
HWHV    TGCACAATCTCTGCACAAGACATGTATACTCCTCCTTACTGTTGTTGTTTAAAACCTACG
WMHV    TGCACGCCAATTGTTCCAGGCATCTCTTCGTATCCCTCATGTTGCTGTACCAAACCTACG
6101    TGCACGATCCCTGCTCAAGGAACCTCTTTGATTCCCTCATGTTGTTGTACAAAACCTTCG
6102    TGTATGACTACCGCTCAAGGAACCTCTATGTATCCCTCATGTTGTTGTACAAAACCTTCG
6103    TGTATGACTACCGCTCAAGGAACCTCTATGTATCCCTCATGTTGTTGTACAAAACCTTCG
6104    TGTATGACTACCCCTCAAGGAACCTCTATGTATCCCTCATGTTGCTGTACCAAACCTTCG
6105    TGTATGACTACCCCTCAAGGAACCTCTATGTATCCCTCATGTTGCTGTACCAAACCTTCG
6106    TGTATGACTACCGCTCAAGGAACCTCTATGTATCCCTCATGTTGCTGTACCAAACCTTCG
6107    TGTATGACTACTGCTCAAGGAACCTCTATGTATCCCTCATGTTGTTGTACAAAACCTTCG
6108    TGTATGACTACCCCTCAAGGAACCTCTATGTATCCCTCATGTTGTTGTACCAAACCTTCG
6109    TGTATGACTACCCCTCAAGGAACCTCTATGTATCCCTCATGTTGTTGTACCAAACCTTCG
6110    TGTATGACTACCCCTCAAGGAACCTCTATGTATCCCTCATGTTGTTGTACCAAACCTTCG
6111    TGTATGACTACCGCTCAAGGAACCTCTATGTATCCCTCATGTTGTTGTACAAAACCTTCG
6201    TGTATGACTACCGCTCAAGGAACCTCTATGTATCCCTCATGTTGCTGTACCAAACCTTCG
6202    TGTATGACTACCGCTCAAGGAACCTCTATGTATCCCTCATGTTGTTGTACAAAACCTTCG
6203    TGCATGACTACCGCTCAAGGAACCTCTATGTATCCCTCATGTTGCTGTACCAAACCTTCG
6204    TGTATGACTACCCCTCAAGGAACCTCTATGTATCCCTCATGTTGCTGTACCAAACCTTCG
6205    TGTATGACTACCCCTCAAGGAACCTCTATGTATCCCTCATGTTGCTGTACCAAACCTTCG
6206    TGTATGACTACCCCTCAAGGAACCTCTATGTATCCCTCATGTTGCTGTACCAAACCTTCG
6207    TGTATGACTACCGCTCAAGGAACCTCTATGTATCCCTCATGTTGCTGTACCAAACCTTCG
6208    TGTATGACTACCGCTCAAGGAACCTCTATGTATCCCTCATGTTGCTGTACCAAACCTTCG
6209    TGCATGACTACCGCTCAAGGAACCTCTATGTATCCCTCATGTTGCTGTACCAAACCTTCG
6210    TGTATGACTGCCGCTCAAGGAACCTCTATGTATCCCTCATGTTGCTGTACCAAACCTTCG
6211    TGTATGACTACCCCTCAAGGAACCTCTATGTATCCCTCATGTTGCTGTACCAAACCTTCG
6212    TGTATGACTACCGCTCAAGGAACCTCTATGTATCCCTCATGTTGTTGTACAAAACCTTCG
6213    TGCACGATCCCTGCTCAAGGAACCTCTTTGATTCCCTCATGTTGTTGTACAAAACCTTCG
6214    TGTATGACTACCCCTCAAGGAACCTCTATGTATCCCTCATGTTGCTGTACCAAACCTTCG
6215    TGTATGACTACCGCTCAAGGAACCTCTATGTATCCCTCATGTTGCTGTACCAAACCTTCG 601       610       620       630       640       650       660
           |         |         |         |         |         |         |
HBV     GACGGAAATTGCACCTGTATTCCCATCCCATCATCCTGGGCTTTCGGAAAATTCCTATGG
CGHV    GACGGAAATTGCACTTGTATTCCCATCCCATCGTCTTGGGCTTTCGCAAAATTCCTATGG
HWHV    GCAGGAAATTGCACTTGTTGGCCCATCCCTTCATCATGGGCTTTAGGAAATTACCTATGG
WMHV    GACGGAAACTGCACTTGTATTCCCATCCCCTCATCATGGGCTTTCGCAAAGTTCCTATGG
6101    GACGGAAATTGCACTTGTATTCCCATCCCATCGTCTTGGGCTTTCGCAAAATTCCTATGG
6102    GACGGAAATTGCACCTGTATTCCCATCCCATCATCCTGGGCTTTCGGAAAATTCCTATGG
6103    GACGGAAATTGCACTTGTATTCCCATCCCATCATCCTGGGCTTTCGGAAAATTCCTATGG
6104    GACGGAAATTGCACCTGTATTCCCATCCCATCATCCTGGGCTTTCGGAAAATTCCTATGG
6105    GACGGAAATTGCACCTGTATTCCCATCCCATCATCCTGGGCTTTCGGAAAATTCCTATGG
```

Figure 33 (continued)

```
6106    GACGGAAATTGCACCTGTATTCCCATCCCATCATCCTGGGCTTTCGCAAAATTCCTATGG
6107    GACGGAAATTGCACTTGTATTCCCATCCCATCATCCTGGGCTTTCGGAAAATTCCTATGG
6108    GACGGAAATTGCACCTGTATTCCCATCCCATCATCCTGGGCTTTCGGAAAATTCCTATGG
6109    GACGGAAATTGCACCTGTATTCCCATCCCATCATCCTGGGCTTTCGGAAAATTCCTATGG
6110    GACGGAAATTGCACCTGTATTCCCATCCCATCATCCTGGGCTTTCGGAAAATTCCTATGG
6111    GACGGAAATTGCACTTGTATTCCCATCCCATCATCCTGGGCTTTCGGAAAATTCCTATGG
6201    GACGGAAATTGCACCTGTATTCCCATCCCATCATCCTGGGCTTTCGCAAAATTCCTATGG
6202    GACGGAAATTGCACCTGTATTCCCATCCCATCATCCTGGGCTTTCGCAAAATTCCTATGG
6203    GACGGAAGCTGCACTTGTATTCCCATCCCATCATCCTGGGCTTTCGCAAAATTCCTATGG
6204    GACGGAAATTGCACCTGTATTCCCATCCCATCATCCTGGGCTTTCGGAAAATTCCTATGG
6205    GACGGAAATTGCACCTGTATTCCCATCCCATCATCCTGGGCTTTCGGAAAATTCCTATGG
6206    GACGGAAATTGCACCTGTATTCCCATCCCATCATCCTGGGCTTTCGGAAAATTCCTATGG
6207    GACGGAAATTGCACCTGTATTCCCATCCCATCATCCTGGGCTTTCGCAAAATTCCTATGG
6208    GACGGAAATTGCACCTGTATTCCCATCCCATCATCCTGGGCTTTCGGAAAATTCCTATGG
6209    GACGGAAGCTGCACTTGTATTCCCATCCCCTCATCCTGGGCTTTCGGAAAATTCCTATGG
6210    GACGGAAATTGCACCTGTATTCCCATCCCATCATCCTGGGCTTTCGCAAAATTCCTATGG
6211    GACGGAAATTGCACCTGTATTCCCATCCCATCATCCTGGGCTTTCGGAAAATTCCTATGG
6212    GACGGAAATTGCACCTGTATTCCCATCCCATCATCCTGGGCTTTCGGAAAATTCCTATGG
6213    GACGGAAATTGCACTTGTATTCCCATCCCATCGTCTTGGGCTTTCGCAAAATTCCTATGG
6214    GACGGAAATTGCACCTGTATTCCCATCCCATCATCCTGGGCTTTCGGAAAATTCCTATGG
6215    GACGGAAATTGCACCTGTATTCCCATCCCATCATCCTGGGCTTTCGGAAAATTCCTATGG 661       670       680       690       700       710       720
          |         |         |         |         |         |         |
HBV     GAGTGGGCCTCAGCCCGTTTCTCCTGGCTCAGTTACTAGTGCCATTTGTTCAGTGGTTC
CGHV    GAGTGGGCCTCAGTCCGTTTCTCCTGGCTCAGTTACTAGCTCCATTTGTTCAGCGGTTC
HWHV    GAGTGGGCCTTAGCCCGTTTCTCTTGGCTCAATTACTAGCTGCCCTTGCTTCAATGGTTA
WMHV    GACTGGGCCTTAGCCCGTTTCTCCTGGCTCAATTCACTTCTGCCATTTGTTCAGTGGTTC
6101    GAGTGGGCCTCAGTCCGTTTCTCCTGGCTCAGTTACTAGCTCCATTTGTTCAGCGGTTC
6102    GACTGGGCCTCAGCCCGTTTCTCCTGGCTCAGTTACTAGTGCCATTTGTTCAGCGGTTC
6103    GAGTGGGCCTCAGCCCGTTTCTCCTGGCTCAGTTACTAGTGCCATTTGTTCAGCGGTTC
6104    GAGTGGGCCTCAGCCCGTTTCTCCTGGCTCAGTTACTAGTGCCATTTGTTCAGTGGTTC
6105    GAGTGGGCCTCAGCCCGTTTCTCCTGGCTCAGTTACTAGTGCCATTTGTTCAGTGGTTC
6106    GAGTGGGCCTCAGCCCGTTTCTCCTGGCTCAGTTACTAGTGCCATTTGTTCAGCGGTTC
6107    GAGTGGGCCTCAGCCCGTTTCTCCTGGCTCAGTTACTAGTGCCATTTGTTCAGTGGTTC
6108    GAGTGGGCCTCAGTCCGTTTCTCCTGGCTCAGTTACTAGCTCCATTTGTTCAGCGGTTC
6109    GAGTGGGCCTCAGTCCGTTTCTCCTGGCTCAGTTACTAGCTCCATTTGTTCAGCGGTTC
6110    GAGTGGGCCTCAGTCCGTTTCTCCTGGCTCAGTTACTAGCTCCATTTGTTCAGCGGTTC
6111    GAGTGGGCCTCAGCCCGTTTCTCCTGGCTCAGTTACTAGTGCCATTTGTTCAGTGGTTC
6201    GAGTGGGCCTCAGCCCGTTTCTCCTGGCTCAGTTACTAGTGCCATTTGTTCAGTGGTTC
6202    GAGTGGGCCTCAGCCCGTTTCTCCTGGCTCAGTTACTAGTGCCATTTGTTCAGTGGTTC
6203    GAGTGGGCCTCAGCCCGTTTCTCCTGGCTCAGTTACTAGTGCCATTTGTTCAGTGGTTC
6204    GAGTGGGCCTCAGCCCGTTTCTCCTGGCTCAGTTACTAGTGCCATTTGTTCAGTGGTTC
6205    GAGTGGGCCTCAGCCCGTTTCTCCTGGCTCAGTTACTAGTGCCATTTGTTCAGTGGTTC
6206    GAGTGGGCCTCAGCCCGTTTCTCCTGGCTCAGTTACTAGTGCCATTTGTTCAGCGGTTC
6207    GAGTGGGCCTCAGCCCGTTTCTCCTGGCTCAGTTACTAGTGCCATTTGTTCAGTGGTTC
6208    GAGTGGGCCTCAGTCCGTTTCTCCTGGCTCAGTTACTAGCTCCATTTGTTCAGCGGTTC
6209    GAGTGGGCCTCAGTCCGTTTCTCCTGGCTCAGTTACTAGTGCCATTTGTTCAGTGGTTC
6210    GAGTGGGCCTCAGCCCGTTTCTCCTGGCTCAGTTACTAGTGCCATTTGTTCAGTGGTTC
6211    GAGTGGGCCTCAGCCCGTTTCTCCTGGCTCAGTTACTAGTGCCATTTGTTCAGTGGTTC
6212    GAGTGGGCCTCAGCCCGTTTCTCCTGGCTCAGTTACTAGCTCCATTTGTTCAGCGGTTC
6213    GAGTGGGCCTCAGCCCGTTTCTCCTGGCTCAGTTACTAGTGCCATTTGTTCAGCGGTTC
6214    GAGTGGGCCTCAGCCCGTTTCTCCTGGCTCAGTTACTAGTGCCATTTGTTCAGTGGTTC
6215    GAGTGGGCCTCAGCCCGTTTCTCCTGGCTCAGTTACTAGTGCCATTTGTTCAGTGGTTC 721       730       740       750       760       770       780
          |         |         |         |         |         |         |
```

Figure 33 (continued)

```
HBV    GTAGGGCTTTCCCCCACTGTTTGGCTTTCAGTTATATGGATGATGTGGTATTGGGGGCCA
CGHV   GCAGGGCTTTCCCCCACTGCTTGGCTTTTAGCTATATGGATCATCTGGTATTGGGGGCCA
HWHV   GGAGGAATTTCCCTCATTGCGTGGTTTTTGCTTATATGGATGATTTGGTTTTGGGGGCCC
WMHV   GCAGGGCTTTCCCCCACTGTATGGCTTTTAGTTATATGGATGATGTGGTTCTGGGGGCCA
6101   GCAGGGCTTTCCCCCACTGCTTGGCTTTTAGCTATATGGATCATCTGGTATTGGGGGCCA
6102   GCAGGGCTTTCTCCCACTGCTTGGCTTTCAGTTATATGGATGATGTGGTATTGGGGACCA
6103   GCAGGGCTTTCCCCCACTGTTTGGCTTTCAGTTATATGGATCATTTGGTTTTGCGGGCCA
6104   GTAGGGCTTTCCCCCACTGCTTGGCTTTTGGCTATATGGATCATCTGGTATTGGGGGCCA
6105   GTAGGGCTTTCCCCCACTGCTTGGCTTTTGGCTATATGGATCATCTGGTATTGGGGGCCA
6106   GTAGGGCTTTCCCCCACTGTTTGGCTTTCAGTTATATGGATCATCTGGTATTGGGGGCCA
6107   GTAGGGCTTTCCCCGCTGTATGGCTTTCAGTTATATGGATGATGTGGTATTGGGGGCCA
6108   GTAGGGCTTTCCCCCACTGTTTGGCTTTCAGTTATATGGATGATGTGGTTCTGGGGGCCA
6109   GTAGGGCTTTCCCCCACTGTTTGGCTTTCAGTTATATGGATGATGTGGTTCTGGGGGCCA
6110   GTAGGGCTTTCCCCCACTGTTTGGCTTTCAGTTATATGGATGATGTGGTTCTGGGGGCCA
6111   GTAGGGCTTTCCCCCACTGCTTGGCTTTTAGCTATATGGATCATCTGGTATTGGGGGCCA
6201   GTAGGGCTTTCCCCCACTGTTTGGCTTTCAGTTATATGGATCATCTGGTATTGGGGGCCA
6202   GTAGGGCTTTCCCCCACTGTTTGGCTTTCAGTTATATGGATGATGTGGTATTGGGGACCA
6203   GTAGGGCTTTCCCCGCTGTATGGCTTTCAGTTATATGGATGATTTGGTTTTGGGGGCCA
6204   GTAGGGCTTTCCCCCACTGCTTGGCTTTTGGCTATATGGATCATCTGGTATTGGGGGCCA
6205   GTAGGGCTTTCCCCCACTGCTTGGCTTTTGGCTATATGGATCATCTGGTATTGGGGGCCA
6206   GCAGGGCTTTCCCCCACTGTTTGGCTTTCAGTTATATGGATCATTTGGTTTTGGGGGCCA
6207   GTAGGGCTTTCCCCCACTGTTTGGCTTTCAGTTATATGGATCATCTGGTATTGGGGGCCA
6208   GTAGGGCTTTCCCCCACTGTTTGGCTTTCAGTTATATGGATGATGTGGTTCTGGGGGCCA
6209   GCAGGGCTTTCCCCCACTGTATGGCTTTTAGTTATATGGATGATGTGGTTCTGGGGGCCA
6210   GTAGGGCTTTCCCCCACTGTTTGGCTTTCAGTTATATGGATCATCTGGTATTGGGGGCCA
6211   GTAGGGCTTTCCCCCACTGCTTGGCTTTTGGCTATATGGATCATCTGGTATTGGGGGCCA
6212   GCAGGGCTTTCCCCCACTGCTTGGCTTTTAGCTATATGGATCATCTGGTATTGGGGGCCA
6213   GCAGGGCTTTCCCCCACTGTTTGGCTTTCAGTTATATGGATCATTTGGTTTTGGGGGCCA
6214   GTAGGGCTTTCCCCCACTGCTTGGCTTTTGGCTATATGGATCATCTGGTATTGGGGGCCA
6215   GTAGGGCTTTCCCCCACTGTTTGGCTTTCAGTTATATGGATCATCTGGTATTGGGGGCCA 781       790       800       810       820       830       840
                |         |         |         |         |         |         |
HBV    AGTCTGTACAGCATCTTGAGTCCCTTTTTACCGCTGTTACCAATTTTCTTTTGTCTTTGG
CGHV   AATCTGTACAACATCTTGAATCCATTTATACCGCTGTTACCAATTTTCTTTTGTCTTTGG
HWHV   GCACTTCTGAGCATCTTACCGCCATTTATTCCCATATTTGTTCTGTTTTTCTTGATTTGG
WMHV   AGTCTGTTCAGCATCTTGAGTCCCTTCTTGCCTCTGTTACCACTTTTCTTTTGGCTTTGG
6101   AATCTGTACAACATCTTGAGTCCCTTCTTGCCGCTGTTACCAATTTTCTTTTGTCTTTGG
6102   AGTCTGTACAGCATCTTGAGTCCCTTTTTACCGCTGTTACCAATTTTCTTTTGTCTTTGG
6103   AGTCTGTACAGCATCTTGAGTCCCTTTTTACCGCTGTTACCAATTTTCTTTTGTCTTTGG
6104   AATCTGTACAACATCTTGAATCCCTTTTTACCGCTGTTACCAATTTTCTTTTGTCTTTGG
6105   AATCTGTACAACATCTTGAATCCCTTTTTACCGCTGTTACCAATTTTCTTTTGTCTTTGG
6106   AATCTGTACAACATCTTGAATCCATTTATACCGCTGTTACCAATTTTCTTTTGTCTTTGG
6107   AGTCTGTACAGCATCTTGAGTCCCTTTTTACCGCTGTTACCAATTTTCTTTTGGCTTTGG
6108   AGTCTGTTCAGCATCTTGAGTCCCTTCTTGCCTCTGTTACCACTTTTCTTTTGGCTTTGG
6109   AGTCTGTTCAGCATCTTGAGTCCCTTCTTGCCTCTGTTACCACTTTTCTTTTGGCTTTGG
6110   AGTCTGTTCAGCATCTTGAGTCCCTTCTTGCCTCTGTTACCACTTTTCTTTTGGCTTTGG
6111   AATCTGTACAACATCTTGAATCCATTTATACCGCTGTTACCAATTTTCTTTTGTCTTTGG
6201   AATCTGTACAACATCTTGAATCCATTTATACCGCTGTTACCAATTTTCTTTTGTCTTTGG
6202   AGTCTGTACAGCATCTTGAGTCCCTTCTTGCCTCTGTTACCACTTTTCTTTTGGCTTTGG
6203   AGTCTGTACAGCATCTTGAGTCCCTTTTTACCGCTGTTACCAATTTTCTTTTGTCTTTGG
6204   AATCTGTACAACATCTTGAATCCCTTTTTACCGCTGTTACCAATTTTCTTTTGTCTTTGG
6205   AATCTGTACAACATCTTGAATCCCTTTTTACCGCTGTTACCAATTTTCTTTTGTCTTTGG
6206   AGTCTGTACAGCATCTTGAGTCCCTTTTTACCGCTGTTACCAATTTTCTTTTGTCTTTGG
6207   AATCTGTACAACATCTTGAATCCATTTATACCGCTGTTACCAATTTTCTTTTGTCTTTGG
6208   AGTCTGTTCAGCATCTTGAGTCCCTTCTTGCCTCTGTTACCACTTTTCTTTTGGCTTTGG
6209   AGTCTGTTCAGCATCTTGAGTCCCTTCTTGCCTCTGTTACCAATTTTCTTTTGTCTTTGG
```

Figure 33 (continued)

```
6210    AATCTGTACAACATCTTGAATCCATTTATACCGCTGTTACCAATTTTCTTTTGTCTTTGG
6211    AATCTGTACAACATCTTGAATCCCTTTTTACCGCTGTTACCAATTTTCTTTTGTCTTTGG
6212    AATCTGTACAACATCATGAATCCCTTTTTACCGCTGTTACCAATTTTCTTTTGTCTTTGG
6213    AGTCTGTACAGCATCTTGAGTCCCTTTTTACCGCTGTTACCAATTTTCTTTTGTCTTTGG
6214    AATCTGTACAACATCTTGAATCCCTTTTTACCGCTGTTACCAATTTTCTTTTGTCTTTGG
6215    AATCTGTACAACATCTTGAGTCCATTTATACCGCTGTTACCAATTTTCTTTTGTCTTTGG 841       849
         |         |
HBV     GTATACATT
CGHV    GTATACATT
HWHV    GTATACATT
WMHV    GTATACATT
6101    GTATACATT
6102    GTATACATT
6103    GTATACATT
6104    GTATACATT
6105    GTATACATT
6106    GTATACATT
6107    GTATACATT
6108    GTATACATT
6109    GTATACATT
6110    GTATACATT
6111    GTATACATT
6201    GTATACATT
6202    GTATACATT
6203    GTATACATT
6204    GTATACATT
6205    GTATACATT
6206    GTATACATT
6207    GTATACATT
6208    GTATACATT
6209    GTATACATT
6210    GTATACATT
6211    GTATACATT
6212    GTATACATT
6213    GTATACATT
6214    GTATACATT
6215    GTATACATT
```

Figure 34

```
         1         10        20        30        40        50        60
         |         |         |         |         |         |         |
HBV      MQWNSTTFHQTLQDPRVRGLYFPAGGSSSGTVNPVLTTASPLSSIFSRIGDPALNMENIT
CGHV     MQWNSTVFHQALQDPRVRGLYFPVGGSSSGTLNPVPNTASHISSVFSTTGDPAPNMENIT
HWHV     MQWNSTAFHQTLQDPRVRGLYLPAGGSSSGTVNPAPNIASHISSISARTGDPVTNMS--P
WMHV     MQWNSTSFQSYLQNPKVRGLYFPAGGSTSSIVNPVPTTASTTSSSFSTTGVPVSTMDITS
6101     MQWNSTVFHQTLQDPRVGGLYLPAGGSSSGTVNPVLTTASPLSSIFSRIGDPALNMENIT
6102     MQWNSTTFHQTLQDPRVRGLYLPAGGSSSGTVNPAPNTASHISSVFSTTGDPAPNMENIT
6103     MQWNSTAFHQTLQDPRVRGLYLPAGGSSSGTVNPAPNIASHISSISARTGDPAPNMENIT
6104     MQWNSTTFHQTLQDPRVRGLYLPAGGSSSGTVNPAPNIASHISSISARTGDPALNMENIT
6105     MQWNSTTFHQTLQDPRVRGLYLPAGGSSSGTVNPAPNIASHISSISARTGDPALNMENIT
6106     MQWNSTTFHQTLQDPRVRGLYFPAGGSSSGTVNPVLTTASPLSSIFSRIGDPALNMENIT
6107     MQWNSTAFHQTLQDPRVRGLYLPAGGSSSGTVNPAPNIASPLSSIFSTTGDPAPNMENIT
6108     MQWNSTAFHQTLQDPRVRGLYLPAGGSSSGTVNPAPNIASHISSISARTGDPVTNMS--P
6109     MQWNSTAFHQTLQDPRVRGLYLPAGGSSSGTVNPAPNIASHISSISARTGDPVTNMS--P
6110     MQWNSTAFHQTLQDPRVRGLYLPAGGSSSGTVNPAPNIASHISSISARTGDPVTNMS--P
6111     MQWNSTAFHQTLQDPRVRGLYFPVGGSSSGTVNPAPNIASPLSSIFSRIGDPALNMENIT
6201     MQWNSTAFHQTLQDPRVRGLYLPAGGSSSGTVNPAPNIASHISSISARIGDPALNMGNIT
6202     MQWNSTAFHQTLQDPRVRGLYLPAGGSSSGTVNPAPNIASHISSISARIRDPALNMENIA
6203     MQWNSTTFHQTLQDPRVRGLYLPAGGSSSGTVNPAPNIASHISSISARTGDPALNMENIT
6204     MQWNSTTFHQTLQDPRVRGLYLPAGGSSSGTVNPAPNIASHISSISARTGDPALNMENIT
6205     MQWNSTTFHQTLQDPRVRGLYLPAGGSSSGTVNPAPNTASHISSVFSTTGDPAPNMENIT
6206     MQWNSTAFHQTLQDPRVRGLYLPAGGSSSGTVNPAPNIASHISSISARTGDPAPNMENIT
6207     MQWNSTTFHQTLQDPRVRGLYFPAGGSSSGTVNPVLTTASPVSSIFSRIGDPALNMENIT
6208     MQWNSTTFHQTLQDPRVRGLYFPAGGSSSGTVNPVLTTASPLSSIFSRIGDPALNMENIT
6209     MQWNSTAFHQTLQDPRVRGLYLPAGGSSSGTVNPAPNIASHISSISARIGDPALNMENIT
6210     MQWNSTAFHQTLQDPRVRGLYLPAGGSSSGTVNPAPNIASPLSSIFSTTGDPALNMENIT
6211     MQWNSTTFHQTLQDPRVRGLYLPAGGSSSGTVNPAPNTASHISSVFSTTGDPAPNMENIT
6212     MQWNSTAFHQTLQDPRVRGLYLPAGGSSSGTVNPAPNIASHISSISARIGDPALNMENIT
6213     MQWNSTAFHQTLQDPRVRGLYLPAGGSSSGTVNPAPNTASHISSVFSTTGDPAPNMENIT
6214     MQWNSTAFHQTLQDPRVRGLYLPAGGSSSGTVNPAPNIASSISARTGDPALNMENIT
6215     MQWNSTAFHQTLQDPRVRGLYLPAGGSSSGTVNPAPNIASHISSISARTGDPVTNMS--P 61        70        80        90        100       110       120
         |         |         |         |         |         |         |
HBV      SGFLGPLLVLQAGFFLLTRILTIPQSLDSWWTSLNFLGGTTVCLGQNSQSPTSNHSPTSC
CGHV     SGFLGPLLVLQAGFFLLTKILTIPQSLDSWWTSLNFLGGAPVCPGQNSQSPTSNHSPTSC
HWHV     SSLLGLLAGLQVVYFLWTKILTIAQNLDWWTSLSFPGGIPECTGQNSQFQTCKHLPTSC
WMHV     SGFLGPLLALQAVFFLLTKILTMPQSLDSWTSLNFLGGTPACPGLNSQSPTSSHSPTCC
6101     SGFLGPLLVLQAGFFLMTKILTMPQSLDSWWTSLNFLGRAPVCPGQNSQSPTSNHSPTSC
6102     SGFLGPLLVLQAGFFLLTKILTMPQSLDSWTSLNFLGGTPACLGQNSQSPTSNHSPTSC
6103     SGFLGPLLVLQAVFFLLTRILTIPQSLDSWWTSLNFLGGTTVCPGQNSQSPTSNHSPTSC
6104     SGFLGPLLVLQAGFFLLTRILTIPQSLDSWWTSLNFLGGTTVCLGLNSQSPTSNHSPTSC
6105     SGFLGPLLVLQAGFFLLTRILTIPQSLDSWWTSLNFLGGTTVCLGLNSQSPTSNHSPTSC
6106     SGFLGPLLVLQAGFFLLTRILTIPQSLDSLWTSLSFPGGIPECTGQNSQSPTSNHSPTSC
6107     SGFLGPLLVLQAGFFLLTRILTIPQSLDSWWTSLNFLGGAPVCLGQNSQSPTSNHSPTSC
6108     SSLLGLLAGLQVVYFLWTKILTIPQSLDSWWTSLNFLGGAPVCPGQNSQSPTSNHSPTSC
6109     SSLLGLLAGLQVVYFLWTKILTIPQSLDSWWTSLNFLGGAPVCPGQNSQSPTSNHSPTSC
6110     SSLLGLLAGLQVVYFLWTKILTIPQSLDSWWTSLNFLGGAPVCPGQNSQSPTSNHSPTSC
6111     SGFLGPLLVLQAGFFLLTKVLTIPQSLDSWWTSLNFLGGTTVCLGQNSQSPTSNHSPTSC
6201     SGFLGPLLVLQAGFFLMTKILTMPQSLDSWWTSLNFLGGTTVRPGQNSQSPTSNHSPTSC
6202     SGFLGPLLALQAVFFLLTKILTMPQSLDSWWTSLNFLGGTTVCLGQNSQSPTSNHSPTSC
6203     SGFLGPLLVLQAGFFLLTRILTIPQSLDSWWTSLNFLGGAPVCPGQNSQSPTSNHSPTSC
6204     SGFLGPLLVLQAGFFLLTRILTIPQSLDSWWTSLNFLGGTTVCLGLNSQSPTSNHSPTSC
6205     SGFLGPLLVLQAGFFLLTKILTMPQSLDSLWTSLNFLGGTPACLGQNSQSPTPNHSPTSC
```

Figure 34 (continued)

```
6206    SGFLGPLLVLQAVFFLLTRILTIPQSLDSWWTSLNFLGGTPVCPGQNSQSPTSNHSPTSC
6207    SGFLGPLLVLQAGFFLLTRILTIPQSLDSLWTSLSFPRGIPECTGQNSQSPTSNHSPTSC
6208    SGFLGPLLVLQAGFFLLTRILTIPQSLDSLWTSLSFPGGIPECTGQNSQSPTSNHSPTSC
6209    SGFLGPLLALQAVFFLLTKILTMPQSLDSWWTSLNFLGGTTVCLGLNSQSPTSNHSPTSC
6210    SGFLGPLLVLQAGFFLLTRILTIPQSLDSWWTSLNFLGGAPVCLGQNSQSPTSNHSPTSC
6211    SGFLGPLLVLQAGFFLLTKILTMPQSLDSLWTSLNFLGGTPACLGQNSQSPTSNHSPTSC
6212    SGFLGPLLALQAVFFLLTKILTMPQSLDSWWTSLNFLGGTTVCLGQNSQSPTSNHSPTSC
6213    SGFLGPLLVLQAGFFLLTKILTMPQSLDSLWTSLNFLGGTPACLGQNSQSPTSNHSPTSC
6214    SGFLGPLLVLQAGFFLLTRILTIPQSLDSWWTSLNFLGGTTVCLGLNSQSPTSNHSPTSC
6215    SSLLGLLAGLQVVYPLWTKILTIPQSLDSWWTSLNFLGGAPVCPGQNSQSPTSNHSPTSC 121       130       140       150       160       170       180
         |         |         |         |         |         |         |
HBV     PPTCPGYRWMCLRRFIIFLFILLLCLIFLLVLLDYQGMLPVCPLIPGSS---TTSTGPCRT
CGHV    PPICPGYRWMCLRRFIIFLFILLLCLIFLLVLLDYRGMLPVCPLLPGSS---TTSTGPCKT
HWHV    PPTCNGFRWMYLRRFIIYLLVLLLCLIFLLVLLDWKGLIPVCPLQPTTE--TTVN--CRQ
WMHV    PPTCPGYRWMCLRPSIIFLFILLLCLIFLLVLLDYQGMLPVCPLLPTVTGTTTTTGPCRT
6101    PPICPGYRWMCLRRFIIFLFILLLCLIFLLVLLDYRGMLPVCPLLPGSS---TTSTGPCKT
6102    PPTCPGYRWMCLRRFIIFLFILLLCLIFLLVLLDYRGMLPVCPLIPGSS---TTSTGPCRT
6103    PPTCPGYRWMCLRRFIIYLLVLLLCLIFLLVLLDYQGMLPVCPLIPGSS---TTSTGPCKT
6104    PPTCPGYRWMCLRRFIIFLFILLLCLIFLLVLLDYQGMLPVCPLIPGSS---TTSTGPCKT
6105    PPTCPGYRWMCLRRFIIFLFILLLCLIFLLVLLDYQGMLPVCPLIPGSS---TTSTGPCKT
6106    PPTCPGYRWMCLRRFIIFLFILLLCLIFLLVLLDYRGMLPVCPLLPGSS---TTSTGPCRT
6107    PPTCPGYRWMPLRRFIIFLFILLLCLIFLLVLLDYRGMLPVCPLIPGSS---TTGTGPCRT
6108    PPICPGYRWMCLRRFIIFLFILLLCLIFLLVLLDYRGMLPVCPLLPGSS---TTSTGPCKT
6109    PPICPGYRWMCLRPFIIFLFILLLCLIFLLVLLDYQGMLPVCPLIPGSS---TTSTGPCKT
6110    PPICPGYRWMCLRRFIIFLFILLLCLIFLLVLLDYQGMLPVCPLIPGSS---TTSTGPCKT
6111    PPTCPGYRWMCLRPFIIFLFILLLCLIFLLVLLDYRGMLPVCPLIPGSS---TTSTGPCRT
6201    PPTCPGYRWMCLRRFIIFLFILLLCLIFLLVLLDYRGMLPVCPLLPGSS---TTSTGPCRT
6202    PPTCPGYRWMCLRRFIIFLFILLLCLIFLLVLLDYRGMLPVCPLIPGSS---TTSTGPCKT
6203    PPICPGYRWMCLRPFIIFLFILLLCLIFLLVLLDYRGMLPVCPLLPGSS---TTSTGPCRT
6204    PPTCPGYRWMCLRRFIIFLFILLLCLIFLLVLLDYQGMLPVCPLIPGSS---TTSTGPCKT
6205    PPTCPGYRWMCLRRFIIFLFILLLCLIFLLVLLDYRGMLPVCPLLPGSS---TTSTGPCKT
6206    PPTCPGYRWMCLRRFIIFLFILLLCLIFLLVLLDYQGMLPVCPLIPGSS---TTSTGPCKT
6207    PPTCPGYRWMCLRPFIIFLFILLLCLIFLLVLLDYRGMLPVCPLLPGSS---TTSTGPCRT
6208    PPTCPGYRWMCLRRFIIFLFILLLCLIFLLVLLDYRGMLPVCPLLPGSS---TTSTGPCRT
6209    PPTCPGYRWMCLRPFIIFLFILLLCLIFLLVLLDYRGMLPVCPLLPGSS---TTSTGPCRT
6210    PPTCPGYRWMCLRRFIIFLFILLLCLIFLLVLLDYRGMLPVCPLLPGSS---TTSTGPCRT
6211    PPTCPGHRWMCLRRFIIFLFILLLCLIFLLVLLDYRGMLPVCPLIPGSS---TTSTGPCKT
6212    PPTCPGYRWMCLRPFIIFLFILLLCLIFLLVLLDYRGMLPVCPLIPGSS---TTSTGPCKT
6213    PPTCPGYRWMCLRRFIIFLFILLLCLIFLLVLLDYRGMLPVCPLLPGSS---TTSTGPCKT
6214    PPTCPGYRWMCLRPFIIFLFILLLCLIFLLVLLDYQGMLPVCPLIPGSS---TTSTGPCKT
6215    PPTCPGYRWMCLRRFIIFLFILLLCLIFLLVLLDYRGMLPVCPLLPGSS---TTSTGPCRT 181       190       200       210       220       230       240
         |         |         |         |         |         |         |
HBV     CMTTAQGTSMYPSCCCTKPSDGNCTCIPIPSSWAFGKFLWEWASARFSWLSLLVPFVQWF
CGHV    CTIPAQGTSLIPSCCCTRPSDGNCTCIPIPSSWAFAKFLWEWASVRFSWLSLLAPFVQRF
HWHV    CTISAQDMYTPPYCCCLKPTAGNCTCWPIPSSWALGNYLWEWALAPFSWLNLLVPLLQWL
WMHV    CTPIVPGISSYPSCCCTKPTDGNCTCIPIPSSWAFAKFLWDWALARFSWLNSLLPFVQWF
6101    CTIPAQGTSLIPSCCCTRPSDGNCTCIPIPSSWAFAKFLWEWASVRFSWLSLLAPFVQRF
6102    CMTTAQGTSMYPSCCCTKPSDGNCTCIPIPSSWAFGKFLWDWASARFSWLSLLVPFVQRF
6103    CMTTAQGTSMYPSCCCTKPSDGNCTCIPIPSSWAFGKFLWEWASARFSWLSLLVPFVQRF
6104    CMTTPQGTSMYPSCCCTKPSDGNCTCIPIPSSWAFGKFLWEWASARFSWLSLLVPFVQWF
6105    CMTTPQGTSMYPSCCCTKPSDGNCTCIPIPSSWAFGKFLWEWASARFSWLSLLVPFVQWF
6106    CMTTAQGTSMYPSCCCTKPSDGNCTCIPIPSSWAFAKFLWEWASARFSWLSLLVPFVQWF
6107    CMTTAQGTSMYPSCCCTKPSDGNCTCIPIPSSWAFGKFLWEWASARFSWLSLLVPFVQWF
```

Figure 34 (continued)

```
6108  CMTTPQGTSMYPSCCCTKPSDGNCTCIPIPSSWAFGKFLWEWASVRFSWLSLLAPFVQRF
6109  CMTTPQGTSMYPSCCCTKPSDGNCTCIPIPSSWAFGKFLWEWASVRFSWLSLLAPFVQRF
6110  CMTTPQGTSMYPSCCCTKPSDGNCTCIPIPSSWAFGKFLWEWASVRFSWLSLLAPFVQRF
6111  CMTTAQGTSMYPSCCCTKPSDGNCTCIPIPSSWAFGKFLWEWASARFSWLSLLVPFVQWF
6201  CMTTAQGTSMYPSCCCTKPSDGNCTCIPIPSSWAFAKFLWEWASARFSWLSLLVPFVQWF
6202  CMTTAQGTSMYPSCCCTKPSDGNCTCIPIPSSWAFAKFLWEWASARFSWLSLLVPFVQWF
6203  CMTTAQGTSMYPSCCCTKPSDGSCTCIPIPSSWAFAKFLWEWASARFSWLSLLVPFVQWF
6204  CMTTPQGTSMYPSCCCTKPSDGNCTCIPIPSSWAFGKFLWEWASARFSWLSLLVPFVQWF
6205  CMTTPQGTSMYPSCCCTKPSDGNCTCIPIPSSWAFGKFLWEWASARFSWLSLLVPFVQWF
6206  CMTTPQGTSMYPSCCCTKPSDGNCTCIPIPSSWAFGKFLWEWASARFSWLSLLVPFVQRF
6207  CMTTAQGTSMYPSCCCTKPSDGNCTCIPIPSSWAFAKFLWEWASARFSWLSLLVPFVQWF
6208  CMTTAQGTSMYPSCCCTKPSDGNCTCIPIPSSWAFGKFLWEWASVRFSWLSLLAPFVQRF
6209  CMTTAQGTSMYPSCCCTKPSDGSCTCIPIPSSWAFGKFLWEWASVRFSWLSLLVPFVQWF
6210  CMTAAQGTSMYPSCCCTKPSDGNCTCIPIPSSWAFAKFLWEWASARFSWLSLLVPFVQWF
6211  CMTTPQGTSMYPSCCCTKPSDGNCTCIPIPSSWAFGKFLWEWASARFSWLSLLVPFVQWF
6212  CMTTAQGTSMYPSCCCTKPSDGNCTCIPIPSSWAFGKFLWEWASARFSWLSLLAPFVQRF
6213  CTIPAQGTSLIPSCCCTKPSDGNCTCIPIPSSWAFAKFLWEWASARFSWLSLLVPFVQRF
6214  CMTTPQGTSMYPSCCCTKPSDGNCTCIPIPSSWAFGKFLWEWASARFSWLSLLVPFVQWF
6215  CMTTAQGTSMYPSCCCTKPSDGNCTCIPIPSSWAFAKFLWEWASARFSWLSLLVPFVQWF 241       250       260       270       280
              |         |         |         |         |
HBV   VGLSPTVWLSVIWMMWYWGPSLYSILSPFLPLLPIFFCLWVYI
CGHV  AGLSPTAWLLAIWIIWYWGPNLYNILNPFIPLLPIFFCLWVYI
HWHV  GGISLIAWFLLIWMIWFWGPALLSILPPFIPIFVLFFLIWVYI
WMHV  AGLSPTVWLLVIWMMWFWGPSLFSILSPFLPLLPLFFWLWVYI
6101  AGLSPTAWLLAIWIIWYWGPNLYNILSPFLPLLPIFFCLWVYI
6102  AGLSPTAWLSVIWMMWYWGPSLYSILSPFLPLLPIFFCLWVYI
6103  AGLSPTVWLSVIWMIWFWGPSLYSILSPFLPLLPIFFCLWVYI
6104  VGLSPTAWLLAIWIIWYWGPNLYNILNPFLPLLPIFFCLWVYI
6105  VGLSPTAWLLAIWIIWYWGPNLYNILNPFLPLLPIFFCLWVYI
6106  VGLSPTVWLSVIWIIWYWGPNLYNILNPFIPLLPIFFCLWVYI
6107  VGLSPAVWLSVIWMMWYWGPSLYSILSPFLPLLPIFFWLWVYI
6108  VGLSPTVWLSVIWMMWFWGPSLFSILSPFLPLLPLFFWLWVYI
6109  VGLSPTVWLSVIWMMWFWGPSLFSILSPFLPLLPLFFWLWVYI
6110  VGLSPTVWLSVIWMMWFWGPSLFSILSPFLPLLPLFFWLWVYI
6111  VGLSPTAWLLAIWIIWYWGPNLYNILNPFIPLLPIFFCLWVYI
6201  VGLSPTVWLSVIWIIWYWGPNLYNILNPFIPLLPIFFCLWVYI
6202  VGLSPTVWLSVIWMMWYWGPSLYSILSPFLPLLPLFFWLWVYI
6203  VGLSPAVWLSVIWMIWFWGPSLYSILSPFLPLLPIFFWLWVYI
6204  VGLSPTAWLLAIWIIWYWGPNLYNILNPFLPLLPIFFCLWVYI
6205  VGLSPTAWLLAIWIIWYWGPNLYNILNPFLPLLPIFFCLWVYI
6206  AGLSPTVWLSVIWMIWFWGPSLYSILSPFLPLLPIFFCLWVYI
6207  VGLSPTVWLSVIWIIWYWGPNLYNILNPFIPLLPIFFCLWVYI
6208  VGLSPTVWLSVIWMMWFWGPSLFSILSPFLPLLPLFFWLWVYI
6209  AGLSPTVWLLVIWMMWFWGPSLFSILSPFLPLLPIFFCLWVYI
6210  VGLSPTVWLSVIWIIWYWGPNLYNILNPFIPLLPIFFCLWVYI
6211  VGLSPTAWLLAIWIIWYWGPNLYNILNPFLPLLPIFFCLWVYI
6212  AGLSPTAWLLAIWIIWYWGPNLYNIMNPFLPLLPIFFCLWVYI
6213  AGLSPTVWLSVIWMIWFWGPSLYSILSPFLPLLPIFFCLWVYI
6214  VGLSPTAWLLAIWIIWYWGPNLYNILNPFLPLLPIFFCLWVYI
6215  VGLSPTVWLSVIWIIWYWGPNLYNILSPFIPLLPIFFCLWVYI
```

Figure 35

(SEQ ID NO:59)

WT Hepatitis amino acid sequence in GREY
Summary of amino acid sustitutions from shuffled clones in BLACK
Regions of interested are underlined

```
...............PreS2 B epitope....................PreS2..................
MQWNSTTFHQTLQDPRVRGLYFPAGGSSSGTVNPVLTTASPLSSIFSRIGD
    A              G    L V          APNI   HI   VSATTR
    V                                       V ............        TM1              CTL Epitope
PALNMENITSGFLGPLLVLQAGFFLLTRILTIPQSLDSWWTSLNFLGGTTV
  VP   S---P  SL   L  AA   VVY  W KV  M        L     S  PRRAPA
   T    G    A           G       M                      I E TM2
CLGQNSQSPTSNHSPTSCPPTCPGYRWMCLRRFIIFLFILLLCLIFLLVLL
 RP L    P   P         SI   HH  R W    Y LV
  T a-loop
DYQGMLPVCPLIPGSSTTSTGPCRTCMTTAQGTSMYPSCCCTKPSDGNCTC
 R V    PL      G     K  TIPP    LI             S
                          A TM3                        TM4
IPIPSSWAFGKFLWEWASARFSWLSLLVPFVQWFVGLSPTVWLSVIWMMWY
     A    D  V          A    R A        AA LAT II F

WGPSLYSILSPFLPLLPIFFCLWVYI*
   N  FN MN  I      L   W
```

HEPATITIS B VIRUS VACCINES

CROSS REFERENCE TO RELATED APPLICATIONS

This application claims the benefit of U.S. Provisional Application Ser. No. 61/785,838, filed Mar. 14, 2013. The disclosure of the prior application is considered part of (and is incorporated by reference in) the disclosure of this application.

BACKGROUND

1. Technical Field

This document relates to methods and materials for producing immune responses against hepatitis B viruses. For example, this document provides vaccines (e.g., nucleic acid vaccines, virus-like particle vaccines, and polypeptide vaccines) capable of being administered to mammals (e.g., humans) under conditions that induce production of immune responses against hepatitis B viruses.

2. Background Information

Hepatitis B virus (HBV) is a hepadnavirus that causes an inflammatory illness of the liver. About a third of the world population is infected at one point in their lives, and about 350 million people are chronic carriers. The virus can be transmitted by exposure to infectious blood or body fluids. The acute illness causes liver inflammation, vomiting, jaundice, and, in rare cases, death. Chronic hepatitis B infections may cause cirrhosis and liver cancer.

SUMMARY

This document provides methods and materials for producing immune responses against hepatitis B viruses. For example, this document provides vaccines (e.g., nucleic acid vaccines, virus-like particle vaccines, and polypeptide vaccines) capable of being administered to mammals (e.g., humans) under conditions that induce production of immune responses against hepatitis B viruses as well as methods for producing immune responses against hepatitis B viruses within a mammal (e.g., a human).

As described herein, polypeptides having the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or a sequence at least about 86, 87, 88, 89, 90, 91, 92, 93, 94, 95, 96, 97, 98, 99, or 100 percent identical to such as sequence) can be produced and formulated into a vaccine preparation having the ability to produce an immune response against hepatitis B viruses when administered to a mammal (e.g., a human). Such vaccine preparations can be administered to a mammal prior to the mammal being exposed to hepatitis B viruses. In such cases, the administered vaccine preparation can provide increased protection against hepatitis B virus infection. In some cases, such vaccine preparations can be administered to a mammal after the mammal is infected with hepatitis B virus (e.g., an acutely hepatitis B virus infected or chronically hepatitis B virus infected mammal). In such cases, administration of the vaccine preparation can be used to treat the hepatitis B virus infection. For example, administration of a vaccine preparation provided herein to a mammal infected with hepatitis B virus can result in a reduction in hepatitis B viral load, a reduction in the severity of the symptoms of the hepatitis B virus infection, a reduction in the degree of liver cirrhosis, a reduction in the incidence of hepatocellular cancer, or a clearance of the hepatitis B virus from the liver.

In some cases, a polypeptide provided herein (e.g., a polypeptide having the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58, or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58) can be formulated into virus-like particles that can be used as vaccine preparations having the ability to produce an immune response against hepatitis B viruses when administered to a mammal (e.g., a human). The vaccine preparations containing such virus-like particles can be administered to a mammal prior to the mammal being exposed to hepatitis B viruses. In such cases, the administered vaccine preparation containing virus-like particles can provide increased protection against hepatitis B virus infection. In some cases, a vaccine preparation containing a virus-like particle provided herein can be administered to a mammal after the mammal is infected with hepatitis B virus (e.g., an acutely hepatitis B virus infected or chronically hepatitis B virus infected mammal). In such cases, administration of the vaccine preparation containing a virus-like particle can be used to treat the hepatitis B virus infection. For example, administration of a vaccine preparation containing a virus-like particle provided herein to a mammal infected with hepatitis B virus can result in a reduction in hepatitis B viral load, a reduction in the severity of the symptoms of the hepatitis B virus infection, a reduction in the degree of liver cirrhosis, a reduction in the incidence of hepatocellular cancer, or a clearance of the hepatitis B virus from the liver.

As also described herein, nucleic acid molecules encoding a polypeptide having the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or a sequence at least about 86, 87, 88, 89, 90, 91, 92, 93, 94, 95, 96, 97, 98, 99, or 100 percent identical to such as sequence) can be obtained and formulated into a nucleic acid vaccine preparation having the ability to express the encoded polypeptide and produce an immune response against hepatitis B viruses when administered to a mammal (e.g., a human). Such nucleic acid vaccine preparations can be administered to a mammal prior to the mammal being exposed to hepatitis B viruses. In such cases, the administered nucleic acid vaccine preparation can provide increased protection against hepatitis B virus infection. In some cases, such nucleic acid vaccine preparations can be administered to a mammal after the mammal is infected with hepatitis B virus (e.g., an acutely hepatitis B virus infected or chronically hepatitis B virus infected mammal). In such cases, administration of the nucleic acid vaccine preparation can be used to treat the hepatitis B virus infection. For example, administration of a nucleic acid vaccine preparation provided herein to a mammal infected with hepatitis B virus can result in a reduction in hepatitis B viral load, a reduction in the severity of the symptoms of the hepatitis B virus infection, a reduction in the degree of liver cirrhosis, a reduction in the incidence of hepatocellular cancer, or a clearance of the hepatitis B virus from the liver.

Having the ability to use the vaccine preparations provided herein produce immune responses against hepatitis B viruses can allow clinicians to provide their patients with increased protection against hepatitis B virus infections. In addition, the vaccine preparations provided herein can allow clinicians to treat patients previously infected with hepatitis B virus.

In general, one aspect of this document features a polypeptide comprising an amino acid sequence that is at least 97 percent identical (e.g., at least 98, 99, or 100 percent identical) to the amino acid sequence set forth in SEQ ID NO:10.

In another aspect, this document features a polypeptide comprising an amino acid sequence that is at least 96 percent identical (e.g., at least 97, 98, 99, or 100 percent identical) to the amino acid sequence set forth in SEQ ID NO:12.

In another aspect, this document features a polypeptide comprising an amino acid sequence that is at least 96 percent identical (e.g., at least 97, 98, 99, or 100 percent identical) to the amino acid sequence set forth in SEQ ID NO:14.

In another aspect, this document features a polypeptide comprising an amino acid sequence that is at least 95 percent identical (e.g., at least 96, 97, 98, 99, or 100 percent identical) to the amino acid sequence set forth in SEQ ID NO:16.

In another aspect, this document features a polypeptide comprising an amino acid sequence that is at least 97 percent identical (e.g., at least 98, 99, or 100 percent identical) to the amino acid sequence set forth in SEQ ID NO:18.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:20.

In another aspect, this document features a polypeptide comprising an amino acid sequence that is at least 97 percent identical (e.g., at least 98, 99, or 100 percent identical) to the amino acid sequence set forth in SEQ ID NO:22.

In another aspect, this document features a polypeptide comprising an amino acid sequence that is at least 89 percent identical (e.g., at least 90, 91, 92, 93, 94, 95, 96, 97, 98, 99, or 100 percent identical) to the amino acid sequence set forth in SEQ ID NO:24.

In another aspect, this document features a polypeptide comprising an amino acid sequence that is at least 89 percent identical (e.g., at least 90, 91, 92, 93, 94, 95, 96, 97, 98, 99, or 100 percent identical) to the amino acid sequence set forth in SEQ ID NO:26.

In another aspect, this document features a polypeptide comprising an amino acid sequence that is at least 95 percent identical (e.g., at least 94, 95, 96, 97, 98, 99, or 100 percent identical) to the amino acid sequence set forth in SEQ ID NO:28.

In another aspect, this document features a polypeptide comprising an amino acid sequence that is at least 94 percent identical (e.g., at least 94, 95, 96, 97, 98, 99, or 100 percent identical) to the amino acid sequence set forth in SEQ ID NO:30.

In another aspect, this document features a polypeptide comprising an amino acid sequence that is at least 96 percent identical (e.g., at least 97, 98, 99, or 100 percent identical) to the amino acid sequence set forth in SEQ ID NO:32.

In another aspect, this document features a polypeptide comprising an amino acid sequence that is at least 96 percent identical (e.g., at least 97, 98, 99, or 100 percent identical) to the amino acid sequence set forth in SEQ ID NO:34.

In another aspect, this document features a polypeptide comprising an amino acid sequence that is at least 96 percent identical (e.g., at least 97, 98, 99, or 100 percent identical) to the amino acid sequence set forth in SEQ ID NO:36.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:38.

In another aspect, this document features a polypeptide comprising an amino acid sequence that is at least 97 percent identical (e.g., at least 98, 99, or 100 percent identical) to the amino acid sequence set forth in SEQ ID NO:40.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:42.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:44.

In another aspect, this document features a polypeptide comprising an amino acid sequence that is at least 95 percent identical (e.g., at least 96, 97, 98, 99, or 100 percent identical) to the amino acid sequence set forth in SEQ ID NO:46.

In another aspect, this document features a polypeptide comprising an amino acid sequence that is at least 96 percent identical (e.g., at least 97, 98, 99, or 100 percent identical) to the amino acid sequence set forth in SEQ ID NO:48.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:50.

In another aspect, this document features a polypeptide comprising an amino acid sequence that is at least 93 percent identical (e.g., at least 94, 95, 96, 97, 98, 99, or 100 percent identical) to the amino acid sequence set forth in SEQ ID NO:52.

In another aspect, this document features a polypeptide comprising an amino acid sequence that is at least 92 percent identical (e.g., at least 93, 94, 95, 96, 97, 98, 99, or 100 percent identical) to the amino acid sequence set forth in SEQ ID NO:54.

In another aspect, this document features a polypeptide comprising an amino acid sequence that is at least 86 percent identical (e.g., at least 87, 88, 89, 90, 91, 92, 93, 94, 95, 96, 97, 98, 99, or 100 percent identical) to the amino acid sequence set forth in SEQ ID NO:56.

In another aspect, this document features a polypeptide comprising an amino acid sequence that is at least 89 percent identical (e.g., at least 90, 91, 92, 93, 94, 95, 96, 97, 98, 99, or 100 percent identical) to the amino acid sequence set forth in SEQ ID NO:58.

Any one of the polypeptides described in the above 25 paragraphs can comprise the ability to induce an immune response against a hepatitis B virus when the polypeptide is administered to a mammal. In some cases, any one of the polypeptides described in the above 25 paragraphs can be a fusion polypeptide comprising a second amino acid sequence. The second amino acid sequence can encode a tag selected from the group consisting of GST, FLAG, GFP, and c-myc. The second amino acid sequence can encode a cytokine selected from the group consisting of GM-CSF, IL-2, and IL-12. The polypeptide can be substantially pure. The polypeptide can be an isolated polypeptide.

In another aspect, this document features a virus-like particle comprising one or more polypeptides selected from the group consisting of the polypeptides described in the above said 25 paragraphs. The virus-like particle can comprise one polypeptide selected from the group. The virus-like particle can comprise two, three, four, or five different polypeptides selected from the group. The virus-like particle can comprise the ability to induce an immune response against a hepatitis B virus when the particle is administered to a mammal.

In another aspect, this document features a vaccine preparation comprising one or more polypeptides selected from the group consisting of the polypeptides described in the above said 25 paragraphs. The vaccine preparation can comprise one polypeptide selected from the group. The vaccine preparation can comprise two, three, four, or five different polypeptides selected from the group. The vaccine preparation can comprise the ability to induce an immune response against a hepatitis B virus when the vaccine preparation is administered to a mammal. The vaccine preparation can comprise an adjuvant. The adjuvant can be selected from the group consisting of aluminum-based compounds, Montanide ISA 51, Montanide ISA 720, and CpG oligodeoxynucleotides. The adjuvant can comprise alum or $Al_2O_3$.

In another aspect, this document features a nucleic acid molecule comprising a nucleic acid sequence encoding a polypeptide selected from the group consisting of the polypeptides described in the above said 25 paragraphs. The nucleic acid molecule can comprise a promoter sequence operably linked to the nucleic acid sequence. The nucleic acid molecule can be a vector. The vector can be a plasmid. The vector can be a viral vector. The viral vector can be selected from the group consisting of adenoviral vectors, adeno-associated virus vectors, and vaccinia viral vectors.

In another aspect, this document features a vaccine preparation comprising one or more nucleic acid molecules. The nucleic acid molecule comprises a nucleic acid sequence encoding a polypeptide selected from the group consisting of the polypeptides described in the above said 25 paragraphs. The nucleic acid molecule can comprise a promoter sequence operably linked to the nucleic acid sequence. The nucleic acid molecule can be a vector. The vector can be a plasmid. The vector can be a viral vector. The viral vector can be selected from the group consisting of adenoviral vectors, adeno-associated virus vectors, and vaccinia viral vectors. The vaccine preparation can comprise a nucleic acid molecule comprising a nucleic acid sequence encoding one polypeptide selected from the group. The vaccine preparation can comprise one or more nucleic acid molecules comprising a nucleic acid sequence encoding two, three, four, or five different polypeptides selected from the group. The vaccine preparation can comprise the ability to induce an immune response against a hepatitis B virus when the vaccine preparation is administered to a mammal and the polypeptide is expressed within the mammal. The vaccine preparation can comprise an adjuvant. The adjuvant can be selected from the group consisting of aluminum-based compounds, Montanide ISA 51, Montanide ISA 720, and CpG oligodeoxynucleotides. The adjuvant can comprise alum or $Al_2O_3$.

In another aspect, this document features a method for inducing an immune response against a hepatitis B virus within a mammal. The method comprises administering a vaccine preparation to the mammal. The vaccine preparation comprises (a) one or more polypeptides selected from the group consisting of the polypeptides described in the above said 25 paragraphs, (b) one or more virus-like particles comprising one or more polypeptides selected from the group consisting of the polypeptides described in the above said 25 paragraphs, or (c) one or more nucleic acid molecules comprising a nucleic acid sequence encoding a polypeptide selected from the group consisting of the polypeptides described in the above said 25 paragraphs. The mammal can be a human. The mammal can be a human not previously infected with a hepatitis B virus. The mammal can be a human acutely infected with a hepatitis B virus. The mammal can be a human chronically infected with a hepatitis B virus. The immune response can comprise the production of anti-hepatitis B virus antibodies. The method can comprise administering a second vaccine preparation to the mammal after the step of administering the vaccine preparation to the mammal, wherein the second vaccine preparation comprises an hepatitis B virus antigen. The method can comprise administering a second vaccine preparation to the mammal after the step of administering the vaccine preparation to the mammal, wherein the second vaccine preparation comprises (a) one or more polypeptides selected from the group consisting of the polypeptides described in the above said 25 paragraphs, (b) one or more virus-like particles comprising one or more polypeptides selected from the group consisting of the polypeptides described in the above said 25 paragraphs, or (c) one or more nucleic acid molecules comprising a nucleic acid sequence encoding a polypeptide selected from the group consisting of the polypeptides described in the above said 25 paragraphs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 2 shows the positive (+) strain oligonucleotide sequences used to hold the HBV "a" loop sequence constant during DNA shuffling. A restriction endonuclease BsrB I site sequence (CCGCTC) was introduced, and a BspM I site sequence (ACCTGCN4) was knocked out by the two conservative changes shown in lower case (t and c). These altered restriction sites were engineered into the oligonucleotides to enable a rapid evaluation of oligo incorporation by restriction analysis. The conserved 30 nucleotides from the AYW 'a' epitope loop are shown above the dashed line and underlined in the sequences below the dashed line. All primers are positive sense as indicated by (+). Primers shown: chibbon (+) primer (chimpanzee/gibbon); WM (+) primer (woolly monkey); WD (+) primer (woodchuck).

FIG. 4 contains a listing of the nucleic acid sequence and amino acid sequence for one of the human parental clone used in the initial shuffling.

FIG. 5 contains a listing of the nucleic acid sequence and amino acid sequence for one of the woolly monkey parental clone used in the initial shuffling.

FIG. 6 contains a listing of the nucleic acid sequence and amino acid sequence for one of the human/woodchuck parental clone used in the initial shuffling.

FIG. 7 contains a listing of the nucleic acid sequence and amino acid sequence for one of the composite chimpanzee-gibbon parental clone used in the initial shuffling.

FIG. 8 contains a listing of the nucleic acid sequence and amino acid sequence for clone 6101 obtained from the initial shuffling.

FIG. 9 contains a listing of the nucleic acid sequence and amino acid sequence for clone 6102 obtained from the initial shuffling.

FIG. 10 contains a listing of the nucleic acid sequence and amino acid sequence for clone 6103 obtained from the initial shuffling.

FIG. 11 contains a listing of the nucleic acid sequence and amino acid sequence for clone 6104 obtained from the initial shuffling.

FIG. 12 contains a listing of the nucleic acid sequence and amino acid sequence for clone 6105 obtained from the initial shuffling.

FIG. 13 contains a listing of the nucleic acid sequence and amino acid sequence for clone 6106 obtained from the initial shuffling.

FIG. 14 contains a listing of the nucleic acid sequence and amino acid sequence for clone 6107 obtained from the initial shuffling.

FIG. 15 contains a listing of the nucleic acid sequence and amino acid sequence for clone 6108 obtained from the initial shuffling.

FIG. 16 contains a listing of the nucleic acid sequence and amino acid sequence for clone 6109 obtained from the initial shuffling.

FIG. 17 contains a listing of the nucleic acid sequence and amino acid sequence for clone 6111 obtained from the initial shuffling.

FIG. 18 contains a listing of the nucleic acid sequence and amino acid sequence for clone 6201 obtained from a second shuffling.

FIG. 19 contains a listing of the nucleic acid sequence and amino acid sequence for clone 6202 obtained from a second shuffling.

FIG. 20 contains a listing of the nucleic acid sequence and amino acid sequence for clone 6203 obtained from a second shuffling.

FIG. 21 contains a listing of the nucleic acid sequence and amino acid sequence for clone 6204 obtained from a second shuffling.

FIG. 22 contains a listing of the nucleic acid sequence and amino acid sequence for clone 6205 obtained from a second shuffling.

FIG. 23 contains a listing of the nucleic acid sequence and amino acid sequence for clone 6206 obtained from a second shuffling.

FIG. 24 contains a listing of the nucleic acid sequence and amino acid sequence for clone 6207 obtained from a second shuffling.

FIG. 25 contains a listing of the nucleic acid sequence and amino acid sequence for clone 6208 obtained from a second shuffling.

FIG. 26 contains a listing of the nucleic acid sequence and amino acid sequence for clone 6209 obtained from a second shuffling.

FIG. 27 contains a listing of the nucleic acid sequence and amino acid sequence for clone 6210 obtained from a second shuffling.

FIG. 28 contains a listing of the nucleic acid sequence and amino acid sequence for clone 6211 obtained from a second shuffling.

FIG. 29 contains a listing of the nucleic acid sequence and amino acid sequence for clone 6212 obtained from a second shuffling.

FIG. 30 contains a listing of the nucleic acid sequence and amino acid sequence for clone 6213 obtained from a second shuffling.

FIG. 31 contains a listing of the nucleic acid sequence and amino acid sequence for clone 6214 obtained from a second shuffling.

FIG. 32 contains a listing of the nucleic acid sequence and amino acid sequence for clone 6215 obtained from a second shuffling.

FIG. 33 is a nucleic acid sequence alignment of the four parental clones encoding hepatitis surface antigen proteins obtained from HBV (SEQ ID NO:1), woolly monkey hepatitis virus (WMHV; SEQ ID NO:3), human/woodchuck hepatitis virus (HWHV; SEQ ID NO:5), and chimpanzee-gibbon hepatitis virus (CGHV; SEQ ID NO:7), and the indicated clones (6101 (SEQ ID NO:9); 6102 (SEQ ID NO:11); 6103 (SEQ ID NO:13); 6104 (SEQ ID NO:15); 6105 (SEQ ID NO:17); 6106 (SEQ ID NO:19); 6107 (SEQ ID NO:21); 6108 (SEQ ID NO:23); 6109 (SEQ ID NO:25); 6110 (SEQ ID NO:68); 6111 (SEQ ID NO:27); 6201 (SEQ ID NO:29); 6202 (SEQ ID NO:31); 6203 (SEQ ID NO:33); 6204 (SEQ ID NO:35); 6205 (SEQ ID NO:37); 6206 (SEQ ID NO:39); 6207 (SEQ ID NO:41); 6208 (SEQ ID NO:43); 6209 (SEQ ID NO:45); 6210 (SEQ ID NO:47); 6211 (SEQ ID NO:49); 6212 (SEQ ID NO:51); 6213 (SEQ ID NO:53); 6214 (SEQ ID NO:55); and 6215 (SEQ ID NO:57)).

FIG. 34 is an amino acid sequence alignment of the hepatitis surface antigen proteins encoded by the four parental clones from HBV (SEQ ID NO:2), woolly monkey hepatitis virus (WMHV; SEQ ID NO:4), human/woodchuck hepatitis virus (HWHV; SEQ ID NO:6), and chimpanzee-gibbon hepatitis virus (CGHV; SEQ ID NO:8), and the indicated clones (6101 (SEQ ID NO:10); 6102 (SEQ ID NO:12); 6103 (SEQ ID NO:14); 6104 (SEQ ID NO:16); 6105 (SEQ ID NO:18); 6106 (SEQ ID NO:20); 6107 (SEQ ID NO:22); 6108 (SEQ ID NO:24); 6109 (SEQ ID NO:26); 6110 (SEQ ID NO:69); 6111 (SEQ ID NO:28); 6201 (SEQ ID NO:30); 6202 (SEQ ID NO:32); 6203 (SEQ ID NO:34); 6204 (SEQ ID NO:36); 6205 (SEQ ID NO:38); 6206 (SEQ ID NO:40); 6207 (SEQ ID NO:42); 6208 (SEQ ID NO:44); 6209 (SEQ ID NO:46); 6210 (SEQ ID NO:48); 6211 (SEQ ID NO:50); 6212 (SEQ ID NO:52); 6213 (SEQ ID NO:54); 6214 (SEQ ID NO:56); and 6215 (SEQ ID NO:58)).

FIG. 35 contains a wild-type hepatitis B virus sequence with a summary of the differences observed in clones 6101-6109, 6111, and 6201-6215.

FIG. 36 contains a diagram of a vector used to express HBsAg clones.

FIG. 37. Geometric Mean Titers (GMT) of anti-HBsAg obtained with first round clones. Geometric Mean Titers±SEM of anti-HBsAg were measured by ELISA in sera obtained by immunizing test groups of mice each with one of ten improved clones selected as inducing the highest expression levels in the initial screening procedure. The clone names are shown on the X axis. HBV is a plasmid used as a control that wild-type hepatitis B envelope gene-containing plasmid used as a control.

DETAILED DESCRIPTION

Figure 1:
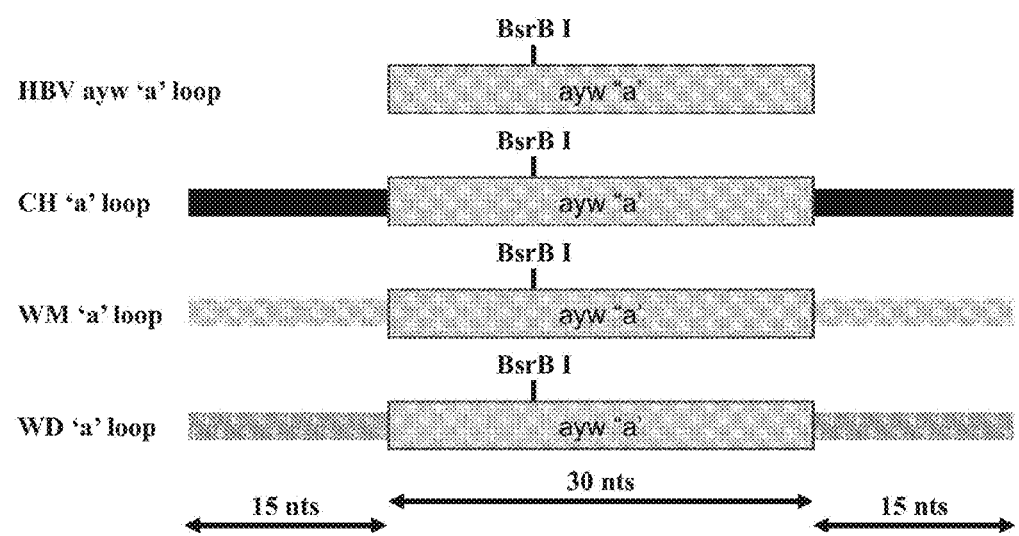
FIG. 1 is a schematic of the strategy used in designing the strain-specific oligonucleotide primers used to keep the 'a' epitope loop constrained during the DNA shuffling reaction. Thirty nucleotides of the HBV (strain ayw) 'a' loop sequence were held constant and flanked by fifteen nucleotides on each side derived from the related HBs genes of chimpanzee/gibbon, woodchuck, and woolly monkey. A restriction endonuclease BsrB I site sequence (CCGCTC) was introduced in the sequence encoding the HBV "a" loop.
Figure 3:
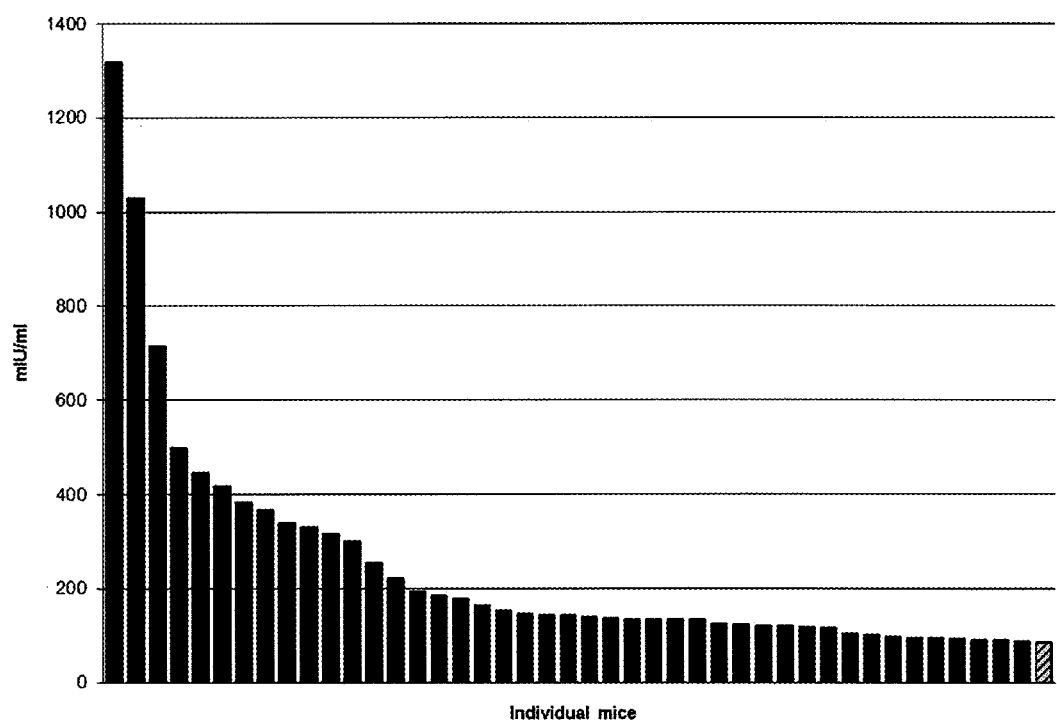
FIG. 3 shows representative ELISA data from primary screening of a first shuffled library are shown. Anti-Hepatitis B antibody levels present in the sera of mice injected with clones from the first shuffled library were measured by ELISA and expressed as milli-International Units per mL. A reference level typically used is the highest antibody level induced in mice by a positive-control DNA vaccine (measured as mIU/mL using a commercial anti-HBsAg detection kit). The striped bar indicates antibody levels induced by a wild-type clone. The black bars indicate antibody levels above reference value induced by shuffled clones.

This document provides methods and materials for producing immune responses against hepatitis B viruses. For example, this document provides polypeptides, nucleic acid molecules encoding such polypeptides, virus-like particles containing such polypeptides, vaccine preparations containing one or more polypeptides provided herein, vaccine preparations containing one or more nucleic acid molecules provided herein, vaccine preparations containing one or more virus-like particles provided herein, and methods for inducing immune responses against hepatitis B viruses within mammals (e.g., humans).

As described herein, a polypeptide provided herein can be designed to include the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). Such polypeptides can be used to induce an immune response against hepatitis B viruses within a mammal. In some cases, a polypeptide provided herein can have the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 and can have the identity to SEQ ID NO:2, 4, 6, and 8 as indicated in Table 1.

TABLE 1

Percentages of amino acid residues of the indicated clones that are identical to those of the indicated parental clones.

| Clone No. | SEQ ID NO:[a] | SEQ ID NO: 2[b] | SEQ ID NO: 4[c] | SEQ ID NO: 6[d] | SEQ ID NO: 8[e] |
|---|---|---|---|---|---|
| 6101 | 10 | 87.6 | 96.9 | 59.7 | 78.5 |
| 6102 | 12 | 95.6 | 88.1 | 60.6 | 82.9 |
| 6103 | 14 | 95.6 | 88.1 | 62.8 | 80.3 |
| 6104 | 16 | 95.1 | 92.0 | 60.2 | 78.5 |
| 6105 | 18 | 96.5 | 88.1 | 60.6 | 82.9 |
| 6106 | 20 | 92.9 | 90.7 | 62.8 | 78.5 |
| 6107 | 22 | 96.9 | 87.6 | 61.5 | 80.3 |
| 6108 | 24 | 88.1 | 84.1 | 65.6 | 79.4 |
| 6109 | 26 | 88.1 | 84.1 | 65.6 | 79.4 |
| 6111 | 28 | 94.7 | 92.5 | 61.9 | 77.6 |
| 6201 | 30 | 93.4 | 91.2 | 60.2 | 79.4 |
| 6202 | 32 | 95.6 | 87.2 | 61.1 | 83.3 |
| 6203 | 34 | 95.1 | 92.0 | 60.2 | 78.5 |
| 6204 | 36 | 95.1 | 92.0 | 60.2 | 78.5 |
| 6205 | 38 | 92.5 | 91.2 | 60.6 | 79.4 |
| 6206 | 40 | 96.0 | 89.4 | 61.5 | 82.0 |
| 6207 | 42 | 92.5 | 90.3 | 62.4 | 78.1 |
| 6208 | 44 | 92.9 | 86.3 | 62.8 | 81.6 |
| 6209 | 46 | 94.2 | 87.6 | 61.1 | 84.2 |
| 6210 | 48 | 95.1 | 92.5 | 61.1 | 78.5 |
| 6211 | 50 | 92.5 | 91.2 | 60.6 | 79.4 |
| 6212 | 52 | 92.0 | 91.6 | 60.2 | 78.9 |
| 6213 | 54 | 91.6 | 91.2 | 61.1 | 82.9 |
| 6214 | 56 | 84.5 | 85.0 | 65.6 | 72.4 |
| 6215 | 58 | 88.9 | 87.6 | 67.0 | 77.6 |

[a]provided SEQ ID NO: is for the amino acid sequence of the indicated clone number.
[b]SEQ ID NO: 2 is the amino acid sequence for the human parental clone.
[c]SEQ ID NO: 4 is the amino acid sequence for the woolly monkey parental clone.
[d]SEQ ID NO: 6 is the amino acid sequence for the human/woodchuck parental clone.
[e]SEQ ID NO: 8 is the amino acid sequence for the chimpanzee/gibbon parental clone.

In some cases, a polypeptide provided herein can be an isolated polypeptide. The term "isolated" as used herein with reference to polypeptides refers to (a) a polypeptide that is not associated with proteins that such polypeptide is normally associated with in nature or (b) a polypeptide that does not occur or exist in nature.

In some cases, a polypeptide provided herein can be a substantially pure polypeptide. The term "substantially pure" as used herein with reference to polypeptides refers to a polypeptide preparation that is substantially free of other polypeptides, lipids, carbohydrates, and nucleic acid. In some cases, a substantially pure polypeptide can be a polypeptide that is at least 60 percent pure or is a chemically synthesized polypeptide. A substantially pure polypeptide can be at least about 60, 65, 70, 75, 80, 85, 90, 95, or 99 percent pure. Typically, a substantially pure polypeptide will yield a single major band on a non-reducing polyacrylamide gel.

In some cases, a polypeptide provided herein can include the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 except that the amino acid sequence includes a variation (e.g., a substitution, addition, or deletion) at one or more positions (e.g., one, two, three, four, five, six, seven, eight, nine, ten, eleven, twelve, 13, 14, 15, 16, 17, 18, 19, 20, or more positions). Such variant sequences, e.g., those having one or more amino acid substitutions relative to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58, can be prepared and modified as described herein. For example, a polypeptide provided herein can include the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 except that the amino acid sequence includes a conservative or non-conservative amino acid substitution at one or more positions (e.g., one, two, three, four, five, six, seven, eight, nine, ten, eleven, twelve, 13, 14, 15, 16, 17, 18, 19, 20, or more positions). In some cases, an amino acid substitution can be made by selecting substitutions that do not differ significantly in their effect on maintaining (a) the structure of the peptide backbone in the area of the substitution, (b) the charge or hydrophobicity of the molecule at a particular site, or (c) the bulk of the side chain. For example, naturally occurring residues can be divided into groups based on side-chain properties: (1) hydrophobic amino acids (methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Further examples of conservative substitutions that can be made at any position within the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58 include, without limitation, those set forth in Table 2.

TABLE 2

Examples of conservative amino acid substitutions.

| Original Residue | Exemplary substitutions |
|---|---|
| Ala | Val, Leu, Ile |
| Arg | Lys, Gln, Asn |
| Asn | Gln, His, Lys, Arg |
| Asp | Glu |
| Cys | Ser |
| Gln | Asn |
| Glu | Asp |
| Gly | Pro |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala |
| Pro | Gly |
| Ser | Thr |
| Thr | Ser |
| Trp | Tyr |
| Tyr | Trp, Phe, Thr, Ser |
| Val | Ile, Leu, Met, Phe, Ala |

In some case, an amino acid sequence used to make a polypeptide provided herein can include one or more non-conservative substitutions. Non-conservative substitutions typically entail exchanging a member of one of the classes described above for a member of another class.

In some cases, a polypeptide provided herein can have an amino acid sequence with at least 90% (e.g., at least 90%, 91%, 92%, 93%, 94%, 95%, 96%, 97%, 98%, 99%, or 100%) sequence identity to a reference sequence (e.g., SEQ ID NO:10, 12, 14, 16, 18, 20, 22, 24, 26, 28, 30, 32, 34, 36, 38, 40, 42, 44, 46, 48, 50, 52, 54, 56, or 58). Percent sequence identity is calculated by determining the number of matched positions in aligned amino acid sequences (target amino acid sequence aligned to an identified amino acid sequence), dividing the number of matched positions by the number of amino acids of the identified amino acid sequence (e.g., SEQ ID NO:10), and multiplying by 100. A matched position refers to a position in which identical amino acids occur at the same position in aligned amino acid sequences. Percent sequence identity also can be determined for nucleic acid sequences.

Percent sequence identity is determined by comparing a target amino acid sequence to the identified amino acid sequence (e.g., SEQ ID NO:10) using the ClustalW alignment tool provided in the Geneious software platform (version 6.05, Biomatters Ltd, Auckland, New Zealand).

Any appropriate method can be used to obtain a polypeptide provided herein. For example, common polypeptide purification techniques such as affinity chromatography and HPLC as well as polypeptide synthesis techniques can be used. In addition, any appropriate material can be used as a source to obtain a polypeptide provided herein. For example, cultured cells engineered to over-express a particular polypeptide provided herein (e.g., a cell line designed to include a nucleic acid molecule provided herein) can be used to produce a polypeptide provided herein. Such cells can be prokaryotic cells (e.g., bacterial cells such as *E. coli, Bacillus subtilis*, or *Pseudomonas* cells) or eukaryotic cells (e.g., yeast cells such as *Saccharomyces cerevisiae, Hansenula polymorpha* or *Pichia pastoris* cells, insect cells such as *Drosophila melanogaster* (e.g., Schneider 2 or Schneider 3 cells), *Spodoptera frugiperda*, or *Trichoplusia ni* cells, or mammalian cells such as CHO, HEK 293, MRC, or PER-C6 cells). In some cases, a polypeptide provided herein can be designed to contain an amino acid sequence that allows the polypeptide to be captured onto an affinity matrix. For example, a tag such as c-myc, hemagglutinin, polyhistidine, Flag™ tag (Kodak), Strep-Tag, V5, or VSV-G can be used to aid polypeptide purification. Such tags can be inserted anywhere alone a polypeptide including at either the carboxyl or amino termini.

In some cases, a polypeptide provided herein can be a fusion polypeptide. Such a fusion polypeptide can include one or more additional amino acid sequences in addition to the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). The additional amino acid sequences can be the amino acid sequence of a tag as described above, a marker such as GFP or Luciferase, an enzyme such as alkaline phosphatase or GST, or a cytokine such as GM-CSF, IL-2, or IL-12, or a chemokine such as IP-10, MCP-3, or RANTES.

This document also provides nucleic acid molecules that encode a polypeptide provided herein. The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism or virus from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

A nucleic acid molecule provided herein (e.g., an isolated nucleic acid molecule) can encode any of the polypeptides provided herein. For example, a nucleic acid molecule provided herein can encode a polypeptide having the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). Examples of such nucleic acid molecules include, without limitation, nucleic acid molecules that have the nucleic acid sequence set forth in SEQ ID NO:9, 11, 13, 15, 17, 19, 21, 23, 25, 27, 29, 31, 33, 35, 37, 39, 41, 43, 45, 47, 49, 51, 53, 55, or 57. In some cases, nucleic acid molecule provided herein can be codon-optimized to express the encoded polypeptide in cells of a particular species (e.g., codon-optimized for expression in bacterial cells, yeast cells, insect cells, fungal cells, algal cells, mammalian cells, or human cells). For example, a nucleic acid molecule provided herein encoding a polypeptide having the amino acid sequence set forth in SEQ ID NO:10 can include a codon-optimized version of the nucleic acid sequence set for in SEQ ID NO:9.

In some cases, a nucleic acid molecule provided herein can be a vector. A vector can be is a replicon, such as a plasmid, phage, virus, or cosmid, into which another DNA segment may be inserted so as to bring about the replication of the inserted segment. An "expression vector" is a vector that includes one or more expression control sequences. An "expression control sequence" is a sequence (e.g., a DNA sequence) that controls or regulates the transcription and/or translation of another sequence (e.g., another DNA sequence).

In expression vectors, a nucleic acid molecule provided herein (e.g., a nucleic acid encoding a polypeptide provided herein) can be operably linked to one or more expression control sequences. As used herein, "operably linked" means incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 to 500 nucleotides upstream of the point at which transcription starts (generally near the initiation site for RNA polymerase II). To bring a coding sequence under the control of a promoter, the translation initiation site of the translational reading frame of the polypeptide can be positioned between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the polypeptide encoded by the coding sequence.

Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Invitrogen/Life Technologies (Carlsbad, Calif.).

An expression vector can include a tag sequence designed to facilitate subsequent manipulation of the expressed nucleic acid sequence (e.g., purification or localization). Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide including at either the carboxyl or amino terminus.

A nucleic acid molecule provided herein can be obtained using any appropriate method including, without limitation, common molecular cloning and chemical nucleic acid synthesis techniques. For example, PCR can be used to obtain a nucleic acid containing a nucleic acid sequence sharing similarity to a nucleic acid molecule provided herein, and common mutagenesis techniques can be used to introduce desired nucleotide additions, deletions, substitutions, or combinations thereof into the obtained nucleic acid. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

This document also provides virus-like particles that include one or more of the polypeptides provided herein. For example, a virus-like particle provided herein can be designed to include a polypeptide having the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). In some cases, a single virus-like particle can include more than one different polypeptide provided herein. For example, a single virus-like particle provided herein can include both a polypeptide having the amino acid sequence as set forth in SEQ ID NO:16 and a polypeptide having the amino acid sequence as set forth in SEQ ID NO:24. Other combinations of polypeptides that can be used to make virus-like particles having a collection of different polypeptides include, without limitation, those set forth in Table 3.

TABLE 3

Combinations of polypeptides for virus-like particles (VLPs).

| VLP ID No. | Sequence identifiers of polypeptides to be included in the VLP |
|---|---|
| 7101 | 14, 16, 18 |
| 7102 | 22, 24, 28 |
| 7103 | 14, 16, 18, 22, 24 |
| 7104 | 36, 38 |
| 7105 | 32, 52, 58 |
| 7106 | 32, 36, 38, 52, 58 |
| 7107 | 14, 16, 36, 38 |
| 7108 | 22, 24, 28, 32, 52, 58 |
| 7109 | 16, 18, 24, 32, 36, 38, 52, 58 |

Any appropriate method can be used to make virus-like particles provided herein. For example, a virus-like particle provided herein can be made using a method described elsewhere. See, e.g., U.S. Pat. No. 4,803,164, which describes a method to produce HBs-containing VLPs in yeast cells; U.S. Pat. No. 6,551,820, which describes a method to produce HBs-containing VLPs in transgenic plants; and European Patent Application No. EP0241021 A2, which describes a method to produce HBs-containing VLPs in Chinese Hamster Ovary cells or normal liver cells.

This document also provides vaccine preparations for inducing an immune response within a mammal against a hepatitis B virus. In some cases, a vaccine preparation provided herein can include one or more of the polypeptides provided herein. For example, a vaccine preparation provided herein can be designed to include a polypeptide having the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). In some cases, a single vaccine preparation can include more than one different polypeptide provided herein. For example, a single vaccine preparation provided herein can include both a polypeptide having the amino acid sequence as set forth in SEQ ID NO:16 and a polypeptide having the amino acid sequence as set forth in SEQ ID NO:24. Other combinations of polypeptides that can be used to make a vaccine preparation having a collection of different polypeptides include, without limitation, those set forth in Table 4.

TABLE 4

Combinations of polypeptides for vaccine preparations.

| Vaccine ID No. | Sequence identifiers of polypeptides to be included in the vaccine preparation |
|---|---|
| 8101 | 14, 16, 18 |
| 8102 | 22, 24, 28 |
| 8103 | 14, 16, 18, 22, 24 |
| 8104 | 36, 38 |
| 8105 | 32, 52, 58 |
| 8106 | 32, 36, 38, 52, 58 |
| 8107 | 14, 16, 36, 38 |
| 8108 | 22, 24, 28, 32, 52, 58 |
| 8109 | 16, 18, 24, 32, 36, 38, 52, 58 |

In some cases, a vaccine preparation provided herein can include one or more of the nucleic acid molecules provided herein. For example, a vaccine preparation provided herein can be designed to include a nucleic acid vector having a promoter operably linked to a nucleic acid sequence that encodes a polypeptide having the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). In some cases, a single vaccine preparation can include more than one different nucleic acid molecule provided herein. For example, a single vaccine preparation provided herein can include both a nucleic acid vector designed to express a polypeptide having the amino acid sequence as set forth in SEQ ID NO:16 and a nucleic acid vector designed to express a polypeptide having the amino acid sequence as set forth in SEQ ID NO:24. Other combinations of vectors that can be used to make a vaccine preparation having a collection of different vectors include, without limitation, those set forth in Table 5. In some cases, a single nucleic acid vector can encode two or more polypeptides provided herein. For example, a single nucleic acid vector can be designed to encode a combination of polypeptides as set forth in Table 4.

TABLE 5

Combinations of vectors for vaccine preparations.

| Vaccine ID No. | Sequence identifiers of polypeptides to be encoded by individual vectors included in the vaccine preparation |
|---|---|
| 9101 | 14, 16, 18 |
| 9102 | 22, 24, 28 |
| 9103 | 14, 16, 18, 22, 24 |
| 9104 | 36, 38 |
| 9105 | 32, 52, 58 |
| 9106 | 32, 36, 38, 52, 58 |
| 9107 | 14, 16, 36, 38 |
| 9108 | 22, 24, 28, 32, 52, 58 |
| 9109 | 16, 18, 24, 32, 36, 38, 52, 58 |

In some cases, a vaccine preparation provided herein can include one or more of the virus-like particles provided herein. For example, a vaccine preparation provided herein can be designed to include a virus-like particle that includes a polypeptide having the amino acid sequence as set forth in SEQ ID NO:10, 12, 14, 16, 18, 20, 22, 24, 26, 28, 30, 32, 34, 36, 38, 40, 42, 44, 46, 48, 50, 52, 54, 56, or 58 (or an amino acid sequence that is at least about 86, 87, 88, 89, 90, 91, 92, 93, 94, 95, 96, 97, 98, 99, or 100 percent identical to the amino acid sequence set forth in SEQ ID NO:10, 12, 14, 16, 18, 20, 22, 24, 26, 28, 30, 32, 34, 36, 38, 40, 42, 44, 46, 48, 50, 52, 54, 56, or 58). In some cases, a single vaccine preparation can include more than one different virus-like particles provided herein. For example, a single vaccine preparation provided herein can include both a virus-like particle that includes a polypeptide having the amino acid sequence as set forth in SEQ ID NO:16 and a virus-like particle that includes a polypeptide having the amino acid sequence as set forth in SEQ ID NO:24. Other combinations of virus-like particles that can be used to make a vaccine preparation having a collection of different virus-like particles include, without limitation, those set forth in Table 6.

TABLE 6

Combinations of VLPs for vaccine preparations.

| Vaccine ID No. | Specific VLPs to be included in the vaccine preparation |
|---|---|
| 10101 | VLP ID#7101, VLP ID#7102 |
| 10102 | VLP ID#7104, VLP ID#7105 |
| 10103 | VLP ID#7101, VLP ID#7104 |
| 10104 | VLP ID#7102, VLP ID#7105 |
| 10105 | VLP ID#7101, VLP ID#7102, VLP ID#7104, VLP ID#7105 |
| 10106 | VLP ID#7103, VLP ID#7106 |
| 10107 | VLP ID#7101, VLP ID#7104, VLP ID#7105 |

Any appropriate method can be used to formulate a vaccine preparation provided herein (e.g., a polypeptide vaccine, nucleic acid vaccine, or VLP vaccine provided herein). For example, a polypeptide vaccine provided herein, a nucleic acid vaccine provided herein, or a VLP vaccine provided herein can be formulated to include one or more adjuvants. An adjuvant can be an immunological compound that can enhance an immune response against a particular antigen such as a polypeptide provided herein. Suitable adjuvants include, without limitation, alum as well as other aluminum-based compounds (e.g., $Al_2O_3$) that can be obtained from various commercial suppliers. For example, REHYDRAGEL® adjuvants can be obtained from Reheis Inc. (Berkeley Heights, N.J.). REHYDRAGEL® adjuvants are based on crystalline aluminum oxyhydroxide, and are hydrated gels containing crystalline particles with a large surface area (about 525 $m^2/g$). Their $Al_2O_3$ content typically ranges from about 2 percent to about 10 percent. Rehydragel LG®, for example, has an $Al_2O_3$ content of about 6 percent, and flows readily upon slight agitation. Rehydragel LG® also has a protein binding capacity of 1.58 (i.e., 1.58 mg of bovine serum albumin bound per 1 mg of $Al_2O_3$), a sodium content of 0.02 percent, a chloride content of 0.28 percent, undetectable sulphate, an arsenic level less than 3 ppm, a heavy metal content less than 15 ppm, a pH of 6.5, and a viscosity of 1090 cp. Rehydragel LG® can be combined with a polypeptide solution (e.g., a polypeptide in PBS) to yield $Al(OH)_3$. In some cases, ALHYDROGEL™, an aluminum hydroxy gel adjuvant (Alhydrogel™ 1.3%, Alhydrogel™ 2.0%, or Alhydrogel™ "85") obtained from Brenntag Stinnes Logistics, can be used.

In some cases, Montanide ISA 51 can be included in a vaccine preparation provided herein. MN51 (MONTANIDE® Incomplete SEPPIC Adjuvant (ISA) 51) as well as MN720 are available from Seppic (Paris, France). MN51 contains mannide oleate (MONTANIDE® 80, also known as anhydro mannitol octadecenoate) in mineral oil solution (Drakeol®6 VR). MONTANIDE® 80 is a limpid liquid with a maximum acid value of 1, a saponification value of 164-172, a hydroxyl value of 89-100, an iodine value of 67-75, a maximum peroxide value of 2, a heavy metal value less than 20 ppm, a maximum water content of 0.35%, a maximum color value of 9, and a viscosity at 25° C. of about 300 mPas. MONTANIDE® associated with oil (e.g., mineral oil, vegetable oil, squalane, squalene, or esters) is known as MONTANIDE® ISA. Drakeol® 6 VR is a pharmaceutical grade mineral oil. Drakeol® 6 VR contains no unsaturated or aromatic hydrocarbons, and has an A.P.I. gravity of 36.2-36.8, a specific gravity at 25° C. of 0.834-0.838, a viscosity at 100° F. of 59-61 SSU or 10.0-10.6 centistokes, a refractive index at 25° C. of 1.458-1.463, a better than minimum acid test, is negative for fluorescence at 360 nm, is negative for visible suspended matter, has an ASTM pour test value of 0-15° F., has a minimum ASTM flash point of 295° F., and complies with all RN requirements for light mineral oil and ultraviolet absorption. MN51 contains about 8 to 12 percent anhydro mannitol octadecenoate and about 88 to 92 percent mineral oil.

Other immunostimulatory components that can be used include, without limitation, plant extracts derived from the Soap bark tree (Quillaja species) containing members of a family of plant-based compounds called saponins.

Other adjuvants that can be included in a vaccine preparation provided herein include, without limitation, immunostimulating complexes (ISCOMs) that can contain such components as cholesterol and saponins. Examples include, without limitation, ISCOMATRIX™ and MATRIX-M™. ISCOM matrices can be prepared and conjugated to $Cu^{2+}$. Adjuvants such as FCA, FIA, MN51, MN720, and $Al(OH)_3$ are commercially available from companies such as Seppic, Difco Laboratories (Detroit, Mich.), and Superfos Biosector A/S (Vedbeak, Demark).

Other immunostimulatory components include, without limitation, muramyldipeptide (e.g., N-acetylmuramyl-L-alanyl-D-isoglutamine; MDP), monophosphoryl-lipid A (MPL), formyl-methionine containing tripeptides such as N-formyl-Met-Leu-Phe, or a bacterial lipopolysaccharide. Such compounds are commercially available from Sigma Chemical Co. (St. Louis, Mo.) and RIBI ImmunoChem Research, Inc. (Hamilton, Mont.), for example. In some cases, an adjuvant can be Complete Freund's Adjuvant or Incomplete Freund's Adjuvant.

In some cases, a nucleic acid vaccine preparation provided herein can be formulated to lack an adjuvant. For example, a nucleic acid vaccine preparation provided herein can be designed to include a nucleic acid molecule that encodes a polypeptide provided herein without including any adjuvant.

In some cases, a polypeptide vaccine provided herein, a nucleic acid vaccine provided herein, or a VLP vaccine provided herein can be formulated to include other components such as cytokines, chemokines, monoclonal antibodies, or co-stimulatory molecules such as B7.

This document also provides methods for preparing a vaccine preparation provided herein. Such methods can involve suspending an amount of a polypeptide provided herein, a VLP provided herein, or a nucleic acid vector provided herein in a suitable amount of a physiological buffer (e.g., PBS). The polypeptides, VLPs, or nucleic acid vectors then can optionally be combined with a suitable amount of an adjuvant/immunostimulatory compound. The combining step can be achieved by any appropriate method, including, for example, stirring, shaking, vortexing, or passing back and forth through a needle attached to a syringe.

A vaccine preparation provided herein can be prepared in batch, such that enough unit doses are obtained for multiple injections (e.g., injections into multiple mammals or multiple injections into the same mammal). A "unit dose" of a vaccine preparation provided herein refers to the amount of a vaccine preparation administered to a mammal at one time. A unit dose of a vaccine preparation provided herein can contain an amount of polypeptides, VLPs, or nucleic acid molecules effective to induce an immune response against a hepatitis B virus. For example, a unit dose of a vaccine preparation provided herein can contain between about 0.1 µg and about 1 g (e.g., 1 µg, 10 µg, 15 µg, 25 µg, 30 µg, 50 µg, 100 µg, 250 µg, 280 µg, 300 µg, 500 µg, 750 µg, 1 mg, 10 mg, 15 mg, 25 mg, 30 mg, 50 mg, 100 mg, 250 mg, 280 mg, 300 mg, 500 mg, 750 mg, or more) of polypeptides, VLPs, or nucleic acid molecules. In the case of vaccine preparations containing viral vectors, a unit dose of a vaccine preparation can have a titer between about $10^3$ to $10^{10}$ (e.g. $10^3$, $10^3$, $10^4$, $10^5$, $10^6$, $10^7$, $10^8$, $10^9$, or $10^{10}$) viral particles or plaque forming units.

This document also provides methods for inducing an immune response within a mammal (e.g., a human) against a hepatitis B virus. For example, one or more polypeptide vaccines provided herein, one or more nucleic acid vaccines provided herein, one or more VLP vaccine provided herein, or combinations thereof can be administered to a mammal (e.g., a human) to induce an immune response against hepatitis B viruses. In some cases, an immune response against hepatitis B viruses can be induced by administering one or more nucleic acid vaccines provided herein followed by a vaccine that includes a hepatitis B virus antigen or followed by one or more polypeptide vaccines provided herein. For example, Vaccine ID No. 9101 can be administered to a human, and 1 to 30 days later, Vaccine ID No. 8105 can be administered to that human. In some cases, Vaccine ID No. 9101 can be administered followed 20 to 60 days later by Vaccine ID No. 7101. In some cases, Vaccine ID No. 9109 can be administered followed 30 to 120 days later by Vaccine ID No. 7106.

In some cases, a vaccine preparation provided herein can be delivered as a prophylactic vaccine to increase a mammal's resistance to a hepatitis B virus infection. For example, one or more polypeptide vaccines provided herein, one or more nucleic acid vaccines provided herein, one or more VLP vaccine provided herein, or combinations thereof can be administered to a human who has not been infected with a hepatitis B virus.

In some cases, a vaccine preparation provided herein can be used to treat a mammal after the mammal is infected with hepatitis B virus (e.g., an acutely hepatitis B virus infected or chronically hepatitis B virus infected mammal). For example, one or more polypeptide vaccines provided herein, one or more nucleic acid vaccines provided herein, one or more VLP vaccine provided herein, or combinations thereof can be administered to a human acutely or chronically infected with hepatitis B virus. Administration of a vaccine preparation provided herein to a mammal infected with hepatitis B virus can result in a reduction in hepatitis B viral load, a reduction in the severity of the symptoms of the hepatitis B virus infection, a reduction in the degree of liver cirrhosis, a reduction in the incidence of hepatocellular cancer, or a clearance of the hepatitis B virus from the liver.

This document also provides methods for priming a mammal (e.g., a human) to receive a vaccine containing a hepatitis B virus antigen. For example, one or more polypeptide vaccines provided herein, one or more nucleic acid vaccines provided herein, one or more viral vaccines provided herein, one or more VLP vaccine provided herein, or combinations thereof can be administered to a mammal (e.g., a human) to prime that mammal for generating an enhanced immune response against hepatitis B viruses. Once primed, the mammal can be treated with a vaccine containing a hepatitis B virus antigen (e.g., Engerix) or a vaccine preparation provided herein.

A vaccine preparation provided herein can be administered using any appropriate method. For example, the administration can be, for example, topical (e.g., transdermal or intranasal), pulmonary (e.g., by inhalation or insufflation of powders or aerosols), oral, or parenteral (e.g., by intradermal, subcutaneous, intramuscular, or intraperitoneal injection, or by intravenous drip). Administration can be rapid (e.g., by injection) or can occur over a period of time (e.g., by slow infusion or administration of slow release formulations). In some cases, a nucleic acid vaccine can be delivered intramuscularly followed 1-90 days (e.g., between 1 and 90, between 1 and 80, between 1 and 70, between 1 and 60, between 1 and 50, between 5 and 90, between 10 and 90, between 20 and 90, between 5 and 75, between 10 and 75, between 10 and 50, between 20 and 50, between 25 and 50, or between 30 and 60 days) later by a VLP vaccine containing adjuvant.

The invention will be further described in the following examples, which do not limit the scope of the invention described in the claims.

EXAMPLES

Example 1

Producing Shuffled Hepatitis B Surface Antigen

The parental DNA sequences encoding the preS2 and S regions of the hepatitis envelope protein were derived from the human, chimpanzee, gibbon, woolly monkey, and woodchuck hepadnaviruses and were obtained as follows.

The preS2+S envelope sequence of the human HBV corresponding to that of the ayw subtype (GenBank® Accession No. J02203; GI No. 329640) was amplified by PCR from a plasmid vector called pCAG-M-Kan. The nucleic acid sequence for this obtained DNA is set forth in SEQ ID NO:1 and encodes a hepatitis B surface antigen polypeptide having the amino acid sequence set forth in SEQ ID NO:2.

The woolly monkey envelope (preS2+S) sequence (GenBank® Accession No. AF046996; GI No. 3150070) was synthesized by oligonucleotide gene assembly (Stemmer et al., Gene, 164(1):49-53 (1995)). The nucleic acid sequence for this obtained DNA is set forth in SEQ ID NO:3 and encodes a hepatitis B surface antigen polypeptide having the amino acid sequence set forth in SEQ ID NO:4.

A hybrid envelope gene was designed by combining the preS2 sequence of the human HBV (adw2 subtype; GenBank® Accession No. X02763; GI No. 59418) and the S sequence of the woodchuck hepatitis virus (strain WHV8; GenBank® Accession No. J04514; GI No. 336146). The gene was synthesized by oligonucleotide gene assembly. The nucleic acid sequence for this obtained DNA is set forth in SEQ ID NO:5 and encodes a hepatitis B surface antigen polypeptide having the amino acid sequence set forth in SEQ ID NO:6.

The amino acid sequence differences between the gibbon (GenBank® Accession No. U46935; GI No. 1814218) and the chimpanzee hepatitis (GenBank® Accession No.

D00220; GI No. 163838595) preS2+S envelope proteins were minimal. A single composite parent gene was therefore synthesized by oligonucleotide gene assembly that contained the sum of all the amino acid changes in the chimpanzee and gibbon sequences relative to the corresponding human sequence. During the course of the synthesis of this composite chimp-gibbon sequence, a mutation occurred which led to the introduction of isoleucine at amino acid number 197 in place of the methionine found in the wild-type chimpanzee and gibbon sequences. The nucleic acid sequence for this obtained DNA is set forth in SEQ ID NO:7 and encodes a hepatitis B surface antigen polypeptide having the amino acid sequence set forth in SEQ ID NO:8.

Figure 36:
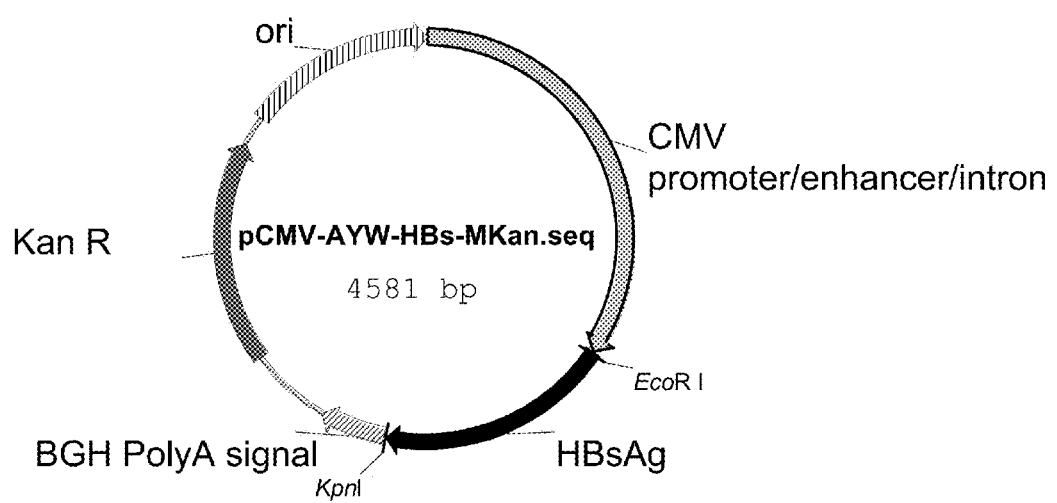
Figure 37:
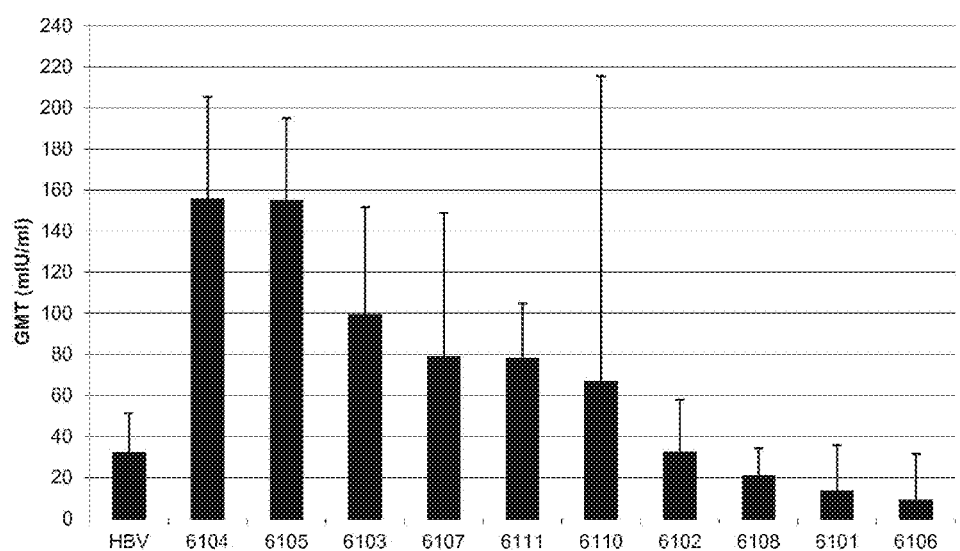
Figure 38:
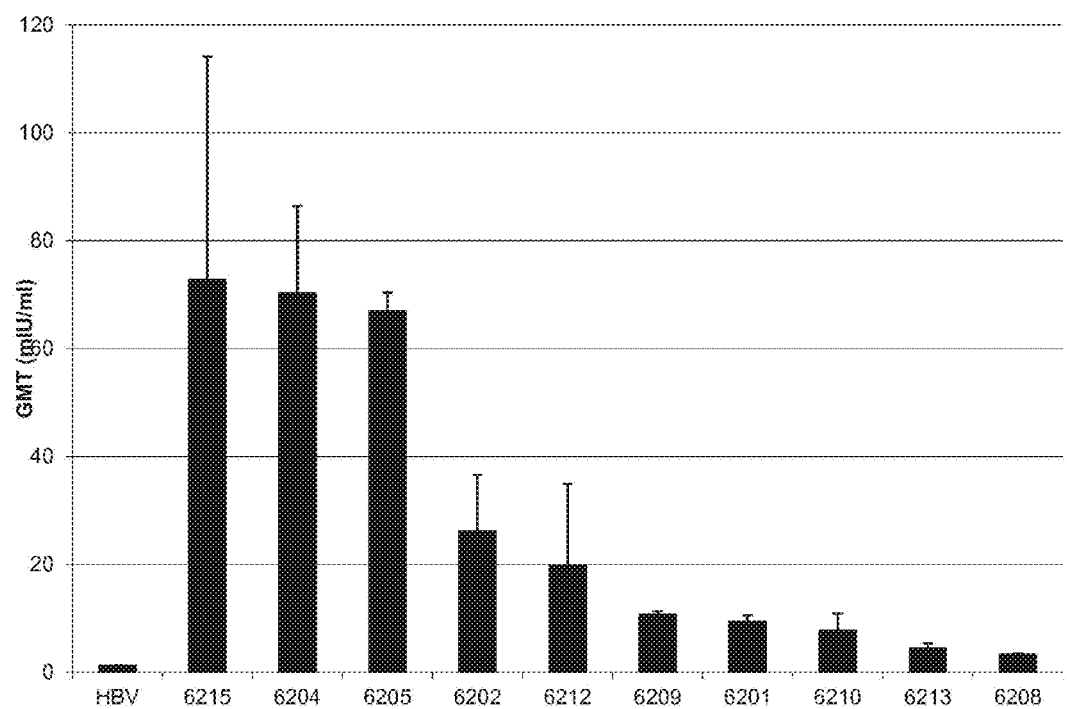
FIG. 38. Geometric Mean Titers of anti-HBsAg obtained with second round clones. A second round library was obtained by shuffling the ten improved clones selected from the first round library. One of ten second round library clones selected based on their induction of anti-HBsAg levels, or the wild-type human hepatitis B envelope gene (HBV), was used to immunize each group of mice. Geometric Mean Titers of anti-HBsAg in the sera from the immunized mice were measured by ELISA. The clone names are shown on the X axis; each bar represents one group of mice. The Y-axis shows the geometric mean titer±SEM of anti-HBsAg for each group in International units.
Figure 39:
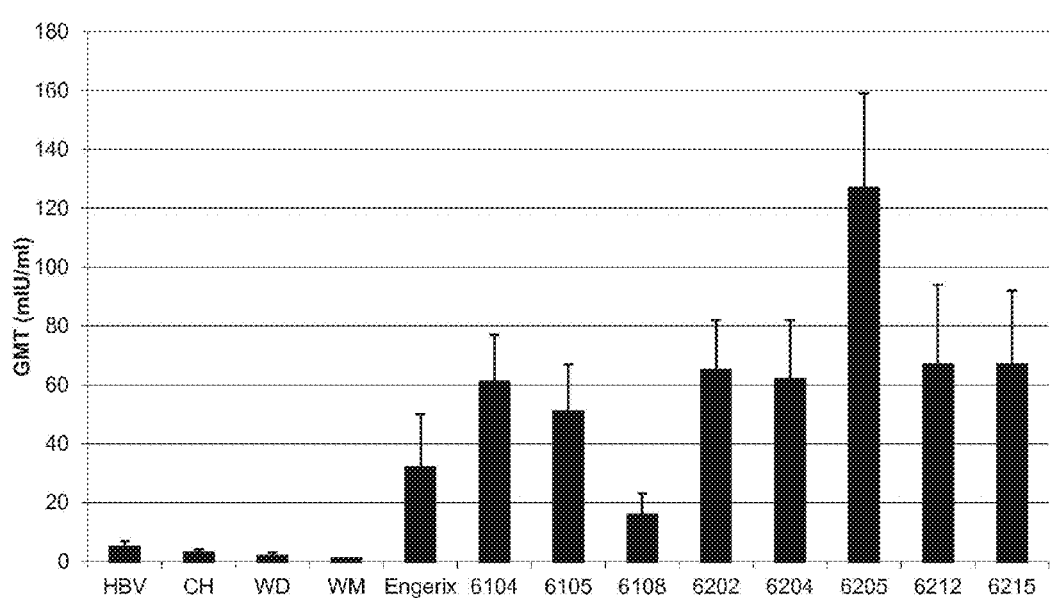
FIG. 39 is a bar graph plotting the GMT (mIU/mL) for the indicated clones when administered to 30 six-week old C57BL/6 mice.
Figure 40:
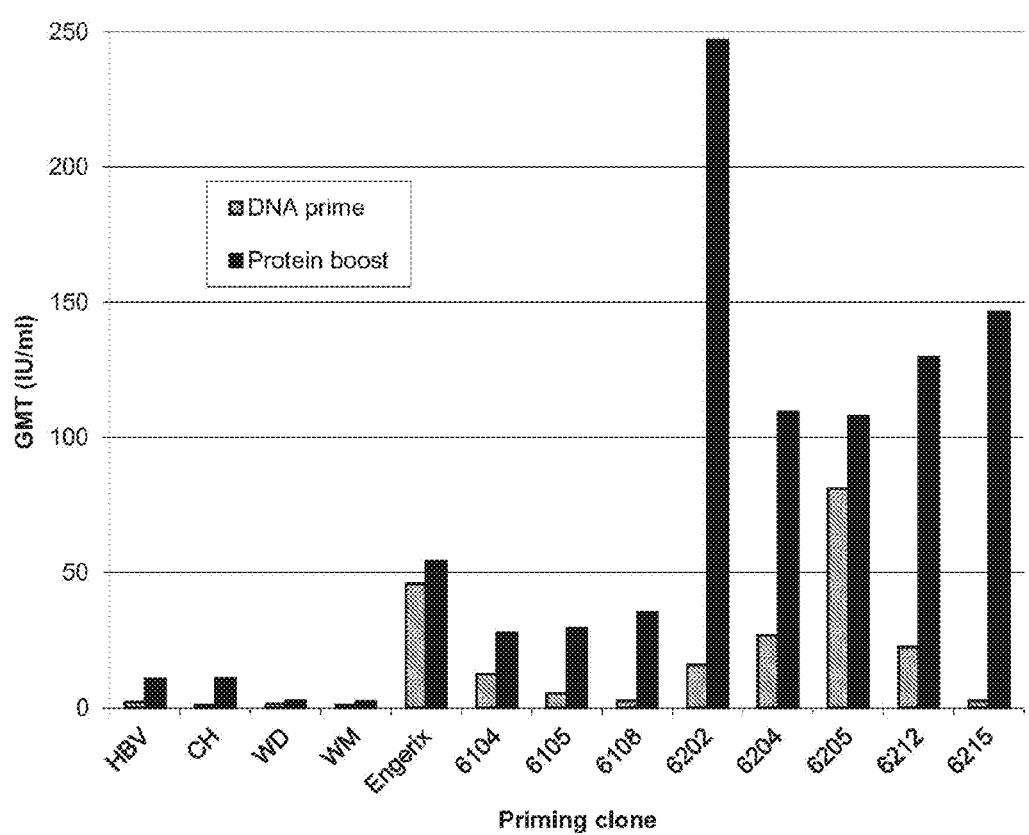
FIG. 40 is a bar graph plotting the GMT (mIU/mL) for the indicated clones when administered to mice alone (DNA prime; gray) or when administered to mice prior to the mice receiving a boost with wild-type protein (Protein Boost; black). The bars labeled "Engerix" are from groups of mice that received one protein injection (gray bar) or the initial priming protein injection followed by the boosting injection (black bar).
Figure 41:
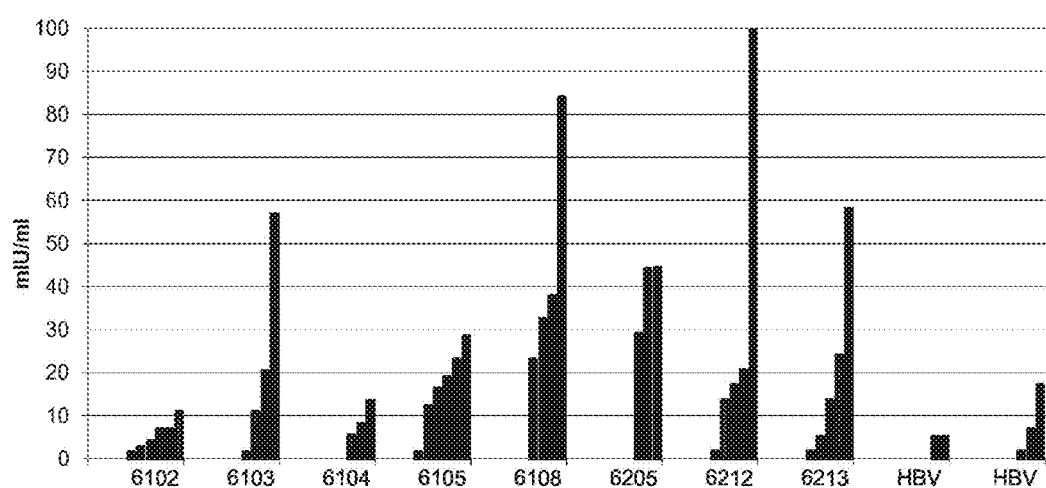
FIG. 41 is a bar graph plotting the GMT (mIU/mL) for the indicated clones when administered to outbred mice.

The workflow for the hepatitis B surface antigen (HBsAg) library was as follows. The original library was generated using DNAse treatment of the four parental sequences described above (SEQ ID NOs:1, 3, 5, and 7). The shuffling of four parental sequences was achieved by assembling DNase I-digested gene fragments. Basically, each parental gene fragment was made from plasmids in PCR reactions using recombinant *Thermus thermophilus* with two vector primers (Pre-for-1 (+):GCA GCT CCT TGC TCC TAA CAG (SEQ ID NO:64); and Pre-rev-2(+):GTA TCA CGA GGC CCT TTC GTC (SEQ ID NO:65)). The PCR was performed at 30 cycles of 1 minute at 95° C., 1 minute at 60° C. and 2 minutes at 72° C. The amplified products were purified in gel electrophoresis and digested by DNase I into fragments ranging from 25 bp to 100 bp, which were further purified in gel. These fragments and the three "a"-epitope constrained primers were mixed and assembled with Taq/Pfu (9:1) polymerase in two rounds of 25 cycle PCR reactions (30 seconds at 96° C., 30 seconds at 40° C. and 30 seconds at 72° C.). In the assembly reactions, the percentage of "a" sequence incorporation was controlled by adjusting the ratio of the constrained "a" oligos to DNase I-digested gene fragments based on their molecular weights (FIG. 1). Assembled HBs recombinants were rescued in 30 cycles of PCR by Taq polymerase (Qiagen) with two nested primers (V1521+: GCT GAC AGA CTA ACA GAC TG (SEQ ID NO:66); and V2453 (+): AAC AGA TGG CTG GCA ACT AG (SEQ ID NO:67); 30 seconds at 95° C., 30 seconds at 55° C., and 1 minute at 72° C.). Subsequently, the shuffled HBs fragments were digested with EcoR I/Asp718, purified in gel, and cloned into EcoR I/Asp718-cut pMKan vector using a standard cloning procedure.

The HBs "a" loop is a major neutralizing epitope and induces protective neutralizing antibodies against hepatitis B virus infection. To preserve this sequence, "a" epitope-constrained libraries were generated. In the assembly reactions, the individual "a" epitope-constrained primer was mixed with the DNase I-digested parental HBs fragments at three concentrations, 0.5:1, 1:1, and 2:1. The incorporation of 'a' epitope primers in shuffling reactions were identified by BsrB I restriction enzyme digestion of the assembled HBs fragments. The rate was further evaluated with BsrB I-digested plasmid DNA samples. The ratio of 0.5:1 exhibited about 30% incorporation, and both 1:1 and 2:1 ratios exhibited 60-65% incorporation. Sequencing analyses of plasmid clones indicated that the three constrained 'a' epitopes were equally incorporated.

'a' Loop-Constrained Primers

The thirty nucleotides of the human 'a' loop 1 sequence were held constant and flanked by fifteen nucleotides on each side derived from the related HBs genes of Chimpanzee/Gibbon (chibbon), Woolly Monkey (WM), or Woodchuck (WD) (FIG. 2). The primers were designed for human HBs 'a' constrained epitopes in the chimpanzee/gibbon hybrid (SEQ ID NO:7), Woolly monkey (SEQ ID NO:3), and human/woodchuck hybrid (SEQ ID NO:5).

Screening

Clones from the library were screened for protein expression using an immunofluorescence assay (IFA) for expression. Briefly, DNA prepared by BioRobot 9600 was transfected to Cos-7 cells (ATCC #CRL-1651) using SuperFect™ transfection reagent in 96-well format as described by the manufacturer (Qiagen). At 48-hour post-transfection, the cells were fixed with paraformaldehyde and stained with goat anti-HBs antibody (Dako #B0560), and then FITC-conjugated rabbit anti-goat immunoglobulins (Dako #P0449). The FITC-positive cells were visualized under fluorescent microscopy. Clones that produced positive IFA signals were then screened in mice by direct intramuscular injection of the plasmid DNA, injecting one shuffled clone in a single mouse. Antibody responses were measured using validated clinical kits (either the Monolisa anti-HBs 3.0 ELISA from Sanofi Diagnostics or the AUSAB EIA ELISA from Abbott Laboratories) and by standard ELISA assays using commercial preparations of the HBsAg obtained from (Seradyn recombinant HBsAg #ABH0705) or the wild-type ayw or adw2 preS2 peptides (custom synthesized by Seradyn) (FIG. 3).

The most immunogenic clones were further analyzed in larger groups of mice (FIG. 37). Briefly, purified DNA (Aldevron LLC, Fargo, N. Dak.) was diluted to a final concentration of 100 μg/mL in sterile PBS. For each test group, 10 six-week old C57BL/6 mice were injected intramuscularly with 50 μL DNA solution in the tibialis anterior muscle of each leg muscle (10 μg DNA total per mouse). Sera were analyzed 4 weeks after treatment for the level of anti-HBsAg as measured by the Sanofi Monolisa anti-HBS kit (expressed above as the GMT±SEM for each group in mIU per mL). Titers were calculated for mice that received clones 6101, 6102, 6103, 6104, 6105, 6106, 6107, 6108, 6109, or 6111, or the wild-type human hepatitis B envelope gene (HBV). Mice injected with clones 6103, 6104, 6105, 6107, or 6111 from the first round library developed titers that were significantly higher than those in mice that were injected with the wild-type hepatitis B envelope gene containing plasmid control (HBV) (FIG. 37).

Based on these results, ten clones were selected (clones 6101, 6102, 6103, 6104, 6105, 6106, 6107, 6108, 6109, and 6111) and then shuffled to generate a second round library. This library was screened as before (IFA and mouse immunization), and immunogenic clones were selected and analyzed further in larger groups of animals (FIG. 39). Briefly, purified DNA (Aldevron LLC, Fargo, N. Dak.) was diluted to a final concentration of 100 μg/mL in sterile PBS. For each test group, 10 six-week old C57BL/6 mice were anesthetized and injected intramuscularly with 50 μL DNA solution in the tibialis anterior muscle of each leg muscle (10 μg DNA total per mouse). Sera was analyzed 4 weeks after treatment for the level of anti-hepatitis B antibody as measured by the Sanofi Monolisa anti-HBS kit (expressed above as the GMT±SEM for each group in International Units). Titers were calculated for mice that received clones 6201, 6202, 6204, 6205, 6208, 6209, 6210, 6212, 6213, or 6215, or the wild-type human hepatitis B envelope gene (HBV). Mice injected with clones 6201, 6202, 6204, 6205, 6208, 6209, 6210, 6212, 6213, or 6215 developed titers that were significantly higher than those in mice that were injected with the wild-type hepatitis B envelope gene containing plasmid control (HBV) (FIG. 38).

The nucleic acid and amino acid sequences of the original four parents (FIGS. 4-7), the ten clones selected from the first round of shuffling (FIGS. 8-17), and the fifteen clones selected from the second round of shuffling (FIGS. 18-32) are presented in FIGS. 4-32. An alignment of the parental and shuffled DNA and protein sequences were obtained using the Clustal W algorithm within the AlignX component of Vector NTI ver 6.0 and are shown in FIGS. 33 and 34, respectively. A summary of the amino acid changes for the clones shown in FIGS. 8-32 is shown in FIG. 35, along with an indication of the various regions of the protein. The nucleotide sequence and component locations of the vector used in this work are shown in FIG. 36.

Figure 42:
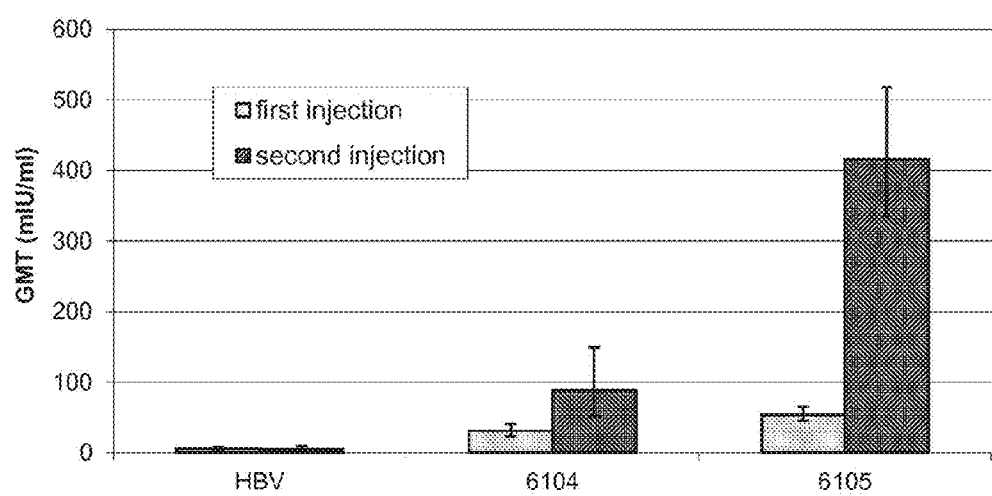
FIG. 42 is a bar graph plotting the GMT (mIU/mL) for the indicated clones when administered to non-responder mice.

All but two of the clones (clones 6101 and 6111) were obtained from a shuffled library in which the main antigenic determinant (the so-called "a-loop") of the human HBV envelope protein was held constant during the shuffling reaction. This was accomplished by including specific oligonucleotides in the shuffling reaction to generate clones in which this sequence was held constant. Several obtained clones did not retain this conserved a-loop in its entirety due to a spontaneous mutation not found in any of the parents used in the shuffling reaction (proline at amino acid number 183 in the place of alanine in the wild-type sequence).

To obtain additional reliable data, an experiment was conducted in which three first round clones (6104, 6105, and 6108) and five second round clones (6202, 6204, 6205, 6212, and 6215) were used to immunize groups of 30 mice per clone. In this experiment, four plasmids were used that express each of the parental envelope sequences used in the initial shuffling reaction (designated HBV, WM, CH, and WD in FIG. 39). Briefly, purified DNA (Aldevron LLC, Fargo, N. Dak.) was diluted to a final concentration of 100 μg/mL in sterile PBS. For each test group, 30 six-week old C57BL/6 mice were anesthetized and injected intramuscularly with 50 μL DNA solution in the tibialis anterior muscle of each leg muscle (10 μg DNA total per mouse). Sera were analyzed four weeks after treatment for the level of anti-hepatitis B antibody as measured by the Abbott AUSZYME ELISA (expressed above as the GMT±SEM for each group in International Units). Titers were calculated for mice that Received DNA clones from the first round library (6104, 6105, and 6108), the second round library (6202, 6204, 6205, 6212, and 6215), and the parents from the original shuffling reaction (wild-type human hepatitis B envelope gene (HBV), woolly monkey hepatitis envelope gene (WM), chimpanzee/gibbon hepatitis envelope gene (CH), and woodchuck hepatitis envelope (WD)). Another group of mice were injected with 1 μg of the commercially available hepatitis B recombinant protein vaccine (Engerix-B, SmithKline Beecham), which was derived from a wild-type HBV gene sequence.

Mice injected with clones 6104, 6105, 6108, 6202, 6204, 6205, 6212, and 6215 developed titers that were significantly higher than mice that were injected with the original parental clones including the wild-type Hepatitis B envelope gene containing plasmid control (HBV) (FIG. 39). The commercial protein vaccine containing purified protein from the wild-type human Hepatitis B envelope gene adjuvanted with aluminum elicited a superior titer compared to DNA injection of the gene by itself (compare "Engerix" to "HBV"). The titer obtained with the commercial vaccine (Engerix) was surpassed by clones 6104, 6105, 6202, 6204, 6205, 6212, and 6215.

Clones 6104, 6105, 6108, 6202, 6204, 6205, 6212, and 6215 were further analyzed for their ability to prime the immune system to respond to wild-type hepatitis B surface antigen. Briefly, purified DNA (Aldevron LLC, Fargo, N. Dak.) was diluted to a final concentration of 100 μg/mL in sterile PBS. For each test group, 20 six-week old C57BL/6 mice were anesthetized and injected intramuscularly with 50 μL DNA solution in the tibialis anterior muscle of each leg muscle (10 μg DNA total per mouse). Three weeks after the initial DNA immunization, 10 mice in each group were injected intraperitoneally with 1 μg of the commercially available hepatitis B recombinant protein vaccine (Engerix-B, SmithKline Beecham) diluted four fold in endotoxin free PBS (5 μg/mL final). Two weeks after the protein injection sera from all mice was analyzed for the level of anti-hepatitis B antibody as measured by the Abbott AUSZYME ELISA (expressed above as the GMT for each group in International Units). Titers were calculated for mice that received DNA clones 6104, 6105, 6108, 6202, 6204, 6205, 6212, or 6215, one of the four parental clones, or the backbone DNA plasmid containing an irrelevant gene sequence.

Clones 6202, 6204, 6205, 6212, and 6215 were superior to the wild-type hepatitis B envelope protein gene for priming the immune system to respond to the hepatitis B protein (FIG. 40). This improved priming was exemplified by the significantly larger memory responses observed after the protein injection in mice that received the shuffled clones as compared to mice that received the wild-type clone (compare black bars of 6104, 6105, 6108, 6202, 6204, 6205, 6212, and 6215 with black bar of HBV in FIG. 40). The relative titers between groups that only received the DNA prime (grey bars) were very similar to the relationships seen in previous experiments (see FIG. 37), but the post boost titers did not maintain this relationship. This change of profile indicated that the high memory response was not solely due to a simple boosting of the higher titer produced by primary injection but rather may indicate that there are aspects of the shuffled genes that enable them to enhance the immune system's ability to respond to a second exposure (compare grey and black bars of 6202 to those of 6205).

In another experiment, clones 6102, 6103, 6104, 6105, 6108, 6205, 6212, and 6213 were tested in a population of outbred mice. Briefly, purified DNA (Aldevron LLC, Fargo, N. Dak.) was diluted to a final concentration of 1000 μg/mL in sterile PBS. For each test group, 10 six-week old outbred Swiss Webster mice were anesthetized and injected intramuscularly with 50 μL DNA solution in the tibialis anterior muscle of each leg muscle (100 μg DNA total per mouse). Sera were analyzed four weeks after treatment for the level of anti-hepatitis B antibody as measured by Abbott AUSZYME ELISA. Titers were calculated for groups of ten mice each that received clones 6102, 6103, 6104, 6105, 6108, 6205, 6212, or 6213, or for two groups of ten mice each that received the wild-type human hepatitis B envelope gene (HBV). Groups of mice injected with clones 6103, 6105, 6108, 6205, 6212, and 6213 exhibited a higher percentage of seroconverting mice and/or higher anti-HBsAg titers than groups of mice that were injected with the wild-type hepatitis B envelope gene containing plasmid control (HBV) (FIG. 41). This population of outbred mice more accurately reflects the heterogeneity seen in natural populations. The ability of shuffled clones to outperform the wild-type clone in this environment suggests that the shuffled clones may outperform the wild-type sequences in other outbred populations such as the human population.

In another experiment, clones 6104 and 6105 were tested in a population of non-responder mice. Briefly, purified DNA (Aldevron LLC, Fargo, N. Dak.) was diluted to a final concentration of 1000 μg/mL in sterile PBS. For each test group, 10 six-week old B10M mice were anesthetized and injected intramuscularly with 50 μL DNA solution in the tibialis anterior muscle of each leg muscle (100 μg DNA total per mouse). Sera were collected by retro-orbital methods four weeks after treatment, and the mice were then given a second dose of DNA. Three weeks after the second treatment, sera was collected. The level of anti-hepatitis B antibody as measured by the Abbott AUSZYME ELISA (expressed as the GMT±SEM for each group in International Units) was determined for both the sera after a single treatment (grey bars in FIG. 42) and the sera after two doses (black bars in FIG. 42). Titers were calculated for mice that received DNA clones 6104 and 6105 and wild-type human hepatitis B envelope gene (HBV) (FIG. 42).

Shuffled clones 6104 and 6105 were able to stimulate strong immune responses in a mouse strain that typically does not respond to hepatitis B antigens. These results were particularly interesting because the B10.M non-responder strain of mice may be similar to a subset of chronically infected humans who also do not respond to HBsAg. The ability of the shuffled clones to overcome this lack of response demonstrates that the shuffled clones provided herein can be used as a therapeutic against chronic hepatitis B.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid molecule comprising a nucleic acid sequence encoding a polypeptide comprising an amino acid sequence, wherein said amino acid sequence is at least 96 percent identical to the amino acid sequence set forth in SEQ ID NO:32.

2. A nucleic acid molecule comprising a nucleic acid sequence encoding a polypeptide comprising an amino acid sequence, wherein said amino acid sequence is at least 96 percent identical to the amino acid sequence set forth in SEQ ID NO:36.

3. A nucleic acid molecule comprising a nucleic acid sequence encoding a polypeptide comprising an amino acid sequence, wherein said amino acid sequence is at least 93 percent identical to the amino acid sequence set forth in SEQ ID NO:38.

4. A nucleic acid molecule comprising a nucleic acid sequence encoding a polypeptide comprising an amino acid sequence, wherein said amino acid sequence is at least 93 percent identical to the amino acid sequence set forth in SEQ ID NO:52.

5. A nucleic acid molecule comprising a nucleic acid sequence encoding a polypeptide comprising an amino acid sequence, wherein said amino acid sequence is at least 91 percent identical to the amino acid sequence set forth in SEQ ID NO:58.

6. The nucleic acid molecule of claim 1, wherein said amino acid sequence is at least 97 percent identical to the amino acid sequence set forth in SEQ ID NO:32.

7. The nucleic acid molecule of claim 1, wherein said amino acid sequence is at least 98 percent identical to the amino acid sequence set forth in SEQ ID NO:32.

8. The nucleic acid molecule of claim 1, wherein said amino acid sequence is at least 99 percent identical to the amino acid sequence set forth in SEQ ID NO:32.

9. The nucleic acid molecule of claim 2, wherein said amino acid sequence is at least 97 percent identical to the amino acid sequence set forth in SEQ ID NO:36.

10. The nucleic acid molecule of claim 2, wherein said amino acid sequence is at least 98 percent identical to the amino acid sequence set forth in SEQ ID NO:36.

11. The nucleic acid molecule of claim 2, wherein said amino acid sequence is at least 99 percent identical to the amino acid sequence set forth in SEQ ID NO:36.

12. The nucleic acid molecule of claim 3, wherein said amino acid sequence is at least 95 percent identical to the amino acid sequence set forth in SEQ ID NO:38.

13. The nucleic acid molecule of claim 3, wherein said amino acid sequence is at least 97 percent identical to the amino acid sequence set forth in SEQ ID NO:38.

14. The nucleic acid molecule of claim 3, wherein said amino acid sequence is at least 99 percent identical to the amino acid sequence set forth in SEQ ID NO:38.

15. The nucleic acid molecule of claim 4, wherein said amino acid sequence is at least 95 percent identical to the amino acid sequence set forth in SEQ ID NO:52.

16. The nucleic acid molecule of claim 4, wherein said amino acid sequence is at least 97 percent identical to the amino acid sequence set forth in SEQ ID NO:52.

17. The nucleic acid molecule of claim 4, wherein said amino acid sequence is at least 99 percent identical to the amino acid sequence set forth in SEQ ID NO:52.

18. The nucleic acid molecule of claim 5, wherein said amino acid sequence is at least 95 percent identical to the amino acid sequence set forth in SEQ ID NO:58.

19. The nucleic acid molecule of claim 5, wherein said amino acid sequence is at least 97 percent identical to the amino acid sequence set forth in SEQ ID NO:58.

20. The nucleic acid molecule of claim 5, wherein said amino acid sequence is at least 99 percent identical to the amino acid sequence set forth in SEQ ID NO:58.

* * * * *

SEQUENCE LISTING

```
<160> NUMBER OF SEQ ID NOS: 69

<210> SEQ ID NO 1
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 1
atgcagtgga attccacaac cttccaccaa actctgcaag atcccagagt gagaggcctg      60
tatttccctg ctggtggctc cagttcagga acagtaaacc ctgttctgac tactgcctct     120
cccttatcgt caatcttctc gaggattggg gaccctgcgc tgaacatgga gaacatcaca     180
tcaggattcc taggacccct tctcgtgtta caggcggggt ttttcttgtt gacaagaatc     240
ctcacaatac cgcagagtct agactcgtgg tggacttctc tcaattttct aggggggaact    300 accgtgtgtc ttggccaaaa ttcgcagtcc ccaacctcca atcactcacc aacctcttgt     360
cctccaactt gtcctggtta tcgctggatg tgtctgcggc gttttatcat cttcctcttc     420
atcctgctgc tatgcctcat cttcttgttg gttcttctgg actatcaagg tatgttgccc     480
gtttgtcctc taattccagg atcctcaaca accagcacgg gaccatgccg gacctgcatg     540
actactgctc aaggaacctc tatgtatccc tcctgttgct gtaccaaacc ttcggacgga     600
aattgcacct gtattcccat cccatcatcc tgggctttcg gaaaattcct atgggagtgg     660
gcctcagccc gtttctcctg gctcagttta ctagtgccat ttgttcagtg gttcgtaggg     720
ctttccccca ctgtttggct ttcagttata tggatgatgt ggtattgggg gccaagtctg     780
tacagcatct tgagtccctt tttaccgctg ttaccaattt tcttttgtct ttgggtatac     840
atttaa                                                                846

<210> SEQ ID NO 2
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 2

Met Gln Trp Asn Ser Thr Thr Phe His Gln Thr Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Val Leu Thr Thr Ala Ser Pro Leu Ser Ser Ile Phe Ser Arg
         35                  40                  45

Ile Gly Asp Pro Ala Leu Asn Met Glu Asn Ile Thr Ser Gly Phe Leu
```

```
            50                  55                  60
Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
        275                 280

<210> SEQ ID NO 3
<211> LENGTH: 852
<212> TYPE: DNA
<213> ORGANISM: Artificial Sequence
<220> FEATURE:
<223> OTHER INFORMATION: synthetic nucleic acid

<400> SEQUENCE: 3
atgcagtgga attccacttc cttccagagt tatcttcaga atccaaaggt cagaggcctc      60
tactttcctg ctggtggctc aacttcaagc attgtcaacc tgttccgaca cactgcctcc     120
accacatcgt caagcttctc gacgactggg gtccctgtca gcaccatgga catcactca      180 tcaggattcc taggaccccct tctcgcatta caggcggtgt tttcttgtt gacaaaaatc     240 ctcacaatgc acagagtct agactcgttg tggacttctc tcaattttct agggggaaca     300
ccagcgtgtc ctggcctaaa ttcgcagtcc ccaacctcca gtcactcacc aacctgctgt     360
ccaccgactt gtcctgggta tcgctggatg tgtttgcggc gttctatcat cttcctcttc     420
atcctgcttc tatgcctcat cttcttgttg gttcttctgg actaccaagg tatgttgccc     480
gtgtgtcctc ttctaccaac agttacagga acaacaacaa caacgggacc tgcaggacc     540 tgcacgccaa ttgttccagg catctcttcg tatccctcat gttgctgtac caaacctacg     600
gacggaaact gcacttgtat tcccatcccc tcatcatggg ctttcgcaaa gttcctatgg     660
gactgggcct tagcccgttt ctcctggctc aattcacttc tgccatttgt tcagtggttc     720
gcagggcttt cccccactgt atggctttta gttatatgga tgatgtggtt ctggggggca     780
```
agtctgttca gcatcttgag tcccttcttg cctctgttac cactttctt ttggctttgg   840 gtatacattt aa   852

<210> SEQ ID NO 4
<211> LENGTH: 283
<212> TYPE: PRT
<213> ORGANISM: Artificial Sequence
<220> FEATURE:
<223> OTHER INFORMATION: synthetic polypeptide

<400> SEQUENCE: 4

Met Gln Trp Asn Ser Thr Ser Phe Gln Ser Tyr Leu Gln Asn Pro Lys
 1               5                  10                  15

Val Arg Gly Leu Tyr Phe Pro Ala Gly Gly Ser Thr Ser Ser Ile Val
            20                  25                  30

Asn Pro Val Pro Thr Thr Ala Ser Thr Thr Ser Ser Ser Phe Ser Thr
        35                  40                  45

Thr Gly Val Pro Val Ser Thr Met Asp Ile Thr Ser Ser Gly Phe Leu
    50                  55                  60

Gly Pro Leu Leu Ala Leu Gln Ala Val Phe Phe Leu Leu Thr Lys Ile
65                  70                  75                  80

Leu Thr Met Pro Gln Ser Leu Asp Ser Leu Trp Thr Ser Leu Asn Phe
                85                  90                  95

Leu Gly Gly Thr Pro Ala Cys Pro Gly Leu Asn Ser Gln Ser Pro Thr
            100                 105                 110

Ser Ser His Ser Pro Thr Cys Cys Pro Pro Thr Cys Pro Gly Tyr Arg
        115                 120                 125

Trp Met Cys Leu Arg Arg Ser Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Leu Pro Thr Val Thr Gly Thr Thr Thr Thr Thr Gly
                165                 170                 175

Pro Cys Arg Thr Cys Thr Pro Ile Val Pro Gly Ile Ser Ser Tyr Pro
            180                 185                 190

Ser Cys Cys Cys Thr Lys Pro Thr Asp Gly Asn Cys Thr Cys Ile Pro
        195                 200                 205

Ile Pro Ser Ser Trp Ala Phe Ala Lys Phe Leu Trp Asp Trp Ala Leu
    210                 215                 220

Ala Arg Phe Ser Trp Leu Asn Ser Leu Leu Pro Phe Val Gln Trp Phe
225                 230                 235                 240

Ala Gly Leu Ser Pro Thr Val Trp Leu Leu Val Ile Trp Met Met Trp
                245                 250                 255

Phe Trp Gly Pro Ser Leu Phe Ser Ile Leu Ser Pro Phe Leu Pro Leu
            260                 265                 270

Leu Pro Leu Phe Phe Trp Leu Trp Val Tyr Ile
        275                 280

<210> SEQ ID NO 5
<211> LENGTH: 834
<212> TYPE: DNA
<213> ORGANISM: Artificial Sequence
<220> FEATURE:
<223> OTHER INFORMATION: synthetic nucleic acid

<400> SEQUENCE: 5

```
atgcagtgga attccactgc cttccaccaa actctgcagg atcccagagt cagggctctg      60
tatcttcctg ctggtggctc cagttcagga acagtaaacc ctgctccgaa tattgcctct     120
cacatctcgt caatctccgc gaggactggg accctgtga cgaacatgtc accatcaagt      180
ctcctaggac tcctcgcagg attacaggtg gtgtatttct tgtggacaaa aatcctaaca     240
atagctcaga atctagattg gtggtggact tctctcagtt ttccaggggg cataccagag     300
tgcactggcc aaaattcgca gttccaaact tgcaaacact tgccaacctc ctgtccacca     360
acttgcaatg gctttcgttg gatgtatctg cggcgtttta tcatatacct attagtcctg     420
ctgctgtgcc tcatcttctt gttggttctc ctggactgga aaggtttaat acctgtctgt     480
cctcttcaac ccacaacaga aacaacagtc aattgcagac aatgcacaat ctctgcacaa     540
gacatgtata ctcctcctta ctgttgttgt taaaaccta cggcaggaaa ttgcacttgt      600
tggcccatcc cttcatcatg ggctttagga aattaccttat gggagtgggc cttagcccgt    660
ttctcttggc tcaatttact agtgcccttg cttcaatggt taggaggaat ttccctcatt     720
gcgtggtttt tgcttatatg gatgatttgg ttttgggggc ccgcacttct gagcatctta     780
ccgccattta ttcccatatt tgttctgttt ttcttgattt gggtatacat ttaa           834
```

<210> SEQ ID NO 6  
<211> LENGTH: 277  
<212> TYPE: PRT  
<213> ORGANISM: Artificial Sequence  
<220> FEATURE:  
<223> OTHER INFORMATION: synthetic polypeptide

<400> SEQUENCE: 6

```
Met Gln Trp Asn Ser Thr Ala Phe His Gln Thr Leu Gln Asp Pro Arg
  1               5                  10                  15

Val Arg Gly Leu Tyr Leu Pro Ala Gly Gly Ser Ser Gly Thr Val
             20                  25                  30

Asn Pro Ala Pro Asn Ile Ala Ser His Ile Ser Ser Ile Ser Ala Arg
         35                  40                  45

Thr Gly Asp Pro Val Thr Asn Met Ser Pro Ser Ser Leu Leu Gly Leu
     50                  55                  60

Leu Ala Gly Leu Gln Val Val Tyr Phe Leu Trp Thr Lys Ile Leu Thr
 65                  70                  75                  80

Ile Ala Gln Asn Leu Asp Trp Trp Trp Thr Ser Leu Ser Phe Pro Gly
                 85                  90                  95

Gly Ile Pro Glu Cys Thr Gly Gln Asn Ser Gln Phe Gln Thr Cys Lys
            100                 105                 110

His Leu Pro Thr Ser Cys Pro Pro Thr Cys Asn Gly Phe Arg Trp Met
        115                 120                 125

Tyr Leu Arg Arg Phe Ile Ile Tyr Leu Leu Val Leu Leu Cys Leu
    130                 135                 140

Ile Phe Leu Leu Val Leu Leu Asp Trp Lys Gly Leu Ile Pro Val Cys
145                 150                 155                 160

Pro Leu Gln Pro Thr Thr Glu Thr Thr Val Asn Cys Arg Gln Cys Thr
                165                 170                 175

Ile Ser Ala Gln Asp Met Tyr Thr Pro Pro Tyr Cys Cys Cys Leu Lys
            180                 185                 190

Pro Thr Ala Gly Asn Cys Thr Cys Trp Pro Ile Pro Ser Ser Trp Ala
        195                 200                 205

Leu Gly Asn Tyr Leu Trp Glu Trp Ala Leu Ala Arg Phe Ser Trp Leu
    210                 215                 220
```

-continued

```
Asn Leu Leu Val Pro Leu Leu Gln Trp Leu Gly Gly Ile Ser Leu Ile
225                 230                 235                 240

Ala Trp Phe Leu Leu Ile Trp Met Ile Trp Phe Trp Gly Pro Ala Leu
                245                 250                 255

Leu Ser Ile Leu Pro Pro Phe Ile Pro Ile Phe Val Leu Phe Phe Leu
                260                 265                 270

Ile Trp Val Tyr Ile
        275

<210> SEQ ID NO 7
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 7
atgcagtgga attctacagt attccaccaa gctctgcaag atcccagagt acggggccta      60
tactttcctg ttggtggctc cagttcagga acattgaacc ctgttccgaa tactgcctct     120
cacatctcgt cagtcttctc gacgactggg accctgcac cgaacatgga gaacatcaca      180
tcaggattcc taggacccct gctcgtgtta caggcgggt ttttcttgtt gacaaaaatc      240
ctcacaatac acagagtct agactcgtgg tggacttctc tcaattttct aggggagca       300 cccgtgtgtc ctggccaaaa ttcgcagtcc ccaacctcca atcactcacc aacctcttgt     360
cctccaattt gtcctggcta tcgctggatg tgtctgcggc gttttatcat cttcctcttc     420
atcctgctgc tatgcctcat cttcttgttg gttcttctgg actatcaagg tatgttgccc     480
gtttgtcctc tacttccagg atcatcgacc accagcacgg gaccatgcaa aacctgcacg     540
atccctgctc aaggaacctc tttgattccc tcatgttgtt gtacaaaacc ttcggacgga     600
aattgcactt gtattcccat cccatcgtct gggctttcg caaaattcct atgggagtgg      660
gcctcagtcc gtttctcctg gctcagttta ctagctccat tgttcagtg gttcgcaggg     720 ctttcccca ctgcttggct tttagctata tggatcatct ggtattgggg gccaaatctg      780
tacaacatct tgaatccatt tataccgctg ttaccaattt tctttgtct ttgggtatac     840 atttaa                                                              846

<210> SEQ ID NO 8
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 8

Met Gln Trp Asn Ser Thr Val Phe His Gln Ala Leu Gln Asp Pro Arg
1               5                   10                  15

Val Arg Gly Leu Tyr Phe Pro Val Gly Gly Ser Ser Gly Thr Leu
            20                  25                  30

Asn Pro Val Pro Asn Thr Ala Ser His Ile Ser Ser Val Phe Ser Thr
        35                  40                  45

Thr Gly Asp Pro Ala Pro Asn Met Glu Asn Ile Thr Ser Gly Phe Leu
    50                  55                  60

Gly Pro Leu Leu Val Leu Gln Ala Gly Phe Phe Leu Leu Thr Lys Ile
65                  70                  75                  80

Leu Thr Ile Pro Gln Ser Leu Asp Ser Trp Trp Thr Ser Leu Asn Phe
```

```
                85                  90                  95
Leu Gly Gly Ala Pro Val Cys Pro Gly Gln Asn Ser Gln Ser Pro Thr
                100                 105                 110

Ser Asn His Ser Pro Thr Ser Cys Pro Pro Ile Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Gln Gly Met Leu Pro
145                 150                 155                 160

Val Cys Pro Leu Leu Pro Gly Ser Ser Thr Thr Ser Thr Gly Pro Cys
                165                 170                 175

Lys Thr Cys Thr Ile Pro Ala Gln Gly Thr Ser Leu Ile Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Ala Lys Phe Leu Trp Glu Trp Ala Ser Val Arg
        210                 215                 220

Phe Ser Trp Leu Ser Leu Leu Ala Pro Phe Val Gln Trp Phe Ala Gly
225                 230                 235                 240

Leu Ser Pro Thr Ala Trp Leu Leu Ala Ile Trp Ile Ile Trp Tyr Trp
                245                 250                 255

Gly Pro Asn Leu Tyr Asn Ile Leu Asn Pro Phe Ile Pro Leu Leu Pro
                260                 265                 270

Ile Phe Phe Cys Leu Trp Val Tyr Ile
            275                 280

<210> SEQ ID NO 9
<211> LENGTH: 864
<212> TYPE: DNA
<213> ORGANISM: Artificial Sequence
<220> FEATURE:
<223> OTHER INFORMATION: synthetic nucleic acid

<400> SEQUENCE: 9
atgcagtgga attctacagt attccaccaa actctgcaag atcccagagt gggggggtctg      60 tatcttcctg ctggtggctc cagttcagga acagtaaacc ctgttctgac tactgcctct     120
cccttatcgt caatcttctc gaggattggg accctgcgc tgaacatgga gaacatcaca      180
tcaggattcc taggacccct ctcgtgttta caggcggggt ttttcttgat gacaaaaatc     240
ctcacaatgc cgcagagtct agactcgtgg tggacttctc tcaattttct agggagagca     300
cccgtgtgtc ctggccaaaa ttcgcagtcc ccaacctcca atcactcacc aacctcttgt     360
cctccaattt gtcctggcta tcgctggatg tgtctgcggc gttttatcat cttcctcttc     420
atcctgctgc tatgcctcat cttcttgttg gttcttctgg actatcgagg tatgttgccc     480
gtttgtcctc tacttccagg atcatcgacc accagcacgg gaccatgcaa aacctgcacg     540
atccctgctc aaggaacctc tttgattccc tcatgttgtt gtacaaaacc ttcgacggaa     600
aattgcactt gtattcccat cccatcgtct gggctttcg caaaattcct atgggagtgg      660
gcctcagtcc gttctcctg ctcagtttta ctagctccat tgttcagcg gttcgcaggg       720 ctttcccca ctgcttggct tttagctata tggatcatct ggtattgggg gccaaatctg      780
tacaacatct tgagtccctt cttgccgctg ttaccaattt tcttttgtct ttgggtatac     840
atttaaatgc tagaggtacc ctga                                             864
```

-continued

<210> SEQ ID NO 10
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 10

```
Met Gln Trp Asn Ser Thr Val Phe His Gln Thr Leu Gln Asp Pro Arg
  1               5                  10                  15

Val Gly Gly Leu Tyr Leu Pro Ala Gly Ser Ser Ser Gly Thr Val
                 20                  25                  30

Asn Pro Val Leu Thr Thr Ala Ser Pro Leu Ser Ser Ile Phe Ser Arg
             35                  40                  45

Ile Gly Asp Pro Ala Leu Asn Met Glu Asn Ile Thr Ser Gly Phe Leu
 50                  55                  60

Gly Pro Leu Leu Val Leu Gln Ala Gly Phe Phe Leu Met Thr Lys Ile
 65                  70                  75                  80

Leu Thr Met Pro Gln Ser Leu Asp Ser Trp Trp Thr Ser Leu Asn Phe
                 85                  90                  95

Leu Gly Arg Ala Pro Val Cys Pro Gly Gln Asn Ser Gln Ser Pro Thr
            100                 105                 110

Ser Asn His Ser Pro Thr Ser Cys Pro Pro Ile Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Lys Thr Cys Thr Ile Pro Ala Gln Gly Thr Ser Leu Ile Pro Ser Cys
            180                 185                 190

Cys Cys Thr Lys Pro Ser Asp Gly Asn Cys Thr Cys Ile Pro Ile Pro
            195                 200                 205

Ser Ser Trp Ala Phe Ala Lys Phe Leu Trp Glu Trp Ala Ser Val Arg
        210                 215                 220

Phe Ser Trp Leu Ser Leu Leu Ala Pro Phe Val Gln Arg Phe Ala Gly
225                 230                 235                 240

Leu Ser Pro Thr Ala Trp Leu Leu Ala Ile Trp Ile Ile Trp Tyr Trp
                245                 250                 255

Gly Pro Asn Leu Tyr Asn Ile Leu Ser Pro Phe Leu Pro Leu Leu Pro
            260                 265                 270

Ile Phe Phe Cys Leu Trp Val Tyr Ile
        275                 280
```

<210> SEQ ID NO 11
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 11

```
atgcagtgga attccacaac cttccaccaa actctgcagg atcccagagt cagggggtctg      60 tatcttcctg ctggtggctc cagttcagga acagtaaacc ctgctccgaa tactgcctct     120
cacatctcgt cagtctttctc gacgactggg gaccctgcac cgaacatgga gaacatcaca     180
```

```
tcaggattcc taggacccct gctcgtgtta caggcggggt ttttcttgtt gacaaaaatc    240
ctcacaatgc cacagagtct agactcgttg tggacttctc tcaattttct aggggggaaca   300 ccagcgtgtc ttggccaaaa ttcgcagtcc ccaacctcca atcactcacc aacctcttgt    360
cctccaactt gtcctggtta tcgctggatg tgtctgcggc gttttatcat cttcctcttc    420
atcctgctgc tatgcctcat cttcttgttg gttcttctgg actatcgagg tatgttgccc    480
gtttgtcctc taattccagg atcctcaaca accagcacgg gaccttgcag acctgtatg     540 actaccgctc aaggaacctc tatgtatccc tcatgttgtt gtacaaaacc ttcggacgga    600
aattgcacct gtattccat cccatcatcc tgggctttcg gaaaattcct atgggactgg     660
gcctcagccc gtttctcctg gctcagttta ctagtgccat tgttcagcg gttcgcaggg     720 ctttctccca ctgcttggct ttcagttata tggatgatgt ggtattgggg accaagtctg    780
tacagcatct tgagtccctt tttaccgctg ttaccaattt tcttttgtct ttgggtatac    840
atttaa                                                                846
```

```
<210> SEQ ID NO 12
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 12

Met Gln Trp Asn Ser Thr Thr Phe His Gln Thr Leu Gln Asp Pro Arg
 1               5                  10                  15

Val Arg Gly Leu Tyr Leu Pro Ala Gly Gly Ser Ser Gly Thr Val
            20                  25                  30

Asn Pro Ala Pro Asn Thr Ala Ser His Ile Ser Ser Val Phe Ser Thr
        35                  40                  45

Thr Gly Asp Pro Ala Pro Asn Met Glu Asn Ile Thr Ser Gly Phe Leu
    50                  55                  60

Gly Pro Leu Leu Val Leu Gln Ala Gly Phe Phe Leu Leu Thr Lys Ile
65                  70                  75                  80

Leu Thr Met Pro Gln Ser Leu Asp Ser Leu Trp Thr Ser Leu Asn Phe
                85                  90                  95

Leu Gly Gly Thr Pro Ala Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Asp Trp Ala Ser Ala Arg
    210                 215                 220

Phe Ser Trp Leu Ser Leu Leu Val Pro Phe Val Gln Arg Phe Ala Gly
225                 230                 235                 240
```

```
Leu Ser Pro Thr Ala Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
        275                 280

<210> SEQ ID NO 13
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 13
atgcagtgga attccactgc cttccaccaa actctgcagg atcccagagt cagggggtctg      60 tatctccctg ctggtggctc cagttcagga acagtaaacc ctgctccgaa tattgcctct     120
cacatctcgt caatctccgc gaggactggg gaccctgcac cgaacatgga gaacatcaca     180
tcaggattcc taggacccct gctcgtgtta caggcggtgt ttttcttgtt gacaagaatc     240
ctcacaatac cgcagagtct agactcgtgg tggacttctc tcaatttttct agggggaact     300 accgtgtgtc ctggccaaaa ttcgcagtcc ccaacctcca atcactcacc aacctcttgt     360
cctccaactt gtcctggtta cgctggatg tgtctgcggc gttttatcat atacctatta     420
gtcctgctgc tgtgcctcat cttcttgttg gttcttctgg actatcaagg tatgttgccc     480
gtttgtcctc taattccagg atcctcaaca accagcacgg gaccatgcaa aacctgtatg     540
actaccgctc aaggaacctc tatgtatccc tcatgttgtt gtacaaaacc ttcggacgga     600
aattgcactt gtattcccat cccatcatcc tgggctttcg gaaaattcct atgggagtgg     660
gcctcagccc gtttctcctg gctcagttta ctagtgccat tgttcagcg gttcgcaggg     720 ctttcccccca ctgtttggct ttcagttata tggatgattt ggttttgggg gccaagtctg     780
tacagcatct tgagtccctt tttaccgctg ttaccaattt tcttttgtct ttgggtatac     840
atttaa                                                               846

<210> SEQ ID NO 14
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 14

Met Gln Trp Asn Ser Thr Ala Phe His Gln Thr Leu Gln Asp Pro Arg
 1               5                  10                  15

Val Arg Gly Leu Tyr Leu Pro Ala Gly Gly Ser Ser Gly Thr Val
             20                  25                  30

Asn Pro Ala Pro Asn Ile Ala Ser His Ile Ser Ser Ile Ser Ala Arg
            35                  40                  45

Thr Gly Asp Pro Ala Pro Asn Met Glu Asn Ile Thr Ser Gly Phe Leu
        50                  55                  60

Gly Pro Leu Leu Val Leu Gln Ala Val Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Thr Val Cys Pro Gly Gln Asn Ser Gln Ser Pro Thr
            100                 105                 110
```

Ser Asn His Ser Pro Thr Ser Cys Pro Pro Thr Cys Pro Gly Tyr Arg
            115                 120                 125

Trp Met Cys Leu Arg Arg Phe Ile Ile Tyr Leu Leu Val Leu Leu Leu
        130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
            195                 200                 205

Ser Ser Trp Ala Phe Gly Lys Phe Leu Trp Glu Trp Ala Ser Ala Arg
        210                 215                 220

Phe Ser Trp Leu Ser Leu Leu Val Pro Phe Val Gln Arg Phe Ala Gly
225                 230                 235                 240

Leu Ser Pro Thr Val Trp Leu Ser Val Ile Trp Met Ile Trp Phe Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
            275                 280

<210> SEQ ID NO 15
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 15
atgcagtgga attctacaac cttccaccaa actctgcagg atcccagagt caggggtctg      60
tatcttcctg ctggtggctc cagttcagga acagtaaacc ctgctccgaa tattgcctct     120
cacatctcgt caatctccgc gaggactggg gaccctgcgc tgaacatgga gaacatcaca     180
tcaggattcc taggacccct ctcgtgttac aggcggggt ttttcttgtt gacaagaatc      240
ctcacaatac acagagtct agactcgtgg tggacttctc tcaattttct aggggaact      300 accgtgtgtc ttggcctaaa ttcgcagtcc ccaacctcca atcactcacc aacctcttgt     360
cctccaactt gtcctggtta tcgctggatg tgtctgcggc gttttatcat cttcctcttc     420
atcctgcttc tatgcctcat cttcttgttg gttcttctgg actatcaagg tatgttgccc     480
gtttgtcccc taattccagg atcctcaaca accagcacgg gaccatgcaa acctgtatg      540 actacccctc aaggaaccctc tatgtatccc tcatgttgct gtaccaaacc ttcggacgga     600
aattgcacct gtattcccat cccatcatcc tgggctttcg gaaaattcct atggagtgg     660 gcctcagccc gtttctcctg ctcagtttta ctagtgccat tgttcagtg gttcgtaggg     720 cttteccccca ctgcttggct tttggctata tggatcatct ggtattggg gccaaatctg      780 tacaacatct tgaatccctt tttaccgctg ttaccaattt tcttttgtct ttgggtatac     840
atttaa                                                                846

<210> SEQ ID NO 16
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 16

```
Met Gln Trp Asn Ser Thr Thr Phe His Gln Thr Leu Gln Asp Pro Arg
 1               5                  10                  15
Val Arg Gly Leu Tyr Leu Pro Ala Gly Ser Ser Gly Thr Val
            20                  25                  30
Asn Pro Ala Pro Asn Ile Ala Ser His Ile Ser Ser Ile Ser Ala Arg
            35                  40                  45
Thr Gly Asp Pro Ala Leu Asn Met Glu Asn Ile Thr Ser Gly Phe Leu
        50                  55                  60
Gly Pro Leu Leu Val Leu Gln Ala Gly Phe Phe Leu Leu Thr Arg Ile
65                  70                  75                  80
Leu Thr Ile Pro Gln Ser Leu Asp Ser Trp Trp Thr Ser Leu Asn Phe
                85                  90                  95
Leu Gly Gly Thr Thr Val Cys Leu Gly Leu Asn Ser Gln Ser Pro Thr
            100                 105                 110
Ser Asn His Ser Pro Thr Ser Cys Pro Pro Thr Cys Pro Gly Tyr Arg
        115                 120                 125
Trp Met Cys Leu Arg Arg Phe Ile Ile Phe Leu Phe Ile Leu Leu Leu
    130                 135                 140
Cys Leu Ile Phe Leu Leu Val Leu Leu Asp Tyr Gln Gly Met Leu Pro
145                 150                 155                 160
Val Cys Pro Leu Ile Pro Gly Ser Ser Thr Thr Ser Thr Gly Pro Cys
                165                 170                 175
Lys Thr Cys Met Thr Thr Pro Gln Gly Thr Ser Met Tyr Pro Ser Cys
            180                 185                 190
Cys Cys Thr Lys Pro Ser Asp Gly Asn Cys Thr Cys Ile Pro Ile Pro
        195                 200                 205
Ser Ser Trp Ala Phe Gly Lys Phe Leu Trp Glu Trp Ala Ser Ala Arg
    210                 215                 220
Phe Ser Trp Leu Ser Leu Leu Val Pro Phe Val Gln Trp Phe Val Gly
225                 230                 235                 240
Leu Ser Pro Thr Ala Trp Leu Leu Ala Ile Trp Ile Ile Trp Tyr Trp
                245                 250                 255
Gly Pro Asn Leu Tyr Asn Ile Leu Asn Pro Phe Leu Pro Leu Leu Pro
            260                 265                 270
Ile Phe Phe Cys Leu Trp Val Tyr Ile
        275                 280
```

<210> SEQ ID NO 17
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 17

```
atgcagtgga attccactgc cttccaccaa actctgcagg atcccagagt caggggtctg      60
tatcttcctg ctggtggctc cagctcagga acagtaaacc ctgctccgaa tattgcctct     120
cacatctcgt caatctccgc gaggattggg accctgcgc tgaacatgga gaacatcaca      180
tcaggattcc taggaccccc tctcgcatta caggcggtgt tttcttgtt gacaaaaatc      240 ctcacaatgc cacagagtct agactcgtgg tggacttctc tcaattttct aggggggaact    300
```

```
accgtgtgtc ttggccaaaa ttcgcagtcc ccaacctcca atcactcacc aacctcttgt    360
cctccaactt gtcctggtta tcgctggatg tgtctgcggc gttttatcat cttcctcttc    420
atcctgctgc tatgcctcat cttcttgttg gttcttctgg actatcgagg tatgttgccc    480
gtttgtcctc taattccagg atcctcaaca accagcacgg gaccatgcaa aacctgtatg    540
actaccgctc aaggaacctc tatgtatccc tcatgttgtt gtacaaaacc ttcggacgga    600
aattgcacct gtattccat cccatcatcc tgggctttcg caaaattcct atggagtgg     660
gcctcagccc gtttctcctg gctcagttta ctagtgccat tgttcagtg gttcgtaggg     720
ctttcccccca ctgtttggct ttcagttata tggatgatgt ggtattgggg gccaagtctg    780
ttcagcatct tgagtccctt cttgcctctg ttaccaattt tcttttgtct ttgggtatac    840
atttaa                                                                846
```

<210> SEQ ID NO 18
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 18

```
Met Gln Trp Asn Ser Thr Ala Phe His Gln Thr Leu Gln Asp Pro Arg
 1               5                  10                  15

Val Arg Gly Leu Tyr Leu Pro Ala Gly Ser Ser Gly Thr Val
                20                  25                  30

Asn Pro Ala Pro Asn Ile Ala Ser His Ile Ser Ser Ile Ser Ala Arg
                35                  40                  45

Ile Gly Asp Pro Ala Leu Asn Met Glu Asn Ile Thr Ser Gly Phe Leu
         50                  55                  60

Gly Pro Leu Leu Ala Leu Gln Ala Val Phe Phe Leu Leu Thr Lys Ile
 65                  70                  75                  80

Leu Thr Met Pro Gln Ser Leu Asp Ser Trp Trp Thr Ser Leu Asn Phe
                85                  90                  95

Leu Gly Gly Thr Thr Val Cys Leu Gly Gln Asn Ser Gln Ser Pro Thr
               100                 105                 110

Ser Asn His Ser Pro Thr Ser Cys Pro Pro Thr Cys Pro Gly Tyr Arg
           115                 120                 125

Trp Met Cys Leu Arg Arg Phe Ile Ile Phe Leu Phe Ile Leu Leu Leu
       130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Lys Phe Leu Trp Glu Trp Ala Ser Ala Arg
    210                 215                 220

Phe Ser Trp Leu Ser Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Phe Ser Ile Leu Ser Pro Phe Leu Pro Leu Leu Pro
```

```
                260            265             270
Ile Phe Phe Cys Leu Trp Val Tyr Ile
            275             280
```

<210> SEQ ID NO 19
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 19

```
atgcagtgga attccacaac cttccaccaa actctgcaag atcccagagt gagaggcctg      60
tatttccctg ctggtggctc cagttcagga acagtaaacc ctgttctgac tactgcctct     120
cccttatcgt caatcttctc gaggattggg gaccctgcgc tgaacatgga gaacatcaca     180
tcaggattcc taggacccct tctcgtgtta caggcggggt ttttcttgtt gacaagaatc     240
ctcacaatac cgcagagtct agactcgttg tggacttctc tcagttttcc aggggggcata    300
ccagagtgca ctggccaaaa ttcgcagtcc ccaacctcca atcactcacc aacctcttgt     360
cctccaactt gtcctggtta tcgctggatg tgtctgcggc gttttatcat cttcctcttc     420
atcctgctgc tatgcctcat cttcttgttg gttcttctgg actatcgagg tatgttgccc     480
gtttgtcctc tacttccagg atcctcaaca accagcacgg gaccctgcag acctgtatg      540
actaccgctc aaggaacctc tatgtatccc tcatgttgct gtaccaaacc ttcggacgga     600
aattgcacct gtattccatc ccatcatcc tgggctttcg caaaattcct atgggagtgg      660
gcctcagccc gtttctcctg ctcagtttta ctagtgccat tgttcagtg gttcgtaggg     720
ctttccccca ctgtttggct ttcagttata tggatcatct ggtattgggg gccaaatctg     780
tacaacatct tgaatccatt tataccgctg ttaccaattt tcttttgtct ttgggtatac     840
atttaa                                                                846
```

<210> SEQ ID NO 20
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 20

```
Met Gln Trp Asn Ser Thr Thr Phe His Gln Thr Leu Gln Asp Pro Arg
  1               5                  10                  15

Val Arg Gly Leu Tyr Phe Pro Ala Gly Ser Ser Ser Gly Thr Val
                 20                  25                  30

Asn Pro Val Leu Thr Thr Ala Ser Pro Leu Ser Ser Ile Phe Ser Arg
             35                  40                  45

Ile Gly Asp Pro Ala Leu Asn Met Glu Asn Ile Thr Ser Gly Phe Leu
         50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Leu Trp Thr Ser Leu Ser Phe
                 85                  90                  95

Pro Gly Gly Ile Pro Glu Cys Thr Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125
```

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Ser Thr Gly Pro Cys
                165                 170                 175

Arg Thr Cys Met Thr Thr Ala Gln Gly Thr Ser Met Tyr Pro Ser Cys
                180                 185                 190

Cys Cys Thr Lys Pro Ser Asp Gly Asn Cys Thr Cys Ile Pro Ile Pro
                195                 200                 205

Ser Ser Trp Ala Phe Ala Lys Phe Leu Trp Glu Trp Ala Ser Ala Arg
        210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Ile Ile Trp Tyr Trp
                245                 250                 255

Gly Pro Asn Leu Tyr Asn Ile Leu Asn Pro Phe Ile Pro Leu Leu Pro
                260                 265                 270

Ile Phe Phe Cys Leu Trp Val Tyr Ile
                275                 280

<210> SEQ ID NO 21
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 21
atgcagtgga attccactgc cttccaccaa actctgcagg atcccagagt caggggtctg         60
tatcttcctg ctggtggctc cagttcagga acagtaaacc ctgctccgaa tattgcctct        120
cccttatcgt caatcttctc gacgactggg gaccctgcac cgaacatgga gaacatcaca        180
tcaggattcc taggacccct ctcgtgttta caggcggggt ttttcttgtt gacaagaatc        240
ctcacaatac cgcagagtct agactcgtgg tggacttctc tcaattttct aggggagcaa        300
cccgtgtgtc ttggccaaaa tcgcagtcc ccaacctcca atcactcacc aacctcttgt        360
cctccaactt gtcctgggta tcgctggatg cgtctgcggc gttttatcat cttcctcttc        420
atcctgctgc tatgcctcat cttcttgttg gttcttctgg actatcgagg tatgttgccc        480
gtttgtcctc taattccagg atcctcaaca accggcacgg gaccctgcag gacctgtatg        540
actactgctc aaggaacctc tatgtatccc tcatgttgtt gtacaaaacc ttcggacgga        600
aattgcactt gtattcccat cccatcatcc tgggctttcg gaaaattcct atgggagtgg        660
gcctcagccc gtttctcctg gctcagttta ctagtgccat tgttcagtg gttcgtaggg        720 ctttcccccg ctgtatggct ttcagttata tggatgatgt ggtattgggg gccaagtctg        780
tacagcatct tgagtccctt tttaccgctg ttaccaattt tcttttggct ttgggtatac        840
atttaa                                                                  846

<210> SEQ ID NO 22
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 22

```
Met Gln Trp Asn Ser Thr Ala Phe His Gln Thr Leu Gln Asp Pro Arg
 1               5                  10                  15

Val Arg Gly Leu Tyr Leu Pro Ala Gly Ser Ser Gly Thr Val
             20                  25                  30

Asn Pro Ala Pro Asn Ile Ala Ser Pro Leu Ser Ser Ile Phe Ser Thr
             35                  40                  45

Thr Gly Asp Pro Ala Pro Asn Met Glu Asn Ile Thr Ser Gly Phe Leu
 50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Ala Pro Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
            115                 120                 125

Trp Met Arg Leu Arg Arg Phe Ile Ile Phe Leu Phe Ile Leu Leu Leu
    130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Gly Thr Gly Pro Cys
                165                 170                 175

Arg Thr Cys Met Thr Thr Ala Gln Gly Thr Ser Met Tyr Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Ala Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Ile Phe Phe Trp Leu Trp Val Tyr Ile
            275                 280
```

<210> SEQ ID NO 23
<211> LENGTH: 840
<212> TYPE: DNA
<213> ORGANISM: Artificial Sequence
<220> FEATURE:
<223> OTHER INFORMATION: synthetic nucleic acid

<400> SEQUENCE: 23

```
atgcagtgga attctactgc cttccaccaa actctgcagg atcccagagt cagggtctg      60 tatcttcctg ctggtggctc cagttcagga acagtaaacc ctgctccgaa tattgcctct     120
cacatctcgt caatctccgc gaggactggg gaccctgtga cgaacatgtc accatcaagt     180
ctcctaggac tcctcgcagg attacaggtg gtgtatttct gtggacaaa  atcctaaca     240 ataccgcaga gtctagactc gtggtggact ctctcaatt ttctagggg agcacccgtg       300 tgtcctggcc aaaattcgca gtccccaacc tccaatcact caccaacctc ttgtcctcca    360
atttgtcctg gttatcgctg gatgtgtctg cggcgtttta tcatcttcct cttcatcctg    420
```

```
cttctatgcc tcatcttctt gttggttctt ctggactatc aaggtatgtt gcccgtttgt    480
cctctaattc caggatcatc gaccaccagc acgggaccat gcaaaacctg tatgactacc    540
cctcaaggaa cctctatgta tccctcatgt tgttgtacca aaccttcgga cggaaattgc    600
acctgtattc ccatcccatc atcctgggct ttcggaaaat tcctatggga gtgggcctca    660
gtccgtttct cctggctcag tttactagct ccatttgttc agcggttcgt agggctttcc    720
cccactgttt ggctttcagt tatatggatg atgtggttct gggggccaag tctgttcagc    780
atcttgagtc ccttcttgcc tctgttacca cttttctttt ggctttgggt atacatttaa    840
```

<210> SEQ ID NO 24
<211> LENGTH: 279
<212> TYPE: PRT
<213> ORGANISM: Artificial Sequence
<220> FEATURE:
<223> OTHER INFORMATION: synthetic polypeptide

<400> SEQUENCE: 24

```
Met Gln Trp Asn Ser Thr Ala Phe His Gln Thr Leu Gln Asp Pro Arg
 1               5                  10                  15

Val Arg Gly Leu Tyr Leu Pro Ala Gly Gly Ser Ser Ser Gly Thr Val
             20                  25                  30

Asn Pro Ala Pro Asn Ile Ala Ser His Ile Ser Ser Ile Ser Ala Arg
         35                  40                  45

Thr Gly Asp Pro Val Thr Asn Met Ser Pro Ser Ser Leu Leu Gly Leu
     50                  55                  60

Leu Ala Gly Leu Gln Val Val Tyr Phe Leu Trp Thr Lys Ile Leu Thr
 65                  70                  75                  80

Ile Pro Gln Ser Leu Asp Ser Trp Trp Thr Ser Leu Asn Phe Leu Gly
                 85                  90                  95

Gly Ala Pro Val Cys Pro Gly Gln Asn Ser Gln Ser Pro Thr Ser Asn
            100                 105                 110

His Ser Pro Thr Ser Cys Pro Pro Ile Cys Pro Gly Tyr Arg Trp Met
        115                 120                 125

Cys Leu Arg Arg Phe Ile Ile Phe Leu Phe Ile Leu Leu Leu Cys Leu
    130                 135                 140

Ile Phe Leu Leu Val Leu Leu Asp Tyr Gln Gly Met Leu Pro Val Cys
145                 150                 155                 160

Pro Leu Ile Pro Gly Ser Ser Thr Thr Ser Thr Gly Pro Cys Lys Thr
                165                 170                 175

Cys Met Thr Thr Pro Gln Gly Thr Ser Met Tyr Pro Ser Cys Cys Cys
            180                 185                 190

Thr Lys Pro Ser Asp Gly Asn Cys Thr Cys Ile Pro Ile Pro Ser Ser
        195                 200                 205

Trp Ala Phe Gly Lys Phe Leu Trp Glu Trp Ala Ser Val Arg Phe Ser
    210                 215                 220

Trp Leu Ser Leu Leu Ala Pro Phe Val Gln Arg Phe Val Gly Leu Ser
225                 230                 235                 240

Pro Thr Val Trp Leu Ser Val Ile Trp Met Met Trp Phe Trp Gly Pro
                245                 250                 255

Ser Leu Phe Ser Ile Leu Ser Pro Phe Leu Pro Leu Leu Pro Leu Phe
            260                 265                 270

Phe Trp Leu Trp Val Tyr Ile
        275
```

<210> SEQ ID NO 25
<211> LENGTH: 840
<212> TYPE: DNA
<213> ORGANISM: Artificial Sequence
<220> FEATURE:
<223> OTHER INFORMATION: synthetic nucleic acid

<400> SEQUENCE: 25

```
atgcagtgga attctactgc cttccaccaa actctgcagg atcccagagt caggggtctg      60
tatcttcctg ctggtggctc cagttcagga acagtaaacc ctgctccgaa tattgcctct     120
cacatctcgt caatctccgc gaggactggg gaccctgtga cgaacatgtc accatcaagt     180
ctcctaggac tcctcgcagg attacaggtg gtgtatttct tgtggacaaa atcctaaca     240
ataccgcaga gtctagactc gtggtggact ctctcaatt ttctaggggg agcacccgtg      300
tgtcctggcc aaaattcgca gtccccaacc tccaatcact caccaacctc ttgtcctcca     360
atttgtcctg gttatcgctg gatgtgtctg cggcgtttta tcatcttcct cttcatcctg     420
cttctatgcc tcatcttctt gttggttctt ctggactatc aaggtatgtt gcccgtttgt     480
cctctaattc aggatcatc gaccaccagc acgggaccat gcaaaacctg tatgactacc      540
cctcaaggaa cctctatgta tccctcatgt tgttgtacca aaccttcgga cggaaattgc     600
acctgtattc ccatcccatc atcctgggct tcggaaaat tcctatggga gtgggcctca     660
gtccgtttct cctggctcag tttactagct ccatttgttc agcggttcgt agggctttcc     720
cccactgttt ggctttcagt tatatggatg atgtggttct gggggccaag tctgttcagc     780
atcttgagtc ccttcttgcc tctgttacca cttttctttt ggctttgggt atacattaa      840
```

<210> SEQ ID NO 26
<211> LENGTH: 279
<212> TYPE: PRT
<213> ORGANISM: Artificial Sequence
<220> FEATURE:
<223> OTHER INFORMATION: synthetic polypeptide

<400> SEQUENCE: 26

```
Met Gln Trp Asn Ser Thr Ala Phe His Gln Thr Leu Gln Asp Pro Arg
  1               5                  10                  15

Val Arg Gly Leu Tyr Leu Pro Ala Gly Ser Ser Ser Gly Thr Val
                 20                  25                  30

Asn Pro Ala Pro Asn Ile Ala Ser His Ile Ser Ser Ile Ser Ala Arg
             35                  40                  45

Thr Gly Asp Pro Val Thr Asn Met Ser Pro Ser Ser Leu Leu Gly Leu
         50                  55                  60

Leu Ala Gly Leu Gln Val Val Tyr Phe Leu Trp Thr Lys Ile Leu Thr
 65                  70                  75                  80

Ile Pro Gln Ser Leu Asp Ser Trp Trp Thr Ser Leu Asn Phe Leu Gly
                 85                  90                  95

Gly Ala Pro Val Cys Pro Gly Gln Asn Ser Gln Ser Pro Thr Ser Asn
            100                 105                 110

His Ser Pro Thr Ser Cys Pro Pro Ile Cys Pro Gly Tyr Arg Trp Met
        115                 120                 125

Cys Leu Arg Arg Phe Ile Ile Phe Leu Phe Ile Leu Leu Leu Cys Leu
    130                 135                 140

Ile Phe Leu Leu Val Leu Leu Asp Tyr Gln Gly Met Leu Pro Val Cys
145                 150                 155                 160

Pro Leu Ile Pro Gly Ser Ser Thr Thr Ser Thr Gly Pro Cys Lys Thr
                165                 170                 175
```

Cys Met Thr Thr Pro Gln Gly Thr Ser Met Tyr Pro Ser Cys Cys Cys
                180                 185                 190

Thr Lys Pro Ser Asp Gly Asn Cys Thr Cys Ile Pro Ile Pro Ser Ser
            195                 200                 205

Trp Ala Phe Gly Lys Phe Leu Trp Glu Trp Ala Ser Val Arg Phe Ser
        210                 215                 220

Trp Leu Ser Leu Leu Ala Pro Phe Val Gln Arg Phe Val Gly Leu Ser
225                 230                 235                 240

Pro Thr Val Trp Leu Ser Val Ile Trp Met Met Trp Phe Trp Gly Pro
                245                 250                 255

Ser Leu Phe Ser Ile Leu Ser Pro Phe Leu Pro Leu Leu Pro Leu Phe
            260                 265                 270

Phe Trp Leu Trp Val Tyr Ile
        275

<210> SEQ ID NO 27
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 27

| | | | | | | |
|---|---|---|---|---|---|---|
| atgcagtgga | attccactgc | cttccaccaa | actctgcaag | atcccagagt | acggggccta | 60 |
| tactttcctg | ttggtggctc | cagttcagga | acagtaaacc | ctgctccgaa | tattgcctct | 120 |
| cccttatcgt | caatcttctc | gaggattggg | accctgcgc | tgaacatgga | gaacatcaca | 180 |
| tcaggattcc | taggacccct | gctcgtgtta | caggcggggt | ttttcttgtt | gacaaaagtc | 240 |
| ctcacaatac | cgcagagcct | agactcgtgg | tggacttctc | tcaattttct | aggggggaact | 300 |
| accgtgtgtc | ttggccaaaa | ttcgcagtcc | ccaacctcca | atcactcacc | aacctcttgt | 360 |
| cctccaactt | gtcctggtta | tcgctggatg | tgtctgcggc | gttttatcat | cttcctcttc | 420 |
| atcctgctgc | tatgcctcat | cttcttgttg | gttcttctgg | actatcgagg | tatgttgccc | 480 |
| gtttgtcctc | taattccagg | atcctcaaca | accagcacgg | gaccctgcag | gacctgtatg | 540 |
| actaccgctc | aaggaaccct | tatgtatccc | tcatgttgtt | gtacaaaacc | ttcggacgga | 600 |
| aattgcactt | gtattcccat | cccatcatcc | tgggctttcg | gaaaattcct | atgggagtgg | 660 |
| gcctcagccc | gtttctcctg | gctcagttta | ctagtgccat | tgttcagtg | gttcgtaggg | 720 |
| ctttccccca | ctgcttggct | tttagctata | tggatcatct | ggtattgggg | ccaaatctg | 780 |
| tacaacatct | tgaatccatt | tataccgctg | ttaccaattt | tcttttgtct | ttgggtatac | 840 |
| atttaa | | | | | | 846 |

<210> SEQ ID NO 28
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 28

Met Gln Trp Asn Ser Thr Ala Phe His Gln Thr Leu Gln Asp Pro Arg
  1               5                  10                  15

Val Arg Gly Leu Tyr Phe Pro Val Gly Gly Ser Ser Ser Gly Thr Val
                20                  25                  30

Asn Pro Ala Pro Asn Ile Ala Ser Pro Leu Ser Ser Ile Phe Ser Arg

```
                 35                  40                  45
Ile Gly Asp Pro Ala Leu Asn Met Glu Asn Ile Thr Ser Gly Phe Leu
 50                  55                  60

Gly Pro Leu Leu Val Leu Gln Ala Gly Phe Phe Leu Leu Thr Lys Val
 65                  70                  75                  80

Leu Thr Ile Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
                100                 105                 110

Ser Asn His Ser Pro Thr Ser Cys Pro Pro Thr Cys Pro Gly Tyr Arg
                115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
                180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
210                 215                 220

Phe Ser Trp Leu Ser Leu Leu Val Pro Phe Val Gln Trp Phe Val Gly
225                 230                 235                 240

Leu Ser Pro Thr Ala Trp Leu Ala Ile Trp Ile Trp Tyr Trp
                245                 250                 255

Gly Pro Asn Leu Tyr Asn Ile Leu Asn Pro Phe Ile Pro Leu Leu Pro
                260                 265                 270

Ile Phe Phe Cys Leu Trp Val Tyr Ile
        275                 280

<210> SEQ ID NO 29
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 29
atgcagtgga attccactgc cttccaccaa actctgcagg atcccagagt caggggtctg      60
tatcttcctg ctggtggctc cagctcagga acagtaaacc ctgctccgaa tattgcctct     120
cacatctcgt caatcccgc gaggattggg accctgcgc tgaacatggg aacatcaca      180 tcaggattcc taggacccct tctcgtgtta caggcgggt ttttcttgat gacaaaaatc     240
ctcacaatgc cgcagagtct agactcgtgg tggacttctc tcaatttct agggggaact     300 accgtgcgtc ctggccaaaa ttcgcagtcc ccaacctcca atcactcacc aacctcttgt     360
cctccaactt gtcctggtta tcgctggatg tgtctgcggc gttttatcat cttcctcttc     420
atcctgctgc tatgcctcat cttcttgttg gttcttctgg actatcgagg tatgttgccc     480
gtttgtcctc tacttccagg tcctcaaca accagcacgg accctgcag gacctgtatg     540 actaccgctc aaggaacctc tatgtatccc tcatgttgct gtaccaaacc ttcggacgga     600
aattgcacct gtattcccat cccatcatcc tgggctttcg caaaattcct atgggagtgg     660
```

```
gcctcagccc gtttctcctg gctcagttta ctagtgccat ttgttcagtg gttcgtaggg    720 ctttcccca ctgtttggct ttcagttata tggatcatct ggtattgggg gccaaatctg     780
tacaacatct tgaatccatt tataccgctg ttaccaattt tcttttgtct ttgggtatac    840
atttaa                                                                846
```

```
<210> SEQ ID NO 30
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 30
```

Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Ile Gly Asp Pro Ala Leu Asn Met Gly Asn Ile Thr Ser Gly Phe Leu
50                  55                  60

Gly Pro Leu Leu Val Leu Gln Ala Gly Phe Phe Leu Met Thr Lys Ile
65                  70                  75                  80

Leu Thr Met Pro Gln Ser Leu Asp Ser Trp Trp Thr Ser Leu Asn Phe
                85                  90                  95

Leu Gly Gly Thr Thr Val Arg Pro Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Lys Phe Leu Trp Glu Trp Ala Ser Ala Arg
210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Ile Ile Trp Tyr Trp
                245                 250                 255

Gly Pro Asn Leu Tyr Asn Ile Leu Asn Pro Phe Ile Pro Leu Leu Pro
            260                 265                 270

Ile Phe Phe Cys Leu Trp Val Tyr Ile
        275                 280

```
<210> SEQ ID NO 31
<211> LENGTH: 846
<212> TYPE: DNA
<213> ORGANISM: Artificial Sequence
<220> FEATURE:
<223> OTHER INFORMATION: synthetic nucleic acid
```

<400> SEQUENCE: 31

```
atgcagtgga attccactgc cttccaccaa actctgcagg atcccagagt caggggtctg    60
tatcttcctg ctggtggctc cagctcagga acagtaaacc ctgctccgaa tattgcctct   120
cacatctcgt caatctccgc gaggattagg gaccctgcgc tgaacatgga aacatcgca    180
tcaggattcc taggacccct tctcgcatta caggcggtgt ttttcttgtt gacaaaaatc   240
ctcacaatgc cacagagtct agactcgtgg tggacttctc tcaattttct aggggaact    300
accgtgtgtc ttggccaaaa ttcgcagtcc ccaacctcca atcactcacc aacctcttgt   360
cctccaactt gtcctggtta cgctggatg tgtctgcggc gttttatcat cttcctcttc   420
atcctgctgc tatgcctcat cttcttgttg gttcttctgg actatcgagg tatgttgccc   480
gtttgtcctc taattccagg atcctcaaca accagcacgg gaccatgcaa acctgtatg    540
actaccgctc aaggaacctc tatgtatccc tcatgttgtt gtacaaaacc ttcggacgga   600
aattgcacct gtattccat cccatcatcc tgggctttcg caaaattcct atgggagtgg    660
gcctcagccc gtttctcctg gctcagttta ctagtgccat tgttcagtg gttcgtaggg    720
ctttcccca ctgtttggct ttcagttata tggatgatgt ggtattgggg accaagtctg    780
tacagcatct tgagtccctt cttgcctctg ttaccacttt tcttttggct ttgggtatac   840
atttaa                                                              846
```

<210> SEQ ID NO 32
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 32

```
Met Gln Trp Asn Ser Thr Ala Phe His Gln Thr Leu Gln Asp Pro Arg
  1               5                  10                  15

Val Arg Gly Leu Tyr Leu Pro Ala Gly Ser Ser Ser Gly Thr Val
                 20                  25                  30

Asn Pro Ala Pro Asn Ile Ala Ser His Ile Ser Ser Ile Ser Ala Arg
             35                  40                  45

Ile Arg Asp Pro Ala Leu Asn Met Glu Asn Ile Ala Ser Gly Phe Leu
         50                  55                  60

Gly Pro Leu Leu Ala Leu Gln Ala Val Phe Phe Leu Leu Thr Lys Ile
 65                  70                  75                  80

Leu Thr Met Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
                100                 105                 110

Ser Asn His Ser Pro Thr Ser Cys Pro Pro Thr Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Ala Gln Gly Thr Ser Met Tyr Pro Ser Cys
            180                 185                 190
```

```
Cys Cys Thr Lys Pro Ser Asp Gly Asn Cys Thr Cys Ile Pro Ile Pro
            195                 200                 205

Ser Ser Trp Ala Phe Ala Lys Phe Leu Trp Glu Trp Ala Ser Ala Arg
    210                 215                 220

Phe Ser Trp Leu Ser Leu Val Pro Phe Val Gln Trp Phe Val Gly
225                 230                 235                 240

Leu Ser Pro Thr Val Trp Leu Ser Val Ile Trp Met Met Trp Tyr Trp
                245                 250                 255

Gly Pro Ser Leu Tyr Ser Ile Leu Ser Pro Phe Leu Pro Leu Leu Pro
            260                 265                 270

Leu Phe Phe Trp Leu Trp Val Tyr Ile
            275                 280

<210> SEQ ID NO 33
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 33
atgcagtgga attctacaac cttccaccaa actctgcagg atcccagagt caggggtctg      60
tatcttcctg ctggtggctc cagttcagga acagtaaacc ctgctccgaa tattgcctct     120
cacatctcgt caatctccgc gaggactggg gaccctgcgc tgaacatgga gaacatcaca     180
tcaggattcc taggacccct tctcgtgtta caggcggggt ttttcttgtt gacaagaatc     240
ctcacaatac cacagagtct agactcgtgg tggacttctc tcaattttct agggggagca     300
cccgtgtgtc ctggccaaaa ttcgcagtcc ccaacctcca atcactcacc aacctcttgt     360
cctccgattt gtcctggcta tcgctggatg tgtctgcggc gttttatcat cttcctcttc     420
atcctgctgc tatgcctcat cttcttgttg gttcttctgg actatcgagg tatgttgccc     480
gtttgtcctc tacttccagg atcctcaaca accagcacgg gaccatgccg acctgcatg      540 actaccgctc aaggaacctc tatgtatccc tcatgttgct gtaccaaacc ttcggacgga     600
agctgcactt gtattcccat cccatcatcc tgggctttcg caaaattcct atgggagtgg     660
gcctcagccc gtttctcctg gctcagttta ctagtgccat tgttcagtg gttcgtaggg      720 ctttcccccg ctgtatggct ttcagttata tggatgattt ggtttgggg gccaagtctg     780 tacagcatct tgagtccctt tttaccgctg ttaccaattt tcttttgtct ttgggtatac     840
atttaa                                                               846

<210> SEQ ID NO 34
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 34

Met Gln Trp Asn Ser Thr Thr Phe His Gln Thr Leu Gln Asp Pro Arg
1               5                   10                  15

Val Arg Gly Leu Tyr Leu Pro Ala Gly Gly Ser Ser Gly Thr Val
            20                  25                  30

Asn Pro Ala Pro Asn Ile Ala Ser His Ile Ser Ser Ile Ser Ala Arg
            35                  40                  45

Thr Gly Asp Pro Ala Leu Asn Met Glu Asn Ile Thr Ser Gly Phe Leu
        50                  55                  60
```

Gly Pro Leu Leu Val Leu Gln Ala Gly Phe Phe Leu Thr Arg Ile
65                  70                  75                  80

Leu Thr Ile Pro Gln Ser Leu Asp Ser Trp Thr Ser Leu Asn Phe
            85                  90                  95

Leu Gly Gly Thr Thr Val Cys Leu Gly Leu Asn Ser Gln Ser Pro Thr
                100                 105                 110

Ser Asn His Ser Pro Thr Ser Cys Pro Pro Thr Cys Pro Gly Tyr Arg
            115                 120                 125

Trp Met Cys Leu Arg Arg Phe Ile Phe Leu Phe Ile Leu Leu Leu
130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Pro Gln Gly Thr Ser Met Tyr Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Gly Lys Phe Leu Trp Glu Trp Ala Ser Ala Arg
210                 215                 220

Phe Ser Trp Leu Ser Leu Leu Val Pro Phe Val Gln Trp Phe Val Gly
225                 230                 235                 240

Leu Ser Pro Thr Ala Trp Leu Leu Ala Ile Trp Ile Ile Trp Tyr Trp
                245                 250                 255

Gly Pro Asn Leu Tyr Asn Ile Leu Asn Pro Phe Leu Pro Leu Leu Pro
            260                 265                 270

Ile Phe Phe Cys Leu Trp Val Tyr Ile
275                 280

<210> SEQ ID NO 35
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 35

```
atgcagtgga attctacaac cttccaccaa actctgcagg atcccagagt caggggtctg        60
tatcttcctg ctggtggctc cagttcagga acagtaaacc ctgctccgaa tattgcctct       120
cacatctcgt caatctccgc gaggactggg gaccctgcgc tgaacatgga gaacatcaca       180
tcaggattcc taggacccct tctcgtgtta caggcggggt ttttcttgtt gacaagaatc       240
ctcacaatac cacagagtct agactcgtgg tggacttctc tcaattttct agggggaact       300
accgtgtgtc ttggcctaaa ttcgcagtcc ccaacctcca atcactcacc aacctcttgt       360
cctccaactt gtcctggtta cgctggatg tgtctgcggc gttttatcat cttcctcttc       420
atcctgcttc tatgcctcat cttcttgttg gttcttctgg actatcaagg tatgttgccc       480
gtttgtcccc taattccagg atcctcaaca accagcacgg gaccatgcaa aacctgtatg       540
actacccctc aaggaacctc tatgtatccc tcatgttgct gtaccaaacc ttcggacgga       600
aattgcacct gtattcccat cccatcatcc tgggctttcg gaaaattcct atgggagtgg       660
gcctcagccc gtttctcctg gctcagttta ctagtgccat tgttcagtg gttcgtaggg       720 ctttccccca ctgcttggct tttggctata tggatcatct ggtattgggg gccaaatctg       780
```
tacaacatct tgaatccctt tttaccgctg ttaccaattt tcttttgtct ttgggtatac    840
atttaa    846

<210> SEQ ID NO 36
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 36

```
Met Gln Trp Asn Ser Thr Thr Phe His Gln Thr Leu Gln Asp Pro Arg
 1               5                  10                  15

Val Arg Gly Leu Tyr Leu Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Ala Leu Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Thr Val Cys Leu Gly Leu Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Pro Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Ala Trp Leu Leu Ala Ile Trp Ile Ile Trp Tyr Trp
                245                 250                 255

Gly Pro Asn Leu Tyr Asn Ile Leu Asn Pro Phe Leu Pro Leu Leu Pro
            260                 265                 270

Ile Phe Phe Cys Leu Trp Val Tyr Ile
        275                 280
```

<210> SEQ ID NO 37
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 37
atgcagtgga attccacaac cttccaccaa actctgcagg atcccagagt cagggtctg    60

```
tatcttcctg ctggtggctc cagttcagga acagtaaacc ctgctccgaa tactgcctct    120
cacatctcgt cagtcttctc gacgactggg gaccctgcac cgaacatgga gaacatcaca    180
tcaggattcc taggacccct gctcgtgtta caggcggggt ttttcttgtt gacaaaaatc    240
ctcacaatgc cacagagtct agactcgttg tggacttctc tcaatttcct aggggggaaca   300 ccagcgtgtc ttggccaaaa ttcgcagtcc ccaaccccca atcactcacc aacctcttgc    360
cctccaactt gtcctggtta tcgctggatg tgtctgcggc gttttatcat cttcctcttc    420
atcctgcttc tatgcctcat cttcttgttg gttcttctgg actatcgagg tatgttgccc    480
gtttgtcctc taattccagg atcctcaaca accagcacgg gaccatgcaa aacctgtatg    540
actacccctc aaggaacctc tatgtatccc tcatgttgct gtaccaaacc ttcggacgga    600
aattgcacct gtattcccat cccatcatcc tgggctttcg gaaaattcct atgggagtgg    660
gcctcagccc gtttctcctg gctcagttta ctagtgccat tgttcagtg gttcgtaggg     720 ctttccccca ctgcttggct tttggctata tggatcatct ggtattgggg gccaaatctg    780
tacaacatct tgaatccctt tttaccgctg ttaccaattt tcttttgtct ttgggtatac    840
atttaa                                                                846
```

<210> SEQ ID NO 38
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 38

```
Met Gln Trp Asn Ser Thr Thr Phe His Gln Thr Leu Gln Asp Pro Arg
  1               5                  10                  15

Val Arg Gly Leu Tyr Leu Pro Ala Gly Gly Ser Ser Ser Gly Thr Val
                 20                  25                  30

Asn Pro Ala Pro Asn Thr Ala Ser His Ile Ser Ser Val Phe Ser Thr
             35                  40                  45

Thr Gly Asp Pro Ala Pro Asn Met Glu Asn Ile Thr Ser Gly Phe Leu
         50                  55                  60

Gly Pro Leu Leu Val Leu Gln Ala Gly Phe Phe Leu Leu Thr Lys Ile
 65                  70                  75                  80

Leu Thr Met Pro Gln Ser Leu Asp Ser Leu Trp Thr Ser Leu Asn Phe
                 85                  90                  95

Leu Gly Gly Thr Pro Ala Cys Leu Gly Gln Asn Ser Gln Ser Pro Thr
            100                 105                 110

Pro Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Pro Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Ala Arg
```

Phe Ser Trp Leu Ser Leu Leu Val Pro Phe Val Gln Trp Phe Val Gly
225                 230                 235                 240

Leu Ser Pro Thr Ala Trp Leu Leu Ala Ile Trp Ile Ile Trp Tyr Trp
            245                 250                 255

Gly Pro Asn Leu Tyr Asn Ile Leu Asn Pro Phe Leu Pro Leu Leu Pro
            260                 265                 270

Ile Phe Phe Cys Leu Trp Val Tyr Ile
            275                 280

<210> SEQ ID NO 39
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 39
atgcagtgga attccactgc cttccaccaa actctgcagg atcccagagt caggggtctg      60
tatctccctg ctggtggctc cagttcagga acagtaaacc ctgctccgaa tattgcctct     120
cacatctcgt caatctccgc gaggactggg gaccctgcac cgaacatgga gaacatcaca     180
tcaggattcc taggacccct gctcgtgtta caggcggtgt tttcttgtt gacaagaatc      240 ctcacaatac cgcagagtct agactcgtgg tggacttctc tcaattttct aggggggaaca    300 cccgtgtgtc ctggccaaaa ttcgcagtcc ccaacctcca atcactcacc aacctcttgt     360
cctccaactt gtcctggtta tcgctggatg tgtctgcggc gttttatcat cttcctcttc     420
atcctgcttc tatgcctcat cttcttgttg gttcttctgg actatcaagg tatgttgccc     480
gtttgtcccc taattccagg atcctcaaca accagcacgg gaccatgcaa acctgtatg      540 actacccctc aaggaaccctc tatgtatccc tcatgttgct gtaccaaacc ttcggacgga    600
aattgcacct gtattcccat cccatcatcc tgggctttcg gaaaattcct atgggagtgg     660
gcctcagccc gtttctcctg gctcagttta ctagtgccat tgttcagcg ttcgcaggg      720 ctttccccca ctgtttggct ttcagttata tggatgattt ggttttgggg gccaagtctg     780
tacagcatct tgagtccctt tttaccgctg ttaccaattt tcttttgtct ttgggtatac     840
atttaa                                                                846

<210> SEQ ID NO 40
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 40

Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Gly Thr Val
                20                  25                  30

Asn Pro Ala Pro Asn Ile Ala Ser His Ile Ser Ser Ile Ser Ala Arg
            35                  40                  45

Thr Gly Asp Pro Ala Pro Asn Met Glu Asn Ile Thr Ser Gly Phe Leu
        50                  55                  60

Gly Pro Leu Leu Val Leu Gln Ala Val Phe Phe Leu Leu Thr Arg Ile
65                  70                  75                  80

```
Leu Thr Ile Pro Gln Ser Leu Asp Ser Trp Thr Ser Leu Asn Phe
                85                  90                  95
Leu Gly Gly Thr Pro Val Cys Pro Gly Gln Asn Ser Gln Ser Pro Thr
            100                 105                 110
Ser Asn His Ser Pro Thr Ser Cys Pro Thr Cys Pro Gly Tyr Arg
        115                 120                 125
Trp Met Cys Leu Arg Arg Phe Ile Ile Phe Leu Phe Ile Leu Leu Leu
    130                 135                 140
Cys Leu Ile Phe Leu Leu Val Leu Leu Asp Tyr Gln Gly Met Leu Pro
145                 150                 155                 160
Val Cys Pro Leu Ile Pro Gly Ser Ser Thr Thr Ser Thr Gly Pro Cys
                165                 170                 175
Lys Thr Cys Met Thr Thr Pro Gln Gly Thr Ser Met Tyr Pro Ser Cys
                180                 185                 190
Cys Cys Thr Lys Pro Ser Asp Gly Asn Cys Thr Cys Ile Pro Ile Pro
            195                 200                 205
Ser Ser Trp Ala Phe Gly Lys Phe Leu Trp Glu Trp Ala Ser Ala Arg
    210                 215                 220
Phe Ser Trp Leu Ser Leu Leu Val Pro Phe Val Gln Arg Phe Ala Gly
225                 230                 235                 240
Leu Ser Pro Thr Val Trp Leu Ser Val Ile Trp Met Ile Trp Phe Trp
                245                 250                 255
Gly Pro Ser Leu Tyr Ser Ile Leu Ser Pro Phe Leu Pro Leu Leu Pro
                260                 265                 270
Ile Phe Phe Cys Leu Trp Val Tyr Ile
            275                 280

<210> SEQ ID NO 41
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 41
atgcagtgga attccacaac cttccaccaa actctgcaag atcccagagt gagaggcctg      60
tatttccctg ctggtggctc cagttcagga acagtaaacc ctgttctgac tactgcctct     120
cccgtatcgt caatcttctc gaggattggg accctgcgc tgaacatgga aacatcaca      180 tcaggattcc taggacccct tctcgtgtta caggcggggt ttttcttgtt gacaagaatc     240
ctcacaatac cgcagagtct agactcgttg tggacttctc tcagttttcc aaggggcata     300
ccagagtgca ctggccaaaa ttcgcagtcc caacctcca atcactcacc aacctcttgt     360
cctccaactt gtcctggtta cgctggatg tgtctgcgc gttttatcat cttcctcttc     420
atcctgctgc tatgcctcat cttcttgttg gttcttctgg actatcgagg tatgttgccc     480
gtttgtcctc tacttccagg atcctcaaca accagcacgg gaccctgcag gacctgtatg     540
actaccgctc aaggaacctc tatgtatccc tcatgttgct gtaccaaacc ttcggacgga     600
aattgcacct gtattcccat ccatcatcc tgggctttcg caaaattcct atgggagtgg     660
gcctcagccc gtttctcctg gctcagttta ctagtgccat tgttcagtg gttcgtaggg     720 ctttccccca ctgtttggct ttcagttata tggatcatct ggtattgggg ccaaatctg     780 tacaacatct tgaatccatt tataccgctg ttaccaattt tcttttgtct ttgggtatac     840
atttaa                                                                846
```

<210> SEQ ID NO 42
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 42

```
Met Gln Trp Asn Ser Thr Thr Phe His Gln Thr Leu Gln Asp Pro Arg
  1               5                  10                  15

Val Arg Gly Leu Tyr Phe Pro Ala Gly Gly Ser Ser Ser Gly Thr Val
                 20                  25                  30

Asn Pro Val Leu Thr Thr Ala Ser Pro Val Ser Ser Ile Phe Ser Arg
             35                  40                  45

Ile Gly Asp Pro Ala Leu Asn Met Glu Asn Ile Thr Ser Gly Phe Leu
         50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Leu Trp Thr Ser Leu Ser Phe
                 85                  90                  95

Pro Arg Gly Ile Pro Glu Cys Thr Gly Gln Asn Ser Gln Ser Pro Thr
                100                 105                 110

Ser Asn His Ser Pro Thr Ser Cys Pro Pro Thr Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Ile Trp Tyr Trp
                245                 250                 255

Gly Pro Asn Leu Tyr Asn Ile Leu Asn Pro Phe Ile Pro Leu Leu Pro
                260                 265                 270

Ile Phe Phe Cys Leu Trp Val Tyr Ile
        275                 280
```

<210> SEQ ID NO 43
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 43

```
atgcagtgga attccacaac cttccaccaa actctgcaag atcccagagt gagaggcctg      60
tatttccctg ctggtggctc cagttcagga acagtaaacc ctgttctgac tactgcctct     120
cccttatcgt caatcttctc gaggattggg gaccctgcgc tgaacatgga aacatcaca      180
```

```
tcaggattcc taggacccct tctcgtgtta caggcggggt ttttcttgtt gacaagaatc    240
ctcacaatac cgcagagtct agactcgttg tggacctctc tcagttttcc aggggggcata   300 ccagagtgca ctggccaaaa ttcgcagtcc ccaacctcca atcactcacc aacctcttgt    360
cctccaactt gtcctggtta tcgctggatg tgtctgcggc gttttatcat cttcctcttc    420
atcctgctgc tatgcctcat cttcttgttg gttcttctgg actatcgagg tatgttgccc    480
gtttgtcctc tacttccagg atcctcaaca accagcacgg gaccctgcag gacctgtatg    540
actaccgctc aaggaacctc tatgtatccc tcatgttgct gtaccaaacc ttcggacgga    600
aattgcacct gtattcccat cccatcatcc tgggctttcg gaaaattcct atgggagtgg    660
gcctcagtcc gtttctcctg gctcagttta ctagctccat ttgttcagcg gttcgtaggg    720
ctttccccca ctgtttggct ttcagttata tggatgatgt ggttctgggg gccaagtctg    780
ttcagcatct tgagtccctt cttgcctctg ttaccacttt tcttttggct ttgggtatac    840
atttaa                                                                846
```

<210> SEQ ID NO 44
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 44

```
Met Gln Trp Asn Ser Thr Thr Phe His Gln Thr Leu Gln Asp Pro Arg
  1               5                  10                  15

Val Arg Gly Leu Tyr Phe Pro Ala Gly Ser Ser Ser Gly Thr Val
                 20                  25                  30

Asn Pro Val Leu Thr Thr Ala Ser Pro Leu Ser Ser Ile Phe Ser Arg
             35                  40                  45

Ile Gly Asp Pro Ala Leu Asn Met Glu Asn Ile Thr Ser Gly Phe Leu
         50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Leu Trp Thr Ser Leu Ser Phe
                 85                  90                  95

Pro Gly Gly Ile Pro Glu Cys Thr Gly Gln Asn Ser Gln Ser Pro Thr
                100                 105                 110

Ser Asn His Ser Pro Thr Ser Cys Pro Pro Thr Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Gly Lys Phe Leu Trp Glu Trp Ala Ser Val Arg
    210                 215                 220

Phe Ser Trp Leu Ser Leu Leu Ala Pro Phe Val Gln Arg Phe Val Gly
225                 230                 235                 240
```

Leu Ser Pro Thr Val Trp Leu Ser Val Ile Trp Met Met Trp Phe Trp
                245                 250                 255

Gly Pro Ser Leu Phe Ser Ile Leu Ser Pro Phe Leu Pro Leu Pro
            260                 265                 270

Leu Phe Phe Trp Leu Trp Val Tyr Ile
        275                 280

<210> SEQ ID NO 45
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 45

| | | |
|---|---|---|
| atgcagtgga attccactgc cttccaccaa actctgcagg atcccagagt caggggtctg | 60 |
| tatcttcctg ctggtggctc cagctcagga acagtaaacc ctgctccgaa tattgcctct | 120 |
| cacatctcgt caatccccgc gaggattggg gaccctgcgc tgaacatgga aacatcaca | 180 |
| tcaggattcc taggacccct tctcgcatta caggcggtgt ttttcttgtt gacaaaaatc | 240 |
| ctcacaatgc cacagagtct agactcgtgg tggacttctc tcaattttct aggggaact | 300 |
| accgtgtgtc ttggcctaaa ttcgcagtcc ccaacctcca atcactcacc aacctcttgt | 360 |
| cctccaactt gtcctggtta cgctggatg tgtctgcggc gttttatcat cttcctcttc | 420 |
| atcctgctgc tgtgcctcat cttcttgttg gttcttctgg actatcgagg tatgttgccc | 480 |
| gtttgtcctc tacttccagg atcctcaaca accagcacgg gaccatgccg gacctgcatg | 540 |
| actaccgctc aaggaaccctc tatgtatccc tcatgttgct gtaccaaacc ttcggacgga | 600 |
| agctgcactt gtattcccat cccctcatcc tgggctttcg gaaaattcct atgggagtgg | 660 |
| gcctcagtcc gtttctcctg gctcagttta ctagtgccat tgttcagtg gttcgcaggg | 720 |
| ctttcccca ctgtatggct tttagttata tggatgatgg ggtctgggg gccaagtctg | 780 |
| ttcagcatct tgagtccctt cttgcctctg ttaccaattt tcttttgtct ttgggtatac | 840 |
| atttaa | 846 |

<210> SEQ ID NO 46
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 46

Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Gly Thr Val
            20                  25                  30

Asn Pro Ala Pro Asn Ile Ala Ser His Ile Ser Ser Ile Ser Ala Arg
            35                  40                  45

Ile Gly Asp Pro Ala Leu Asn Met Glu Asn Ile Thr Ser Gly Phe Leu
    50                  55                  60

Gly Pro Leu Leu Ala Leu Gln Ala Val Phe Phe Leu Leu Thr Lys Ile
65                  70                  75                  80

Leu Thr Met Pro Gln Ser Leu Asp Ser Trp Trp Thr Ser Leu Asn Phe
                85                  90                  95

Leu Gly Gly Thr Thr Val Cys Leu Gly Leu Asn Ser Gln Ser Pro Thr

```
                100              105              110
Ser Asn His Ser Pro Thr Ser Cys Pro Pro Thr Cys Pro Gly Tyr Arg
            115                  120                  125

Trp Met Cys Leu Arg Arg Phe Ile Ile Phe Leu Phe Ile Leu Leu Leu
130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Arg Thr Cys Met Thr Thr Ala Gln Gly Thr Ser Met Tyr Pro Ser Cys
                180                 185                 190

Cys Cys Thr Lys Pro Ser Asp Gly Ser Cys Thr Cys Ile Pro Ile Pro
            195                 200                 205

Ser Ser Trp Ala Phe Gly Lys Phe Leu Trp Glu Trp Ala Ser Val Arg
        210                 215                 220

Phe Ser Trp Leu Ser Leu Leu Val Pro Phe Val Gln Trp Phe Ala Gly
225                 230                 235                 240

Leu Ser Pro Thr Val Trp Leu Val Ile Trp Met Met Trp Phe Trp
                245                 250                 255

Gly Pro Ser Leu Phe Ser Ile Leu Ser Pro Phe Leu Pro Leu Pro
            260                 265                 270

Ile Phe Phe Cys Leu Trp Val Tyr Ile
            275                 280

<210> SEQ ID NO 47
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 47
atgcagtgga attccactgc cttccaccaa actctgcagg atcccagagt caggggtctg      60
tatcttcctg ctggtggctc cagttcagga acagtaaacc ctgctccgaa tattgcctct     120
cccttatcgt caatcttctc gacgactggg gaccctgcgc tgaacatgga gaacatcaca     180
tcaggattcc taggacccct tctcgtgtta caggcggggt ttttcttgtt gacaagaatc     240
ctcacaatac cgcagagtct agactcgtgg tggacttctc tcaattttct aggggagca     300
cccgtgtgtc ttggccaaaa ttcgcagtcc ccaacctcca atcactcacc aacctcttgt     360
cctccaactt gtcctggtta cgctggatg tgtctgcggc gttttatcat cttcctcttc     420
atcctgctgc tatgcctcat cttcttgttg gttcttctgg actatcgagg tatgttgccc     480
gtttgtcctc taattccagg atcctcaaca accagcacgg gaccctgcag gacctgtatg     540
actgccgctc aaggaaccctc tatgtatccc tcatgttgct gtaccaaacc ttcggacgga     600
aattgcacct gtattcccat cccatcatcc tgggctttcg caaaattcct atgggagtgg     660
gcctcagccc gtttctcctg gctcagttta ctagtgccat tgttcagtg gttcgtaggg     720
ctttccccca ctgtttggct ttcagttata tggatcatct ggtattgggg gccaaatctg     780
tacaacatct tgaatccatt tataccgctg ttaccaattt tctttttgtct ttgggtatac     840
atttaa                                                                846

<210> SEQ ID NO 48
<211> LENGTH: 281
<212> TYPE: PRT
```

<213> ORGANISM: Artificial Sequence
<220> FEATURE:
<223> OTHER INFORMATION: synthetic polypeptide

<400> SEQUENCE: 48

```
Met Gln Trp Asn Ser Thr Ala Phe His Gln Thr Leu Gln Asp Pro Arg
 1               5                  10                  15

Val Arg Gly Leu Tyr Leu Pro Ala Gly Ser Ser Ser Gly Thr Val
            20                  25                  30

Asn Pro Ala Pro Asn Ile Ala Ser Pro Leu Ser Ser Ile Phe Ser Thr
        35                  40                  45

Thr Gly Asp Pro Ala Leu Asn Met Glu Asn Ile Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Ala Pro Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Arg Thr Cys Met Thr Ala Ala Gln Gly Thr Ser Met Tyr Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Lys Phe Leu Trp Glu Trp Ala Ser Ala Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Ile Trp Ile Ile Trp Tyr Trp
                245                 250                 255

Gly Pro Asn Leu Tyr Asn Ile Leu Asn Pro Phe Ile Pro Leu Leu Pro
            260                 265                 270

Ile Phe Phe Cys Leu Trp Val Tyr Ile
        275                 280
```

<210> SEQ ID NO 49
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 49

```
atgcagtgga attccacaac cttccaccaa actctgcagg atcccagagt caggggtctg      60
tatcttcctg ctggtggctc cagttcagga acagtaaacc ctgctccgaa tactgcctct     120
cacatctcgt cagtcttctc gacgactggg accctgcac  cgaacatgga gaacatcaca     180
tcaggattcc taggacccct gctcgtgtta caggcgggt  ttttcttgtt gacaaaaatc     240
ctcacaatgc cacagagtct agactcgttg tggacttctc tcaatttttct aggggggaaca    300
```

```
ccagcgtgtc ttggccaaaa ttcgcagtcc ccaacctcca atcactcacc aacctcttgt   360
cctccaactt gtcctggtca tcgctggatg tgtctgcggc gttttatcat cttcctcttc   420
atcctgctgc tatgcctcat cttcttgttg gttcttctgg actatcgagg tatgttgccc   480
gtttgtcctc taattccagg atcctcaaca accagcacgg gaccatgcaa aacctgtatg   540
actacccctc aaggaacctc tatgtatccc tcatgttgct gtaccaaacc ttcggacgga   600
aattgcacct gtattccat cccatcatcc tgggctttcg gaaaattcct atggagtgg    660 gcctcagccc gtttctcctg gctcagttta ctagtgccat tgttcagtg gttcgtaggg   720 ctttccccca ctgcttggct tttggctata tggatcatct ggtattgggg gccaaatctg   780
tacaacatct tgaatccctt tttaccgctg ttaccaattt tctttttgtct ttgggtatac  840 atttaa                                                              846
```

```
<210> SEQ ID NO 50
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 50

Met Gln Trp Asn Ser Thr Thr Phe His Gln Thr Leu Gln Asp Pro Arg
 1               5                  10                  15

Val Arg Gly Leu Tyr Leu Pro Ala Gly Gly Ser Ser Ser Gly Thr Val
                20                  25                  30

Asn Pro Ala Pro Asn Thr Ala Ser His Ile Ser Ser Val Phe Ser Thr
            35                  40                  45

Thr Gly Asp Pro Ala Pro Asn Met Glu Asn Ile Thr Ser Gly Phe Leu
        50                  55                  60

Gly Pro Leu Leu Val Leu Gln Ala Gly Phe Phe Leu Leu Thr Lys Ile
 65                  70                  75                  80

Leu Thr Met Pro Gln Ser Leu Asp Ser Leu Trp Thr Ser Leu Asn Phe
                85                  90                  95

Leu Gly Gly Thr Pro Ala Cys Leu Gly Gln Asn Ser Gln Ser Pro Thr
               100                 105                 110

Ser Asn His Ser Pro Thr Ser Cys Pro Pro Thr Cys Pro Gly His Arg
           115                 120                 125

Trp Met Cys Leu Arg Arg Phe Ile Ile Phe Leu Phe Ile Leu Leu Leu
       130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
               165                 170                 175

Lys Thr Cys Met Thr Thr Pro Gln Gly Thr Ser Met Tyr Pro Ser Cys
           180                 185                 190

Cys Cys Thr Lys Pro Ser Asp Gly Asn Cys Thr Cys Ile Pro Ile Pro
       195                 200                 205

Ser Ser Trp Ala Phe Gly Lys Phe Leu Trp Glu Trp Ala Ser Ala Arg
   210                 215                 220

Phe Ser Trp Leu Ser Leu Leu Val Pro Phe Val Gln Trp Phe Val Gly
225                 230                 235                 240

Leu Ser Pro Thr Ala Trp Leu Leu Ala Ile Trp Ile Ile Trp Tyr Trp
               245                 250                 255
```

```
Gly Pro Asn Leu Tyr Asn Ile Leu Asn Pro Phe Leu Pro Leu Pro
            260                 265                 270

Ile Phe Phe Cys Leu Trp Val Tyr Ile
        275                 280

<210> SEQ ID NO 51
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 51
atgcagtgga attccacaac cttccaccaa actctgcagg atcccagagt caggggtctg      60
tatcttcctg ctggtggctc cagttcagga acagtaaacc ctgctccgaa tactgcctct     120
cacatctcgt cagtcttctc gacgactggg gaccctgcac cgaacatgga gaacatcaca     180
tcaggattcc taggacccct gctcgtgtta caggcggggt ttttcttgtt gacaaaaatc     240
ctcacaatgc cacagagtct agactcgttg tggacttctc tcaattttct aggggggaaca    300 ccagcgtgtc ttggccaaaa ttcgcagtcc caacctcca atcactcacc aacctcttgt      360
cctccaactt gtcctggtca tcgctggatg tgtctgcggc gttttatcat cttcctcttc     420
atcctgctgc tatgcctcat cttcttgttg gttcttctgg actatcgagg tatgttgccc     480
gtttgtcctc taattccagg atcctcaaca accagcacgg gaccatgcaa acctgtatg     540 actacccctc aaggaacctc tatgtatccc tcatgttgct gtaccaaacc ttcggacgga     600
aattgcacct gtattcccat cccatcatcc tgggctttcg gaaaattcct atgggagtgg     660
gcctcagccc gtttctcctg gctcagttta ctagtgccat tgttcagtg gttcgtaggg      720 ctttccccca ctgcttggct tttggctata tggatcatct ggtattgggg gccaaatctg     780
tacaacatct tgaatccctt tttaccgctg ttaccaattt tcttttgtct ttgggtatac     840
atttaa                                                                846

<210> SEQ ID NO 52
<211> LENGTH: 281
<212> TYPE: PRT
<213> ORGANISM: Artificial Sequence
<220> FEATURE:
<223> OTHER INFORMATION: synthetic polypeptide

<400> SEQUENCE: 52

Met Gln Trp Asn Ser Thr Ala Phe His Gln Thr Leu Gln Asp Pro Arg
  1               5                  10                  15

Val Arg Gly Leu Tyr Leu Pro Ala Gly Gly Ser Ser Ser Gly Thr Val
             20                  25                  30

Asn Pro Ala Pro Asn Ile Ala Ser His Ile Ser Ser Ile Ser Ala Arg
         35                  40                  45

Ile Gly Asp Pro Ala Leu Asn Met Glu Asn Ile Thr Ser Gly Phe Leu
     50                  55                  60

Gly Pro Leu Leu Ala Leu Gln Ala Val Phe Phe Leu Leu Thr Lys Ile
 65                  70                  75                  80

Leu Thr Met Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125
```

```
Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Arg Gly Met Leu Pro
145                 150                 155                 160

Val Cys Pro Leu Ile Pro Gly Ser Ser Thr Thr Ser Thr Gly Pro Cys
                165                 170                 175

Lys Thr Cys Met Thr Thr Ala Gln Gly Thr Ser Met Tyr Pro Ser Cys
                180                 185                 190

Cys Cys Thr Lys Pro Ser Asp Gly Asn Cys Thr Cys Ile Pro Ile Pro
                195                 200                 205

Ser Ser Trp Ala Phe Gly Lys Phe Leu Trp Glu Trp Ala Ser Ala Arg
        210                 215                 220

Phe Ser Trp Leu Ser Leu Leu Ala Pro Phe Val Gln Arg Phe Ala Gly
225                 230                 235                 240

Leu Ser Pro Thr Ala Trp Leu Leu Ala Ile Trp Ile Ile Trp Tyr Trp
                245                 250                 255

Gly Pro Asn Leu Tyr Asn Ile Met Asn Pro Phe Leu Pro Leu Leu Pro
                260                 265                 270

Ile Phe Phe Cys Leu Trp Val Tyr Ile
                275                 280

<210> SEQ ID NO 53
<211> LENGTH: 846
<212> TYPE: DNA
<213> ORGANISM: Artificial Sequence
<220> FEATURE:
<223> OTHER INFORMATION: synthetic nucleic acid

<400> SEQUENCE: 53
atgcagtgga attccactgc cttccaccaa actctgcagg atcccagagt caggggtctg      60
tatcttcctg ctggtggctc cagttcagga acagtaaacc ctgctccgaa tactgcctct     120
cacatctcgt cagtcttctc gacgactggg gaccctgcac cgaacatgga gaacatcaca     180
tcaggattcc taggacccct gctcgtgtta caggcggggt ttttcttgtt gacaaaaatc     240
ctcacaatgc cacagagtct agactcgttg tggacttctc tcaattttct agggggaaca     300
ccagcgtgtc ttggccaaaa ttcgcagtcc caacctcca atcactcacc aacctcttgt      360
cctccaactt gtcctggtta tcactggatg tgtctgcggc gttttatcat cttcctcttc     420
atcctgctgc tatgcctcat cttcttgttg gttcttctgg actatcgagg tatgttgccc     480
gtttgtcctc tacttccagg atcatcgacc accagcacgg gaccatgcaa acctgcacg      540 atccctgctc aaggaaccct tttgattccc tcatgttgtt gtacaaaacc ttcggacgga     600
aattgcactt gtattcccat cccatcgtct gggctttcg caaaattcct atgggagtgg      660
gcctcagccc gtttctcctg gctcagttta ctagtgccat tgttcagcg gttcgcaggg     720 ctttccccca ctgtttggct ttcagttata tggatgattt ggttttgggg gccaagtctg     780
tacagcatct tgagtccctt tttaccgctg ttaccaattt tcttttgtct ttgggtatac     840
atttaa                                                                846

<210> SEQ ID NO 54
<211> LENGTH: 281
<212> TYPE: PRT
<213> ORGANISM: Artificial Sequence
<220> FEATURE:
<223> OTHER INFORMATION: synthetic polypeptide
```

<400> SEQUENCE: 54

Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Ser Gly Thr Val
            20                  25                  30

Asn Pro Ala Pro Asn Thr Ala Ser His Ile Ser Ser Val Phe Ser Thr
        35                  40                  45

Thr Gly Asp Pro Ala Pro Asn Met Glu Asn Ile Thr Ser Gly Phe Leu
    50                  55                  60

Gly Pro Leu Leu Val Leu Gln Ala Gly Phe Phe Leu Leu Thr Lys Ile
65                  70                  75                  80

Leu Thr Met Pro Gln Ser Leu Asp Ser Leu Trp Ser Leu Asn Phe
                85                  90                  95

Leu Gly Gly Thr Pro Ala Cys Leu Gly Gln Asn Ser Gln Ser Pro Thr
                100                 105                 110

Ser Asn His Ser Pro Thr Ser Cys Pro Pro Thr Cys Pro Gly Tyr His
            115                 120                 125

Trp Met Cys Leu Arg Arg Phe Ile Ile Phe Leu Phe Ile Leu Leu Leu
130                 135                 140

Cys Leu Ile Phe Leu Leu Val Leu Leu Asp Tyr Arg Gly Met Leu Pro
145                 150                 155                 160

Val Cys Pro Leu Leu Pro Gly Ser Ser Thr Thr Ser Thr Gly Pro Cys
                165                 170                 175

Lys Thr Cys Thr Ile Pro Ala Gln Gly Thr Ser Leu Ile Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Ala Lys Phe Leu Trp Glu Trp Ala Ser Ala Arg
            210                 215                 220

Phe Ser Trp Leu Ser Leu Leu Val Pro Phe Val Gln Arg Phe Ala Gly
225                 230                 235                 240

Leu Ser Pro Thr Val Trp Leu Ser Val Ile Trp Met Ile Trp Phe Trp
                245                 250                 255

Gly Pro Ser Leu Tyr Ser Ile Leu Ser Pro Phe Leu Pro Leu Leu Pro
            260                 265                 270

Ile Phe Phe Cys Leu Trp Val Tyr Ile
            275                 280

<210> SEQ ID NO 55
<211> LENGTH: 840
<212> TYPE: DNA
<213> ORGANISM: Artificial Sequence
<220> FEATURE:
<223> OTHER INFORMATION: synthetic nucleic acid

<400> SEQUENCE: 55
atgcagtgga attctactgc cttccaccaa actctgcagg atcccagagt caggggtctg      60
tatcttcctg ctggtggctc cagttcagga acagtaaacc ctgctccgaa tattgcctct     120
cacatctcgt caatctccgc gaggactggg accctgtga cgaacatgtc accatcaagt     180
ctcctaggac tcctagcagg attacaggtg gtgtatttct tgtggacaaa atcctaaca     240 ataccgcaga gtctagactc gtggtggact ctctcaatt ttctagggg agcacccgtg      300 tgtcctggcc aaaattcgca gccccaacc cccaatcact accaacctc ttgtccttca      360 acttgtcctg ggtatcgctg gatgcgtctg tggcgtttta tcatcttcct cttcatcctg      420

```
ctgctatgcc tcatcttctt gttggttctt ctggactatc gaggtgtgtt gcccgtttgt    480
cctccaattc caggatcctc aacaaccagc acgggaccat gcaaaacctg tatgactacc    540
gctcaaggaa cctctatgta tccctcatgt tgttgtacaa aaccttcgga cggaaattgc    600
acctgtattc ccatcccatc atcctgggct ttcggaaaat tcctatggga gtgggcctca    660
gcccgtttct cctggctcag tttactagtg ccatttgttc agtggttcgt agggcttttcc   720 cccactgctt ggcttttggc tacatggatc atctggtatt gggggccaaa tctgtacaac    780
atcttgaatc ccttttttacc gctgttacca attttctttt gtctttgggt atacatttaa   840
```

<210> SEQ ID NO 56
<211> LENGTH: 279
<212> TYPE: PRT
<213> ORGANISM: Artificial Sequence
<220> FEATURE:
<223> OTHER INFORMATION: synthetic polypeptide

<400> SEQUENCE: 56

```
Met Gln Trp Asn Ser Thr Ala Phe His Gln Thr Leu Gln Asp Pro Arg
1               5                   10                  15

Val Arg Gly Leu Tyr Leu Pro Ala Gly Gly Ser Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn Met Ser Pro Ser Ser Leu Leu Gly Leu
    50                  55                  60

Leu Ala Gly Leu Gln Val Val Tyr Phe Leu Trp Thr Lys Ile Leu Thr
65                  70                  75                  80

Ile Pro Gln Ser Leu Asp Ser Trp Trp Thr Ser Leu Asn Phe Leu Gly
                85                  90                  95

Gly Ala Pro Val Cys Pro Gly Gln Asn Ser Gln Pro Pro Thr Pro Asn
            100                 105                 110

His Ser Pro Thr Ser Cys Pro Ser Thr Cys Pro Gly Tyr Arg Trp Met
        115                 120                 125

Arg Leu Trp Arg Phe Ile Ile Phe Leu Phe Ile Leu Leu Leu Cys Leu
    130                 135                 140

Ile Phe Leu Leu Val Leu Leu Asp Tyr Arg Gly Val Leu Pro Val Cys
145                 150                 155                 160

Pro Pro Ile Pro Gly Ser Ser Thr Thr Ser Thr Gly Pro Cys Lys Thr
                165                 170                 175

Cys Met Thr Thr Ala Gln Gly Thr Ser Met Tyr Pro Ser Cys Cys Cys
            180                 185                 190

Thr Lys Pro Ser Asp Gly Asn Cys Thr Cys Ile Pro Ile Pro Ser Ser
        195                 200                 205

Trp Ala Phe Gly Lys Phe Leu Trp Glu Trp Ala Ser Ala Arg Phe Ser
    210                 215                 220

Trp Leu Ser Leu Leu Val Pro Phe Val Gln Trp Phe Val Gly Leu Ser
225                 230                 235                 240

Pro Thr Ala Trp Leu Leu Ala Thr Trp Ile Ile Trp Tyr Trp Gly Pro
                245                 250                 255

Asn Leu Tyr Asn Ile Leu Asn Pro Phe Leu Pro Leu Leu Pro Ile Phe
            260                 265                 270

Phe Cys Leu Trp Val Tyr Ile
        275
```

<210> SEQ ID NO 57
<211> LENGTH: 840
<212> TYPE: DNA
<213> ORGANISM: Artificial Sequence
<220> FEATURE:
<223> OTHER INFORMATION: synthetic nucleic acid

<400> SEQUENCE: 57

```
atgcagtgga attctactgc cttccaccaa actctgcagg atcccagagt caggggtctg      60
tatcttcctg ctggtggctc cagttcagga acagtaaacc ctgctccgaa tattgcctct     120
cacatctcgt caatctccgc gaggactggg gaccctgtga cgaacatgtc accatcaagt     180
ctcctaggac tcctcgcagg attacaggtg gtgtatttct gtggacaaa atcctaaca      240
ataccgcaga gtctagactc gtggtggact tctctcaatt ttctaggggg agcacccgtg     300
tgtcctggcc aaaattcgca gtccccaacc tccaatcact caccaacctc ttgtcctcca     360
acttgtcctg gttatcgctg gatgtgtctg cggcgtttta tcatcttcct cttcatcctg     420
ctgctatgcc tcatcttctt gttggttctt ctggactatc gaggtatgtt gcccgtttgt     480
cctctacttc caggatcctc aacaaccagc acgggaccct gcaggacctg tatgactacc     540
gctcaaggaa cctctatgta tccctcatgt tgctgtacca aaccttcgga cggaaattgc     600
acctgtattc ccatcccatc atcctgggct ttcgcaaaat tcctatggga gtgggcctca     660
gcccgtttct cctggctcag tttactagtg ccatttgttc agtggttcgt agggctttcc     720
cccactgttt ggctttcagt tatatggatc atctggtatt gggggccaaa tctgtacaac     780
atcttgagtc catttatacc gctgttacca attttctttt gtctttgggt atacatttaa     840
```

<210> SEQ ID NO 58
<211> LENGTH: 279
<212> TYPE: PRT
<213> ORGANISM: Artificial Sequence
<220> FEATURE:
<223> OTHER INFORMATION: synthetic polypeptide

<400> SEQUENCE: 58

```
Met Gln Trp Asn Ser Thr Ala Phe His Gln Thr Leu Gln Asp Pro Arg
  1               5                  10                  15

Val Arg Gly Leu Tyr Leu Pro Ala Gly Gly Ser Ser Gly Thr Val
                 20                  25                  30

Asn Pro Ala Pro Asn Ile Ala Ser His Ile Ser Ser Ile Ser Ala Arg
             35                  40                  45

Thr Gly Asp Pro Val Thr Asn Met Ser Pro Ser Ser Leu Leu Gly Leu
         50                  55                  60

Leu Ala Gly Leu Gln Val Val Tyr Phe Leu Trp Thr Lys Ile Leu Thr
 65                  70                  75                  80

Ile Pro Gln Ser Leu Asp Ser Trp Trp Thr Ser Leu Asn Phe Leu Gly
                 85                  90                  95

Gly Ala Pro Val Cys Pro Gly Gln Asn Ser Gln Ser Pro Thr Ser Asn
                100                 105                 110

His Ser Pro Thr Ser Cys Pro Pro Thr Cys Pro Gly Tyr Arg Trp Met
            115                 120                 125

Cys Leu Arg Arg Phe Ile Ile Phe Leu Phe Ile Leu Leu Leu Cys Leu
        130                 135                 140

Ile Phe Leu Leu Val Leu Leu Asp Tyr Arg Gly Met Leu Pro Val Cys
145                 150                 155                 160

Pro Leu Leu Pro Gly Ser Ser Thr Thr Ser Thr Gly Pro Cys Arg Thr
```

```
              165                 170                 175
Cys Met Thr Thr Ala Gln Gly Thr Ser Met Tyr Pro Ser Cys Cys Cys
            180                 185                 190

Thr Lys Pro Ser Asp Gly Asn Cys Thr Cys Ile Pro Ile Pro Ser Ser
        195                 200                 205

Trp Ala Phe Ala Lys Phe Leu Trp Glu Trp Ala Ser Ala Arg Phe Ser
    210                 215                 220

Trp Leu Ser Leu Leu Val Pro Phe Val Gln Trp Phe Val Gly Leu Ser
225                 230                 235                 240

Pro Thr Val Trp Leu Ser Val Ile Trp Ile Ile Trp Tyr Trp Gly Pro
                245                 250                 255

Asn Leu Tyr Asn Ile Leu Ser Pro Phe Ile Pro Leu Leu Pro Ile Phe
                260                 265                 270

Phe Cys Leu Trp Val Tyr Ile
                275

<210> SEQ ID NO 59
<211> LENGTH: 280
<212> TYPE: PRT
<213> ORGANISM: hepatitis B

<400> SEQUENCE: 59

Met Gln Trp Asn Ser Thr Thr Phe His Gln Thr Leu Gln Asp Pro Arg
  1                 5                  10                  15

Val Arg Gly Leu Tyr Phe Pro Ala Gly Gly Ser Ser Ser Gly Thr Val
                 20                  25                  30

Asn Pro Val Leu Thr Thr Ala Ser Pro Leu Ser Ser Ile Phe Ser Arg
             35                  40                  45

Ile Gly Asp Pro Ala Leu Asn Met Glu Asn Ile Thr Ser Gly Phe Leu
         50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Thr Thr Val Cys Leu Gly Gln Asn Ser Gln Ser Pro Thr
            100                 105                 110

Ser Asn His Ser Pro Thr Ser Cys Pro Pro Thr Cys Pro Gly Tyr Arg
        115                 120                 125

Trp Cys Leu Arg Arg Phe Ile Ile Phe Leu Phe Ile Leu Leu Leu Cys
130                 135                 140

Leu Ile Phe Leu Leu Val Leu Leu Asp Tyr Gln Gly Met Leu Pro Val
145                 150                 155                 160

Cys Pro Leu Ile Pro Gly Ser Ser Thr Thr Ser Thr Gly Pro Cys Arg
                165                 170                 175

Thr Cys Met Thr Thr Ala Gln Gly Thr Ser Met Tyr Pro Ser Cys Cys
                180                 185                 190

Cys Thr Lys Pro Ser Asp Gly Asn Cys Thr Cys Ile Pro Ile Pro Ser
            195                 200                 205

Ser Trp Ala Phe Gly Lys Phe Leu Trp Glu Trp Ala Ser Ala Arg Phe
        210                 215                 220

Ser Trp Leu Ser Leu Leu Val Pro Phe Val Gln Trp Phe Val Gly Leu
225                 230                 235                 240

Ser Pro Thr Val Trp Leu Ser Val Ile Trp Met Met Trp Tyr Trp Gly
                245                 250                 255
```

```
Pro Ser Leu Tyr Ser Ile Leu Ser Pro Phe Leu Pro Leu Leu Pro Ile
            260                 265                 270

Phe Phe Cys Leu Trp Val Tyr Ile
        275                 280
```

<210> SEQ ID NO 60
<211> LENGTH: 30
<212> TYPE: DNA
<213> ORGANISM: hepatitis B

<400> SEQUENCE: 60
tatgactacc gctcaaggaa cctctatgta                              30

<210> SEQ ID NO 61
<211> LENGTH: 59
<212> TYPE: DNA
<213> ORGANISM: hepatitis B

<400> SEQUENCE: 61
accatgcaaa cctgtatgac taccgctcaa ggaacctcta tgtatccctc atgttgttg    59

<210> SEQ ID NO 62
<211> LENGTH: 60
<212> TYPE: DNA
<213> ORGANISM: hepatitis B

<400> SEQUENCE: 62
accctgcagg acctgtatga ctaccgctca aggaacctct atgtatccct catgttgctg   60

<210> SEQ ID NO 63
<211> LENGTH: 60
<212> TYPE: DNA
<213> ORGANISM: hepatitis B

<400> SEQUENCE: 63
caattgcaga caatgtatga ctaccgctca aggaacctct atgtatcctt actgttgttg   60

<210> SEQ ID NO 64
<211> LENGTH: 21
<212> TYPE: DNA
<213> ORGANISM: Artificial Sequence
<220> FEATURE:
<223> OTHER INFORMATION: vector

<400> SEQUENCE: 64
gcagctcctt gctcctaaca g                                       21

<210> SEQ ID NO 65
<211> LENGTH: 21
<212> TYPE: DNA
<213> ORGANISM: Artificial Sequence
<220> FEATURE:
<223> OTHER INFORMATION: vector

<400> SEQUENCE: 65
gtatcacgag gcccttcgt c                                        21

<210> SEQ ID NO 66
<211> LENGTH: 20
<212> TYPE: DNA
<213> ORGANISM: Artificial Sequence
<220> FEATURE:
<223> OTHER INFORMATION: vector

<400> SEQUENCE: 66
gctgacagac taacagactg                                                    20

<210> SEQ ID NO 67
<211> LENGTH: 20
<212> TYPE: DNA
<213> ORGANISM: Artificial Sequence
<220> FEATURE:
<223> OTHER INFORMATION: vector

<400> SEQUENCE: 67
aacagatggc tggcaactag                                                    20

<210> SEQ ID NO 68
<211> LENGTH: 837
<212> TYPE: DNA
<213> ORGANISM: Artificial Sequence
<220> FEATURE:
<223> OTHER INFORMATION: synthetic nucleic acid

<400> SEQUENCE: 68
atgcagtgga attctactgc cttccaccaa actctgcagg atcccagagt caggggtctg        60
tatcttcctg ctggtggctc cagttcagga acagtaaacc ctgctccgaa tattgcctct       120
cacatctcgt caatctccgc gaggactggg gaccctgtga cgaacatgtc accatcaagt       180
ctcctaggac tcctcgcagg attacaggtg gtgtatttct gtggacaaa atcctaaca         240 ataccgcaga gtctagactc gtggtggact ctctcaatt ttctaggggg agcacccgtg        300
tgtcctggcc aaaattcgca gtccccaacc tccaatcact caccaacctc ttgtcctcca       360
atttgtcctg gttatcgctg gatgtgtctg cggcgtttta tcatcttcct cttcatcctg       420
cttctatgcc tcatcttctt gttggttctt ctggactatc aaggtatgtt gcccgtttgt       480
cctctaattc caggatcatc gaccaccagc acgggaccat gcaaaacctg tatgactacc       540
cctcaaggaa cctctatgta tccctcatgt tgttgtacca aaccttcgga cggaaattgc       600
acctgtattc ccatcccatc atcctgggct ttcggaaaat tcctatggga gtgggcctca       660
gtccgtttct cctggctcag tttactagct ccatttgttc agcggttcgt agggcttttcc      720 cccactgttt ggctttcagt tatatggatg atgtggttct gggggccaag tctgttcagc      780
atcttgagtc ccttcttgcc tctgttacca cttttctttt ggctttgggt atacatt          837

<210> SEQ ID NO 69
<211> LENGTH: 279
<212> TYPE: PRT
<213> ORGANISM: Artificial Sequence
<220> FEATURE:
<223> OTHER INFORMATION: synthetic polypeptide

<400> SEQUENCE: 69

Met Gln Trp Asn Ser Thr Ala Phe His Gln Thr Leu Gln Asp Pro Arg
 1               5                  10                  15

Val Arg Gly Leu Tyr Leu Pro Ala Gly Gly Ser Ser Gly Thr Val
            20                  25                  30

Asn Pro Ala Pro Asn Ile Ala Ser His Ile Ser Ser Ile Ser Ala Arg
        35                  40                  45

Thr Gly Asp Pro Val Thr Asn Met Ser Pro Ser Ser Leu Leu Gly Leu
    50                  55                  60

Leu Ala Gly Leu Gln Val Val Tyr Phe Leu Trp Thr Lys Ile Leu Thr
65                  70                  75                  80

Ile Pro Gln Ser Leu Asp Ser Trp Trp Thr Ser Leu Asn Phe Leu Gly

-continued

```
                     85                  90                  95
Gly Ala Pro Val Cys Pro Gly Gln Asn Ser Gln Ser Pro Thr Ser Asn
            100                 105                 110

His Ser Pro Thr Ser Cys Pro Pro Ile Cys Pro Gly Tyr Arg Trp Met
        115                 120                 125

Cys Leu Arg Arg Phe Ile Ile Phe Leu Phe Ile Leu Leu Leu Cys Leu
        130                 135                 140

Ile Phe Leu Leu Val Leu Leu Asp Tyr Gln Gly Met Leu Pro Val Cys
145                 150                 155                 160

Pro Leu Ile Pro Gly Ser Ser Thr Thr Ser Thr Gly Pro Cys Lys Thr
                165                 170                 175

Cys Met Thr Thr Pro Gln Gly Thr Ser Met Tyr Pro Ser Cys Cys Cys
                180                 185                 190

Thr Lys Pro Ser Asp Gly Asn Cys Thr Cys Ile Pro Ile Pro Ser Ser
                195                 200                 205

Trp Ala Phe Gly Lys Phe Leu Trp Glu Trp Ala Ser Val Arg Phe Ser
        210                 215                 220

Trp Leu Ser Leu Leu Ala Pro Phe Val Gln Arg Phe Val Gly Leu Ser
225                 230                 235                 240

Pro Thr Val Trp Leu Ser Val Ile Trp Met Met Trp Phe Trp Gly Pro
                245                 250                 255

Ser Leu Phe Ser Ile Leu Ser Pro Phe Leu Pro Leu Leu Pro Leu Phe
                260                 265                 270

Phe Trp Leu Trp Val Tyr Ile
                275
```